US012729224B2

(12) United States Patent
Kiani et al.

(10) Patent No.: US 12,729,224 B2
(45) Date of Patent: Sep. 8, 2026

(54) TARGETING MYD88 GENE IN VITRO AND IN VIVO

(71) Applicant: University of Pittsburgh—Of the Commonwealth System of Higher Education, Pittsburgh, PA (US)

(72) Inventors: Samira Kiani, Los Altos, CA (US); Tahere Mokhtari, Pittsburgh, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 331 days.

(21) Appl. No.: 18/579,170

(22) PCT Filed: Jul. 15, 2022

(86) PCT No.: PCT/US2022/073784
§ 371 (c)(1),
(2) Date: Jan. 12, 2024

(87) PCT Pub. No.: WO2023/288306
PCT Pub. Date: Jan. 19, 2023

(65) Prior Publication Data

US 2024/0336663 A1 Oct. 10, 2024

Related U.S. Application Data

(60) Provisional application No. 63/356,280, filed on Jun. 28, 2022, provisional application No. 63/222,893, filed on Jul. 16, 2021.

(51) Int. Cl.

| | |
|---|---|
| ***C07K 14/435*** | (2006.01) |
| ***A61K 48/00*** | (2006.01) |
| ***A61P 29/00*** | (2006.01) |
| ***C12N 15/86*** | (2006.01) |
| *A61K 38/00* | (2006.01) |

(52) U.S. Cl.
CPC .......... *C07K 14/435* (2013.01); *A61K 48/005* (2013.01); *A61P 29/00* (2018.01); *C12N 15/86* (2013.01); *A61K 38/00* (2013.01); *C07K 2319/81* (2013.01); *C12N 2750/14143* (2013.01)

(58) Field of Classification Search
None
See application file for complete search history.

(56) References Cited

U.S. PATENT DOCUMENTS

| | | | |
|---|---|---|---|
| 2005/0084885 | A1 | 4/2005 | Barbas, III et al. |
| 2017/0251645 | A1 | 9/2017 | Cox, III et al. |
| 2020/0149114 | A1 | 5/2020 | Treon |

FOREIGN PATENT DOCUMENTS

| | | | |
|---|---|---|---|
| WO | WO 2018/212361 | A1 | 11/2018 |
| WO | WO 2020/097344 | A1 | 5/2020 |

OTHER PUBLICATIONS

International Search Authority, International Search Report and Written Opinion issued in International Patent Application No. PCT/US2022/073784, mailed on Jan. 4, 2023.

Chen et al., "Fusion Protein Linkers: Property, Design and Functionality," *Adv. Drug Deliv. Rev.*, 65(10); 1357-1369 (2013).

Hajj et al., "Branched-Tail Lipid Nanoparticles Potently Deliver mRNA In Vivo due to Enhanced Ionization at Endosomal pH," *Small*, 15: 1805097 (2019), 7 pp.

Johnson, "Protein/Peptide Tags," *Mater. Methods*, 2: 116 (2012), DOI//dx.doi.org/10.13070/mm.en.2.116, 14 pp.

Krienke et al., "A noninflammatory mRNA vaccine for treatment of experimental autoimmune encephalomyelitis", *Science*, 371: 145-153 (2021).

Mandell et al., "Zinc Finger Tools: custom DNA-binding domains for transcription factors and nucleases," *Nucleic Acids Research*, 34: W516-W5523 (2006).

Moghadam et al., "Synthetic immunomodulation with a CRISPR super-repressor in vivo," *Nat. Cell Biol.*, 22(9): 1143-1154 (2020).

*Primary Examiner* — Anna Pagonakis
(74) *Attorney, Agent, or Firm* — Leydig, Voit & Mayer, Ltd.

(57) ABSTRACT

A non-naturally occurring zinc finger protein, wherein the zinc finger protein specifically binds to the promoter region of the Myd88 gene, is provided, as well as related polynucleotides, vectors, cells, and pharmaceutical compositions. In some aspects, the zinc finger protein comprises one or more repressors. Pharmaceutical compositions comprising a pharmaceutically acceptable carrier and: (A) one or more RNA interference (RNAi) agents targeting the Myd88 gene, or related polynucleotides, vectors, or cells; (B) a target antigen or a polynucleotide encoding the target antigen; and (C) a gene therapy are also provided. Methods for ameliorating inflammation and/or immune response in a subject using the RNAi agents, zinc finger protein, polynucleotides, vectors, cells, and pharmaceutical compositions also are provided.

20 Claims, 73 Drawing Sheets

Specification includes a Sequence Listing.

PE indicating the presence of anti-FLAG ZFR

PE indicating the presence of anti-FLAG ZFR

PE indicating the presence of anti-FLAG ZFR

Unstained (A)

Anti-ZFR stained (Untransfected) (B)

Anti-ZFR stained J2 (DNA transfected CH27) (C)

PE indicating the presence of anti-FLAG ZFR

Conditions (0.75/mg/kg mouse Dosage)

FIG. 28

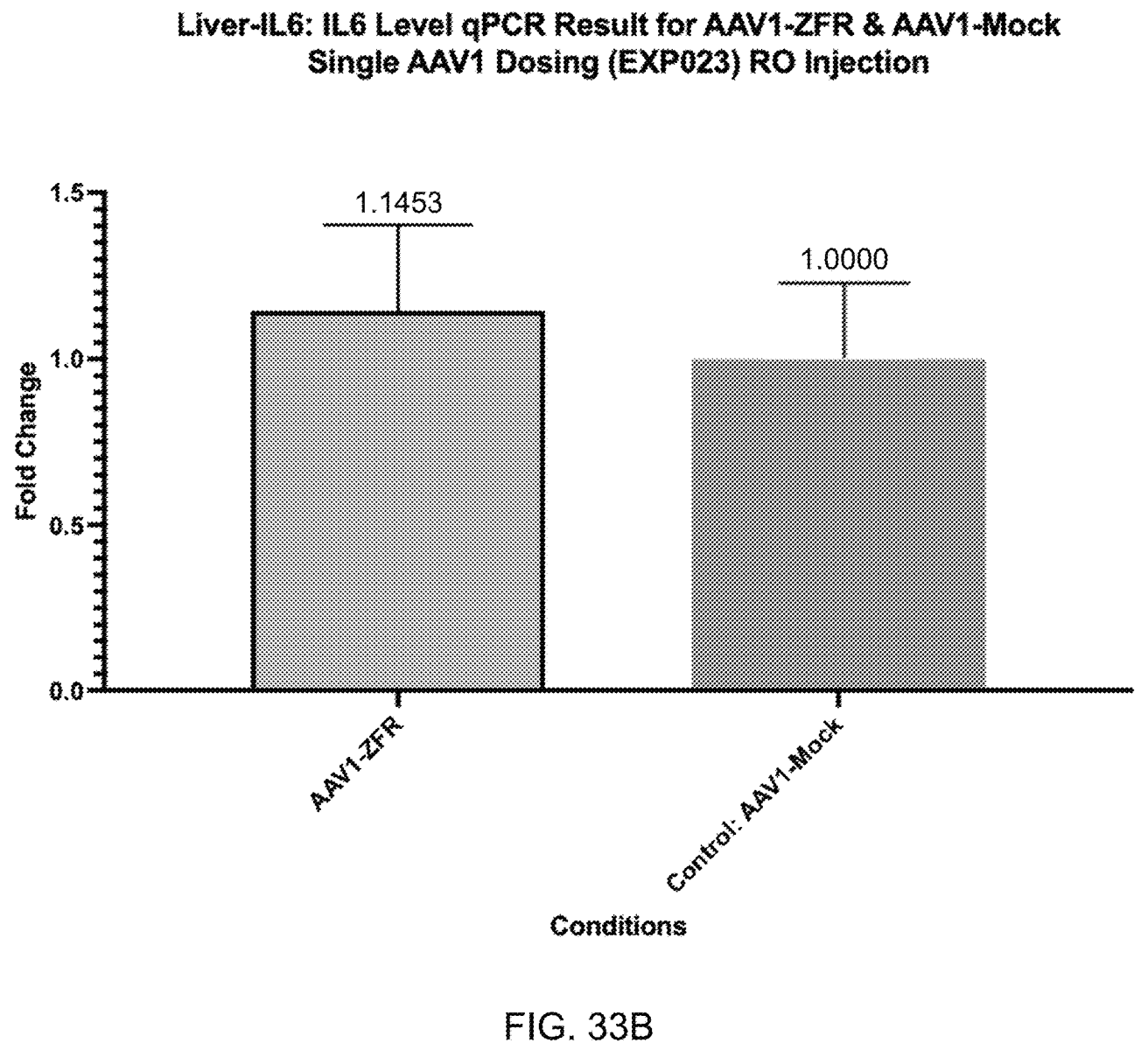

Liver-IL6: IL6 Level qPCR Result for AAV1-ZFR & AAV1-Mock
Single AAV1 Dosing (EXP023) RO Injection Fold Change 1.5
1.0
0.5
0.0

1.1453
1.0000

AAV1-ZFR
Control: AAV1-Mock

Conditions

FIG. 33B

TARGETING MYD88 GENE IN VITRO AND IN VIVO

CROSS-REFERENCE TO RELATED APPLICATIONS

This patent application is the U.S. National Stage of International Patent Application No. PCT/US2022/073784, filed Jul. 15, 2022, which claims the benefit of U.S. Provisional Patent Application No. 63/222,893, filed Jul. 16, 2021, and U.S. Provisional Patent Application No. 63/356,280, filed Jun. 28, 2022, each of which is incorporated by reference in its entirety herein.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 17,388 Byte XML file named "770225_ST26.xml," dated Jan. 12, 2024.

BACKGROUND OF THE INVENTION

The Myd88 gene encodes a cytosolic adapter protein that plays a central role in the innate and adaptive immune response. This protein functions as a signal transducer in the interleukin-1 and Toll-like receptor signaling pathways. These pathways regulate that activation of numerous proinflammatory genes.

There is a desire for new therapies for treating disorders associated with inflammation or improper or unwanted immune responses (e.g., autoimmune disorders) by targeting Myd88 expression.

BRIEF SUMMARY OF THE INVENTION

An aspect of the invention provides a non-naturally occurring zinc finger protein, wherein the zinc finger protein specifically binds to the promoter region of the Myd88 gene.

In one aspect, the zinc finger comprises one or more (e.g., one, two, three, four, five or six) of the following: (i) a N-terminal fixed domain, (ii) a N-terminal backbone domain, (iii) a variable recognition helix, (iv) a C-terminal backbone domain, (v) a zinc finger linker, and (vi) a C-terminal domain.

The zinc finger can comprise one or more repressors, such as Hp1a, Krab, MeCP2, and combinations thereof.

An aspect of the invention also provides a cell (e.g., an isolated cell) comprising one or more of the zinc finger proteins, as well as a polynucleotide encoding one or more of the zinc finger proteins and a vector comprising the polynucleotide. Additionally, the invention provides a pharmaceutical composition comprising (i) one or more of the zinc finger proteins, (ii) one or more of the cells, (iii) one or more of the polynucleotides, or (iv) one or more of the vectors and a pharmaceutically acceptable carrier.

Additionally, an aspect of the invention provides a method for ameliorating inflammation and/or immune response in a subject, the method comprising administering to the subject a therapeutically effective amount of (i) one or more of the zinc finger proteins, (ii) one or more of the cells, (iii) one or more of the polynucleotides, (iv) one or more of the vectors, or (v) a pharmaceutical composition thereof, thereby ameliorating inflammation and/or immune response in the subject.

Another aspect of the invention provides a pharmaceutical composition comprising a pharmaceutically acceptable carrier and: (A) (i) one or more of the zinc finger proteins, (ii) one or more cells comprising the one or more zinc finger proteins, (iii) one or more polynucleotides encoding the one or more zinc finger proteins, or (iv) one or more vectors comprising the one or more polynucleotides: (B) a target antigen or a polynucleotide encoding the target antigen: and (C) a gene therapy.

Additionally, an aspect of the invention provides a set of compositions comprising: (A) (i) one or more of the zinc finger proteins, (ii) one or more cells comprising the one or more zinc finger proteins, (iii) one or more polynucleotides encoding the one or more zinc finger proteins, or (iv) one or more vectors comprising the one or more polynucleotides: (B) a target antigen or a polynucleotide encoding the target antigen: and (C) a gene therapy.

Another aspect of the invention provides a method for inducing immune tolerance in a subject, the method comprising administering to the subject a therapeutically or prophylactically effective amount of (i) one or more of the zinc finger proteins, (ii) a target antigen or a polynucleotide encoding the target antigen, (iii) one or more cells comprising (i) and (ii), (iv) one or more polynucleotides encoding (i), (v) one or more vectors comprising the one or more polynucleotides, or (vi) a pharmaceutical composition comprising any one of (i)-(v), thereby inducing immunogenic tolerance against the target antigen.

An aspect of the invention also provides a pharmaceutical composition comprising a pharmaceutically acceptable carrier and: (A) (i) one or more RNA interference (RNAi) agents targeting the Myd88 gene, (ii) one or more cells comprising the one or more RNAi agents, (iii) one or more polynucleotides encoding the one or more RNAi agents, or (iv) one or more vectors comprising the one or more polynucleotides: (B) a target antigen or a polynucleotide encoding the target antigen: and (C) a gene therapy.

Another aspect of the invention provides a set of compositions comprising: (A) (i) one or more RNAi agents targeting the Myd88 gene, (ii) one or more cells comprising the one or more RNAi agents, (iii) one or more polynucleotides encoding the one or more RNAi agents, or (iv) one or more vectors comprising the one or more polynucleotides: (B) a target antigen or a polynucleotide encoding the target antigen: and (C) a gene therapy.

An aspect of the invention provides a method for inducing immune tolerance in a subject, the method comprising administering to the subject a therapeutically or prophylactically effective amount of: (A) (i) one or more RNAi agents targeting the Myd88 gene, (ii) one or more cells comprising the one or more RNAi agents, (iii) one or more polynucleotides encoding the one or more RNAi agents, or (iv) one or more vectors comprising the one or more polynucleotides: (B) a target antigen or a polynucleotide encoding a target antigen: and (C) a gene therapy, thereby inducing immunogenic tolerance against the target antigen.

mMYD88-ZFR-306$O_{10}$ in liver (A), spleen (B), blood (C), lung (D), and bone marrow (E).

FIGS. 3A-3D are graphs showing the fold change in tumor necrosis factor (TNF) alpha transcript levels (as measured by qPCR) in mice treated with LPS and either (i) mGFP-306$O_{10}$ or (ii) mMYD88-ZFR-306$O_{10}$ in liver (A), spleen (B), blood (C), and bone marrow (D).

FIGS. 4A-4D are graphs showing the fold change in interleukin 6 (IL6) transcript levels (as measured by qPCR) in mice treated with LPS and either (i) mGFP-306$O_{10}$ or (ii) mMYD88-ZFR-306$O_{10}$ in liver (A), spleen (B), blood (C), and bone marrow (D).

Figure 5A:
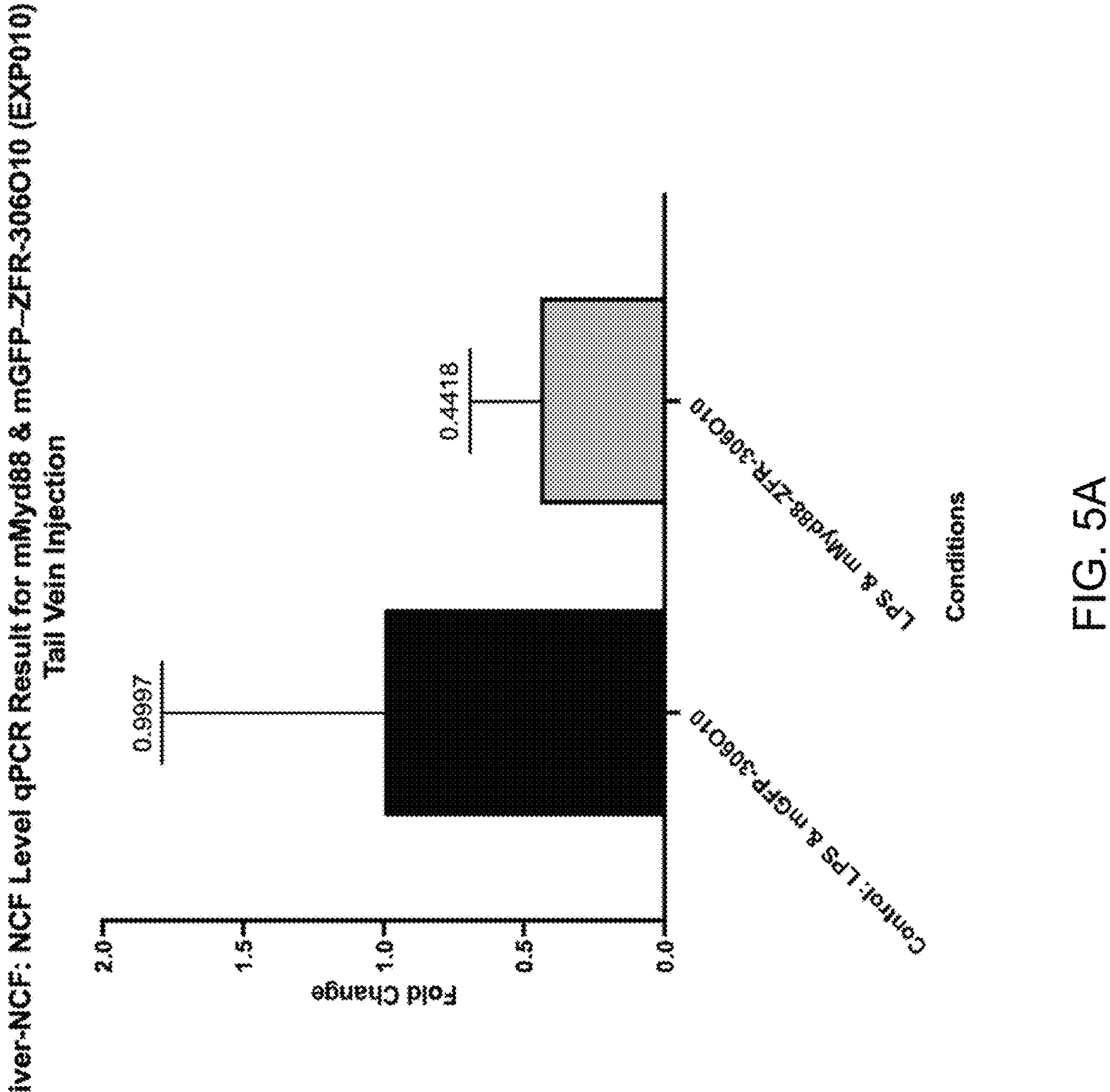
Figure 5B:
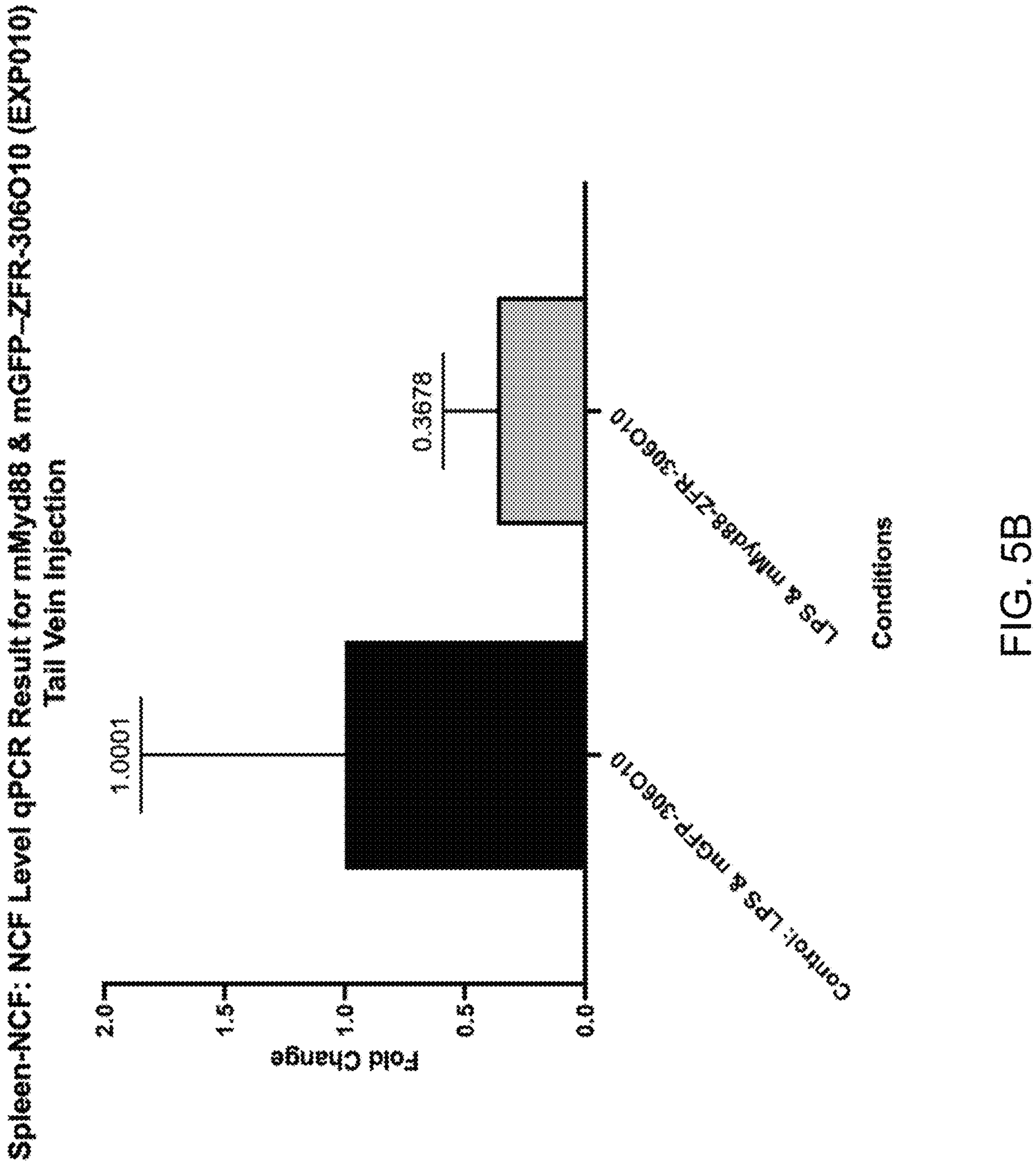
Figure 5C:
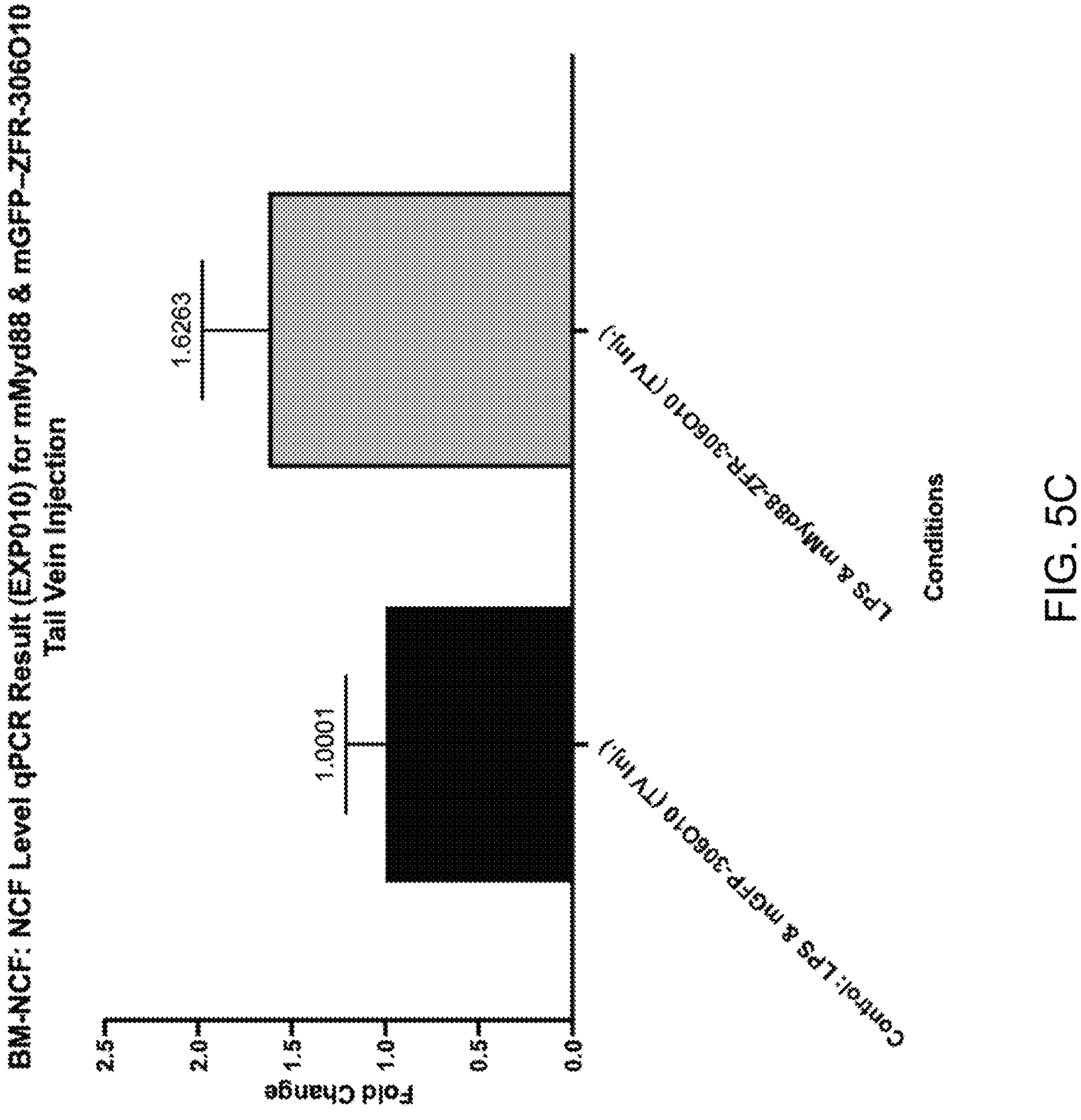

FIGS. 5A-5C are graphs showing the fold change in neutrophil chemotactic factor (NCF) transcript levels (as measured by qPCR) in mice treated with LPS and either (i) mGFP-306$O_{10}$ or (ii) mMYD88-ZFR-306$O_{10}$ in liver (A), spleen (B), and bone marrow (C).

Figure 6A:
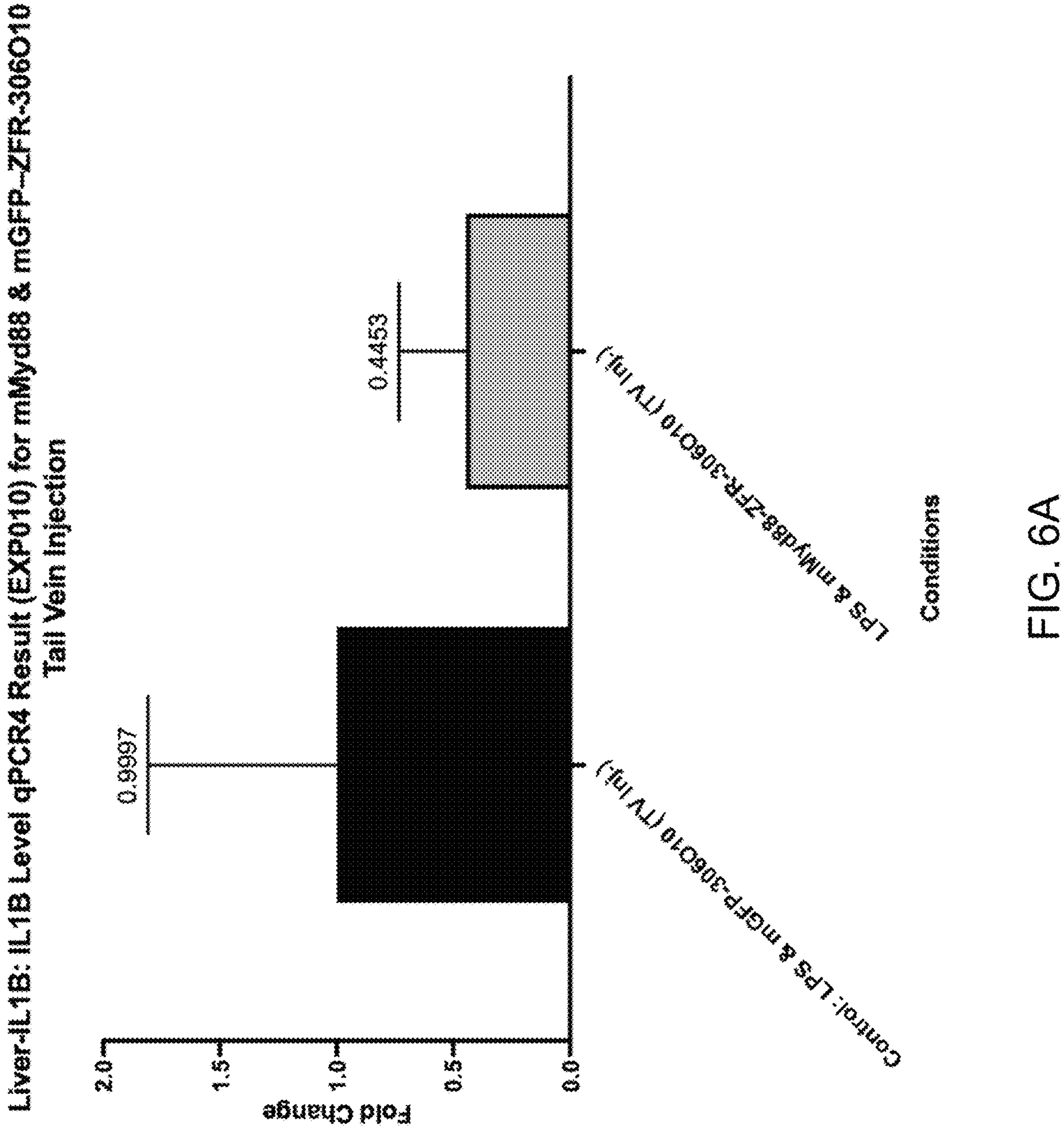
Figure 6B:
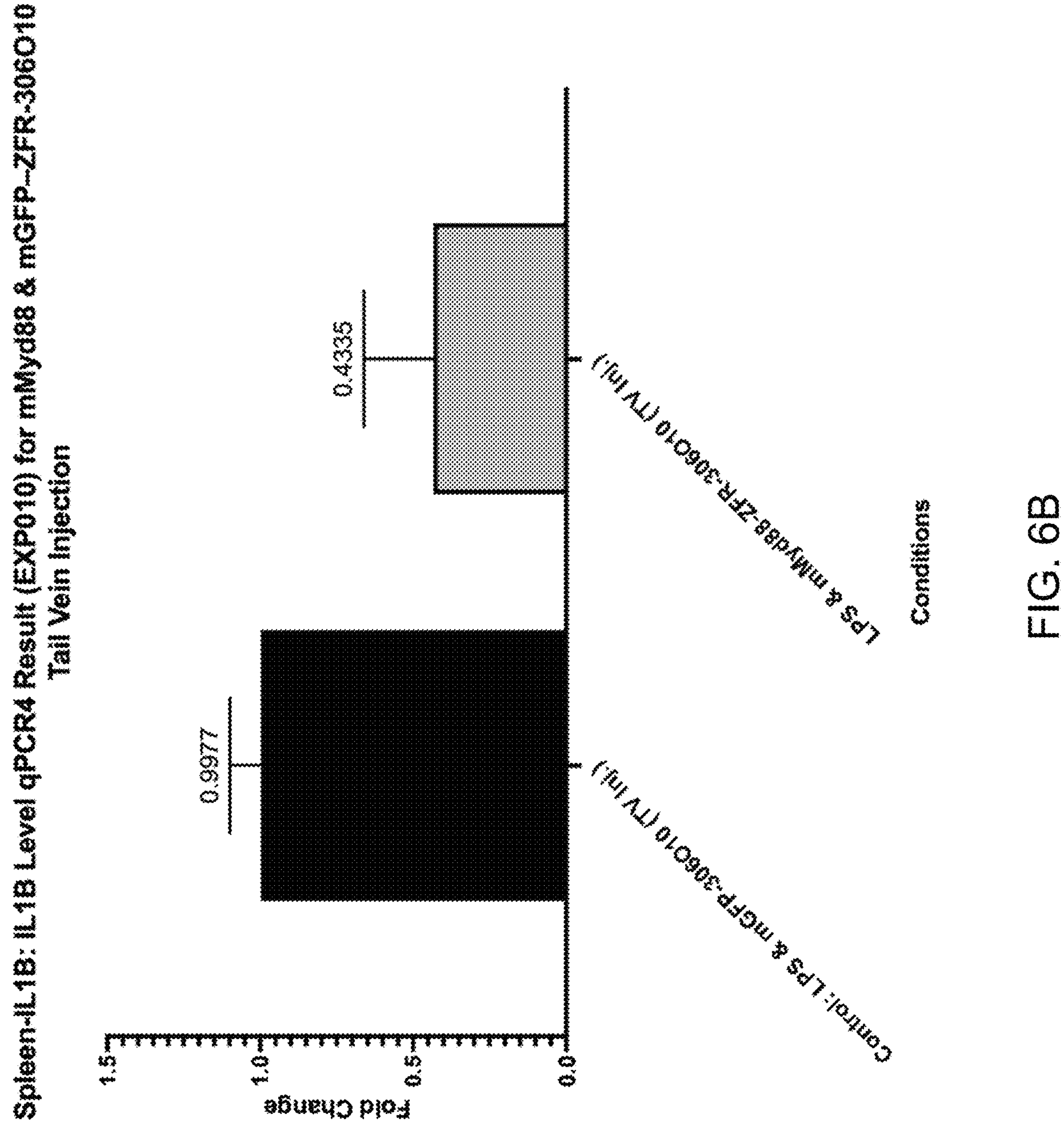
Figure 6C:
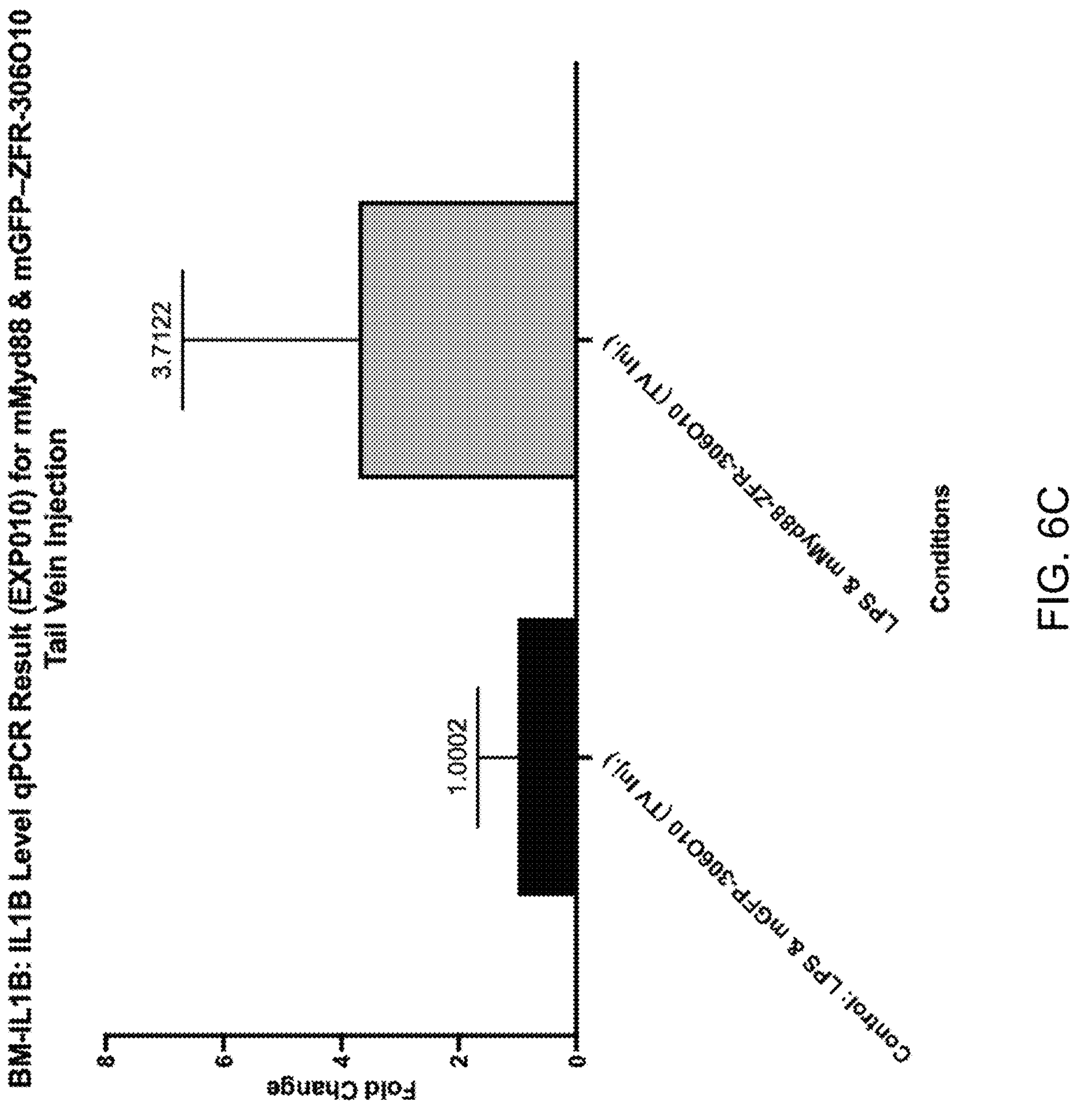

FIGS. 6A-6C are graphs showing the fold change in interleukin 1 (IL1) beta transcript levels (as measured by qPCR) in mice treated with LPS and either (i) mGFP-306$O_{10}$ or (ii) mMYD88-ZFR-306$O_{10}$ in liver (A), spleen (B), and bone marrow (C).

Figure 7A:
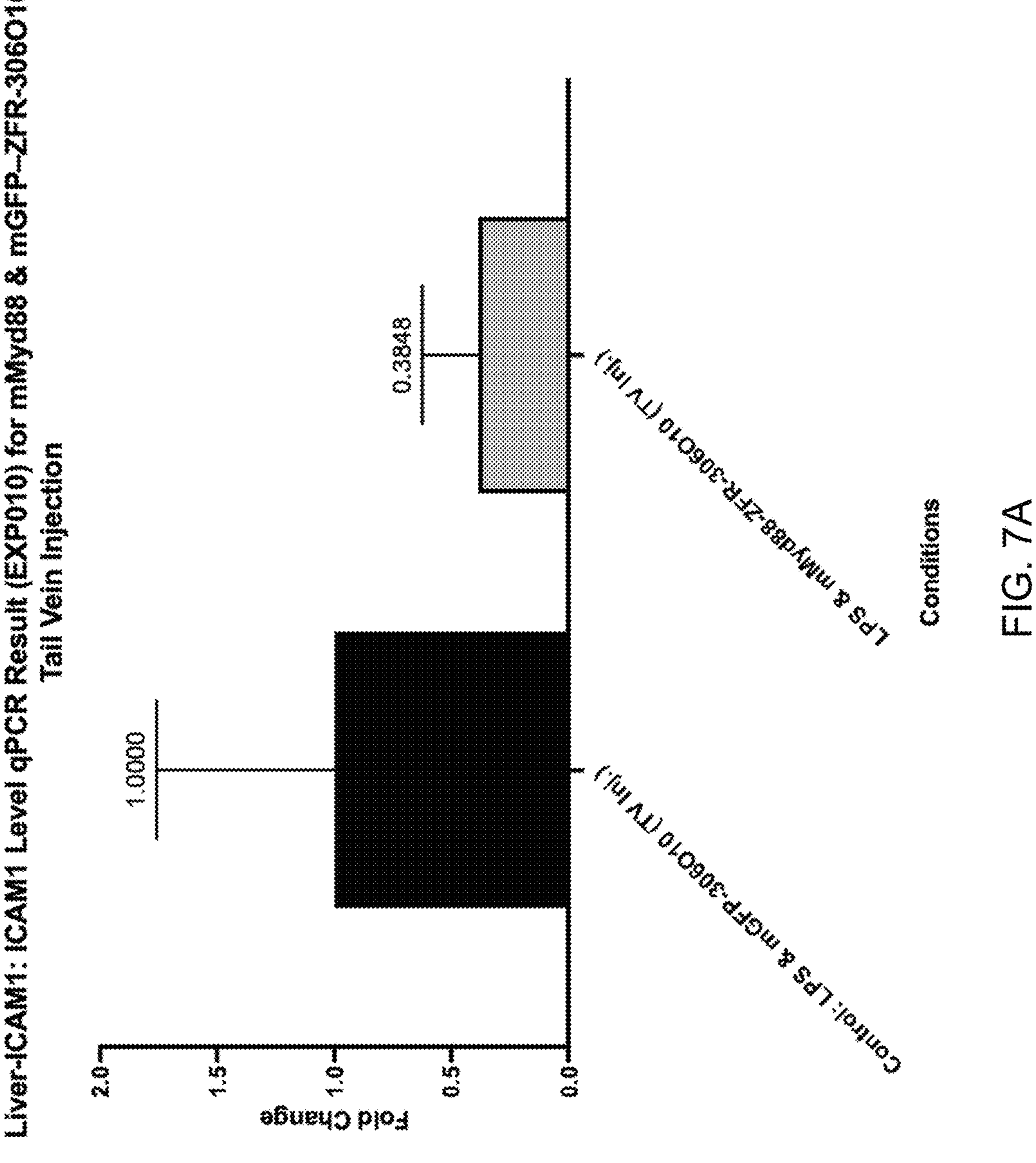
Figure 7B:
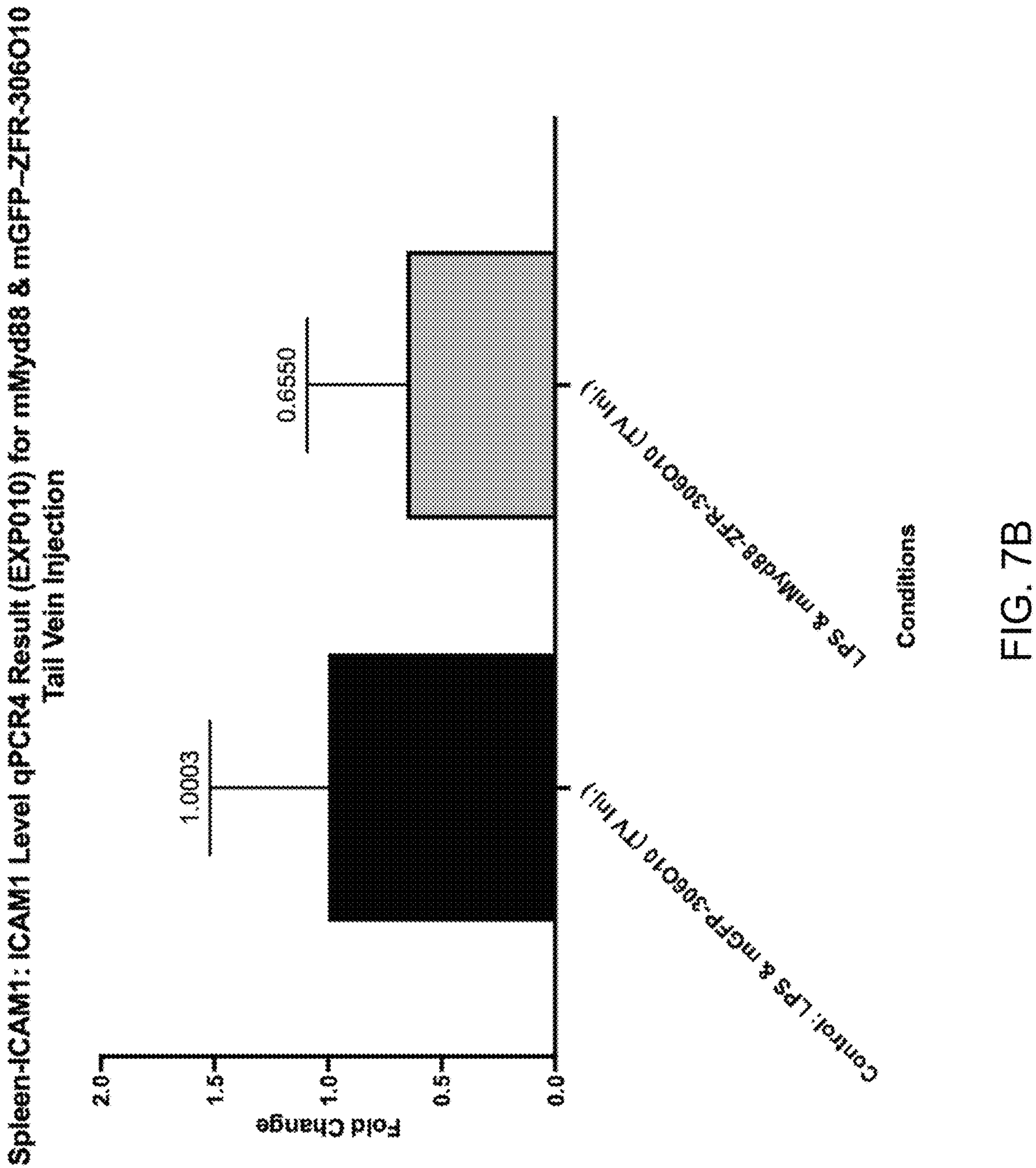

FIGS. 7A-7B are graphs showing the fold change in ICAM-1 (intercellular adhesion molecule 1) transcript levels (as measured by qPCR) in mice treated with LPS and either (i) mGFP-306$O_{10}$ or (ii) mMYD88-ZFR-306$O_{10}$ in liver (A) and spleen (B).

Figure 8:
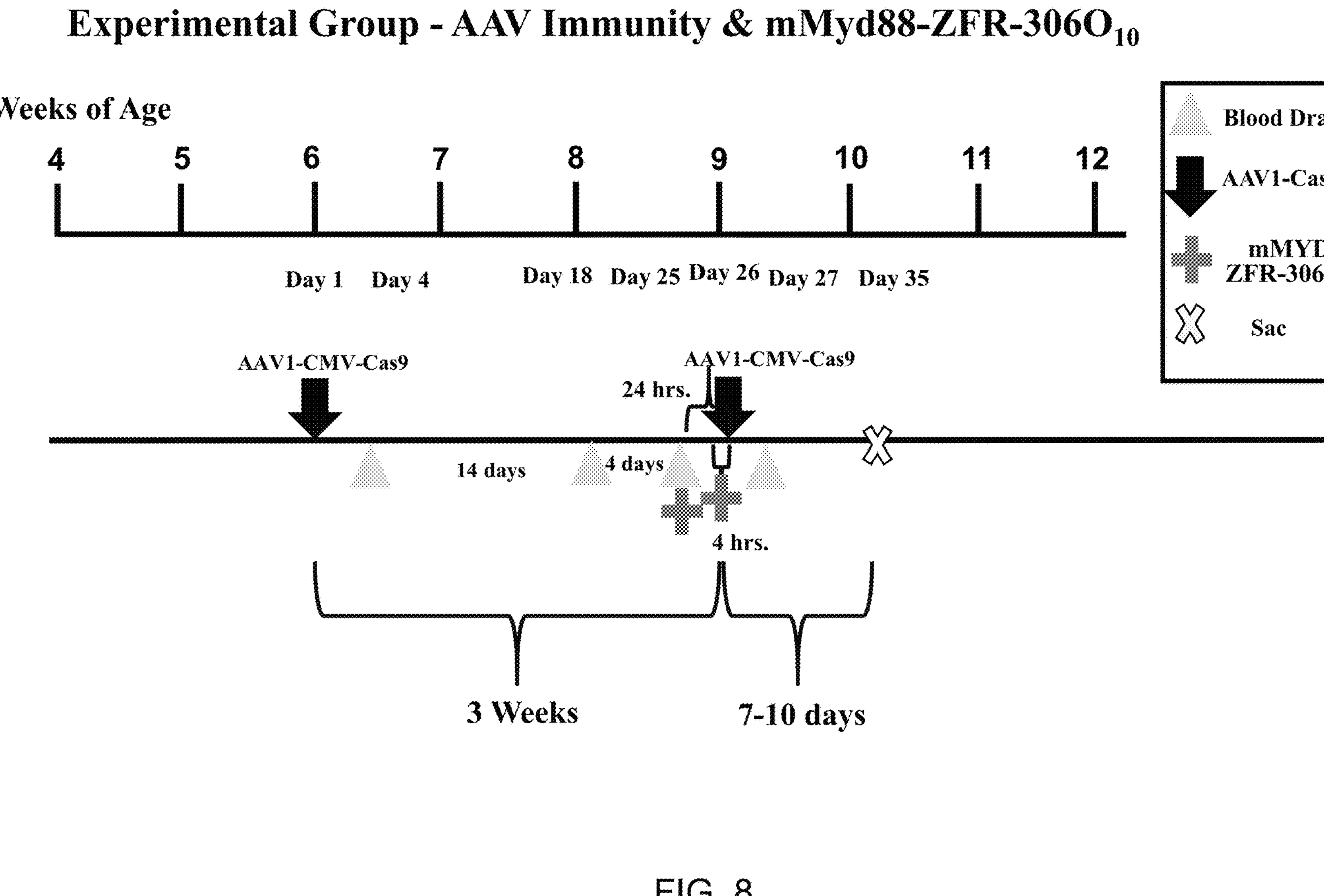

FIG. 8 is a schematic illustrating the time points at which mice were administered (i) LNP including an AAV1-CMV-Cas9 vector and (ii) mMYD88-ZFR-306$O_{10}$ (IP) and blood was drawn from the mice. LNP dosage is 1.5 mg/kg. “Sac” indicates when mice were sacrificed.

Figure 9:
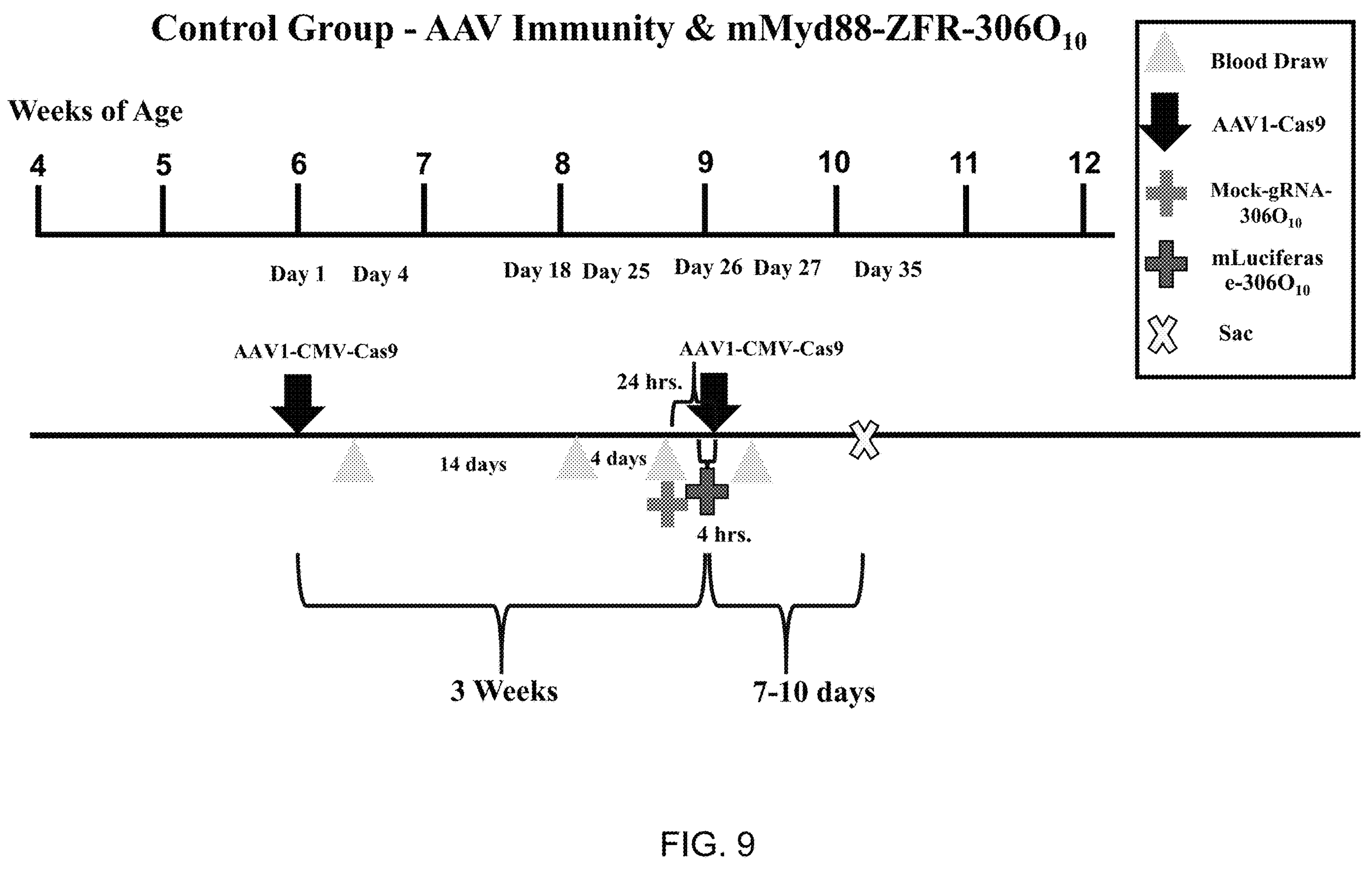
Figure 10A:
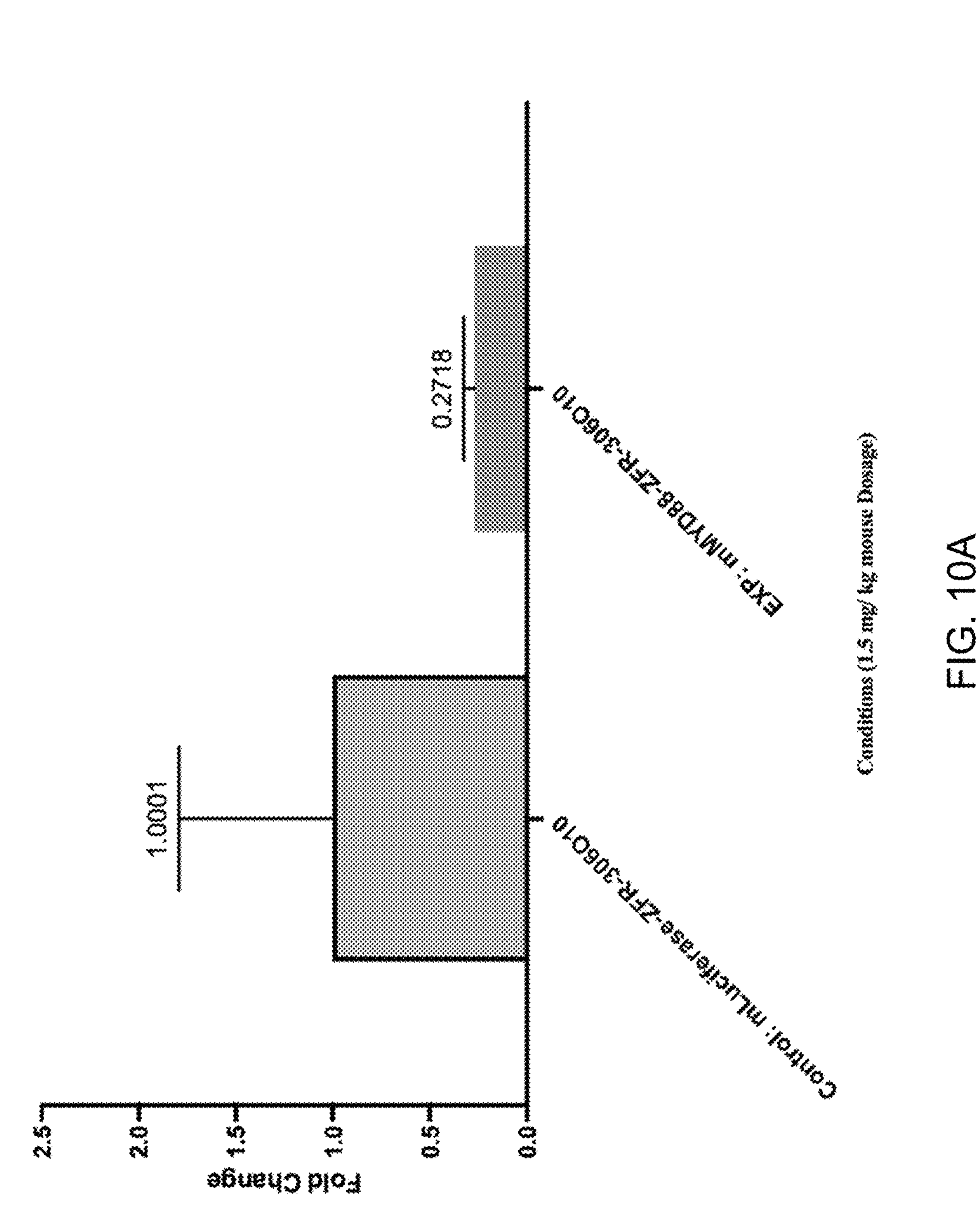
Figure 10B:
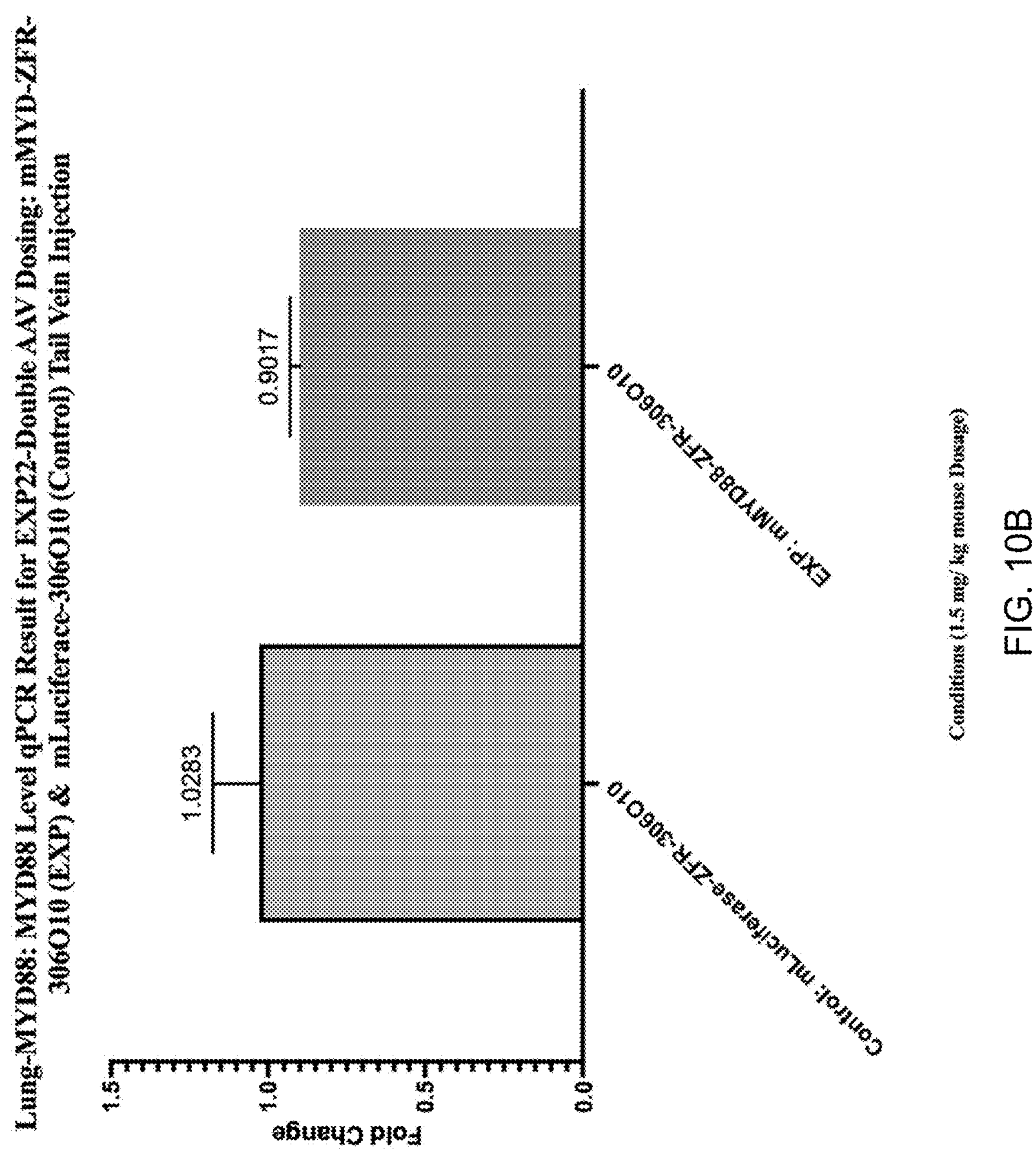
Figure 10C:
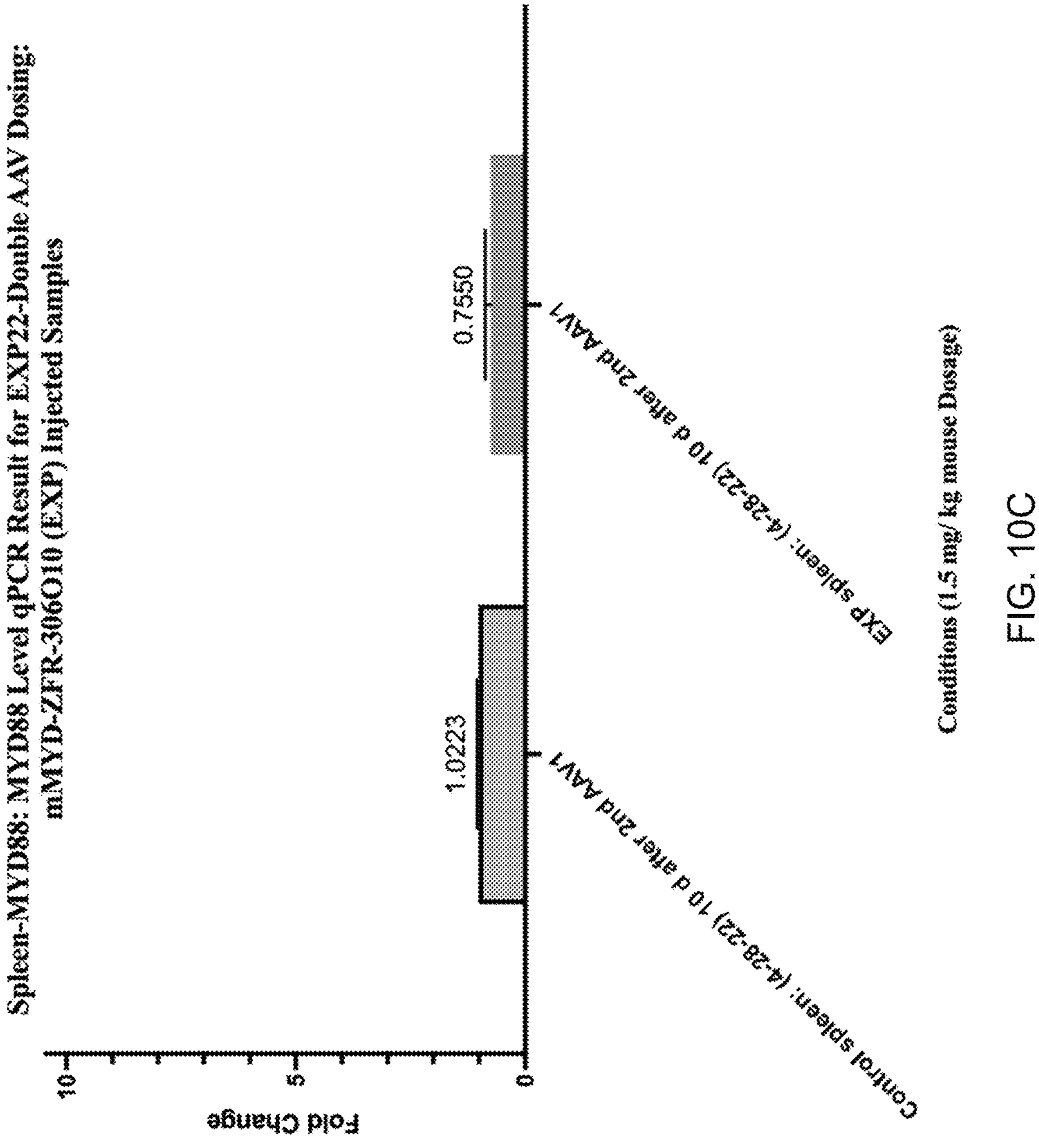
Figure 10D:
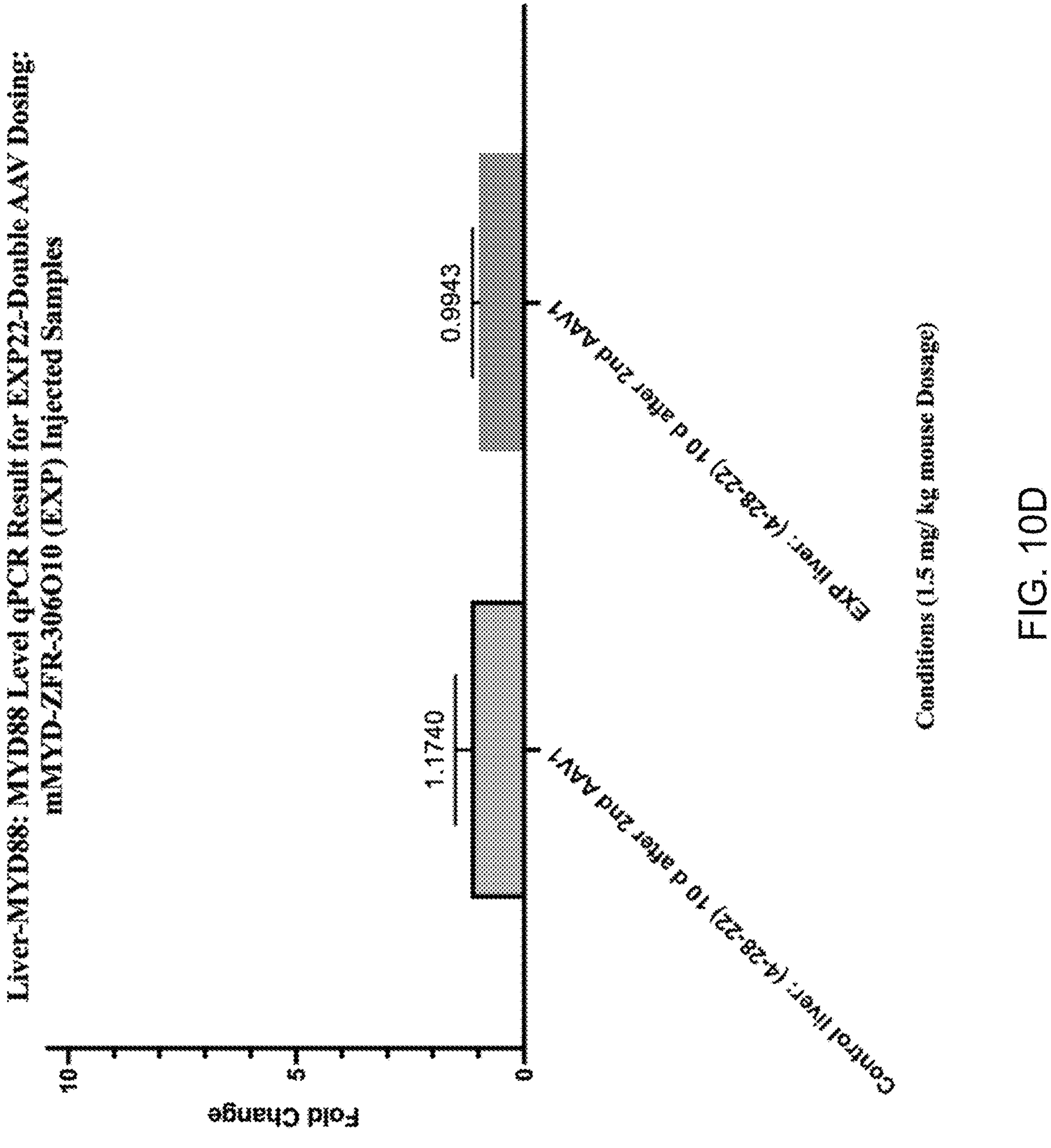

FIG. 9 is a schematic illustrating the time points at which mice were administered (i) LNP including an AAV1-CMV-Cas9 vector, (ii) Mock-gRNA-306$O_{10}$, and (iii) mLuciferase-306$O_{10}$ (IP) and blood was drawn. LNP dosage is 1.5 mg/kg. “Sac” indicates when mice were sacrificed.

FIGS. 10A-10D are graphs showing the fold change in MYD88 transcript levels (as measured by qPCR) in mice treated with AAV1-CMV-Cas9 vector and either (i) mLuciferase-306$O_{10}$ or (ii) mMYD88-ZFR-306$O_{10}$ in blood (A), lung (B), spleen (C), and liver (D). LNP dosage is 1.5 mg/kg.

Figure 11A:
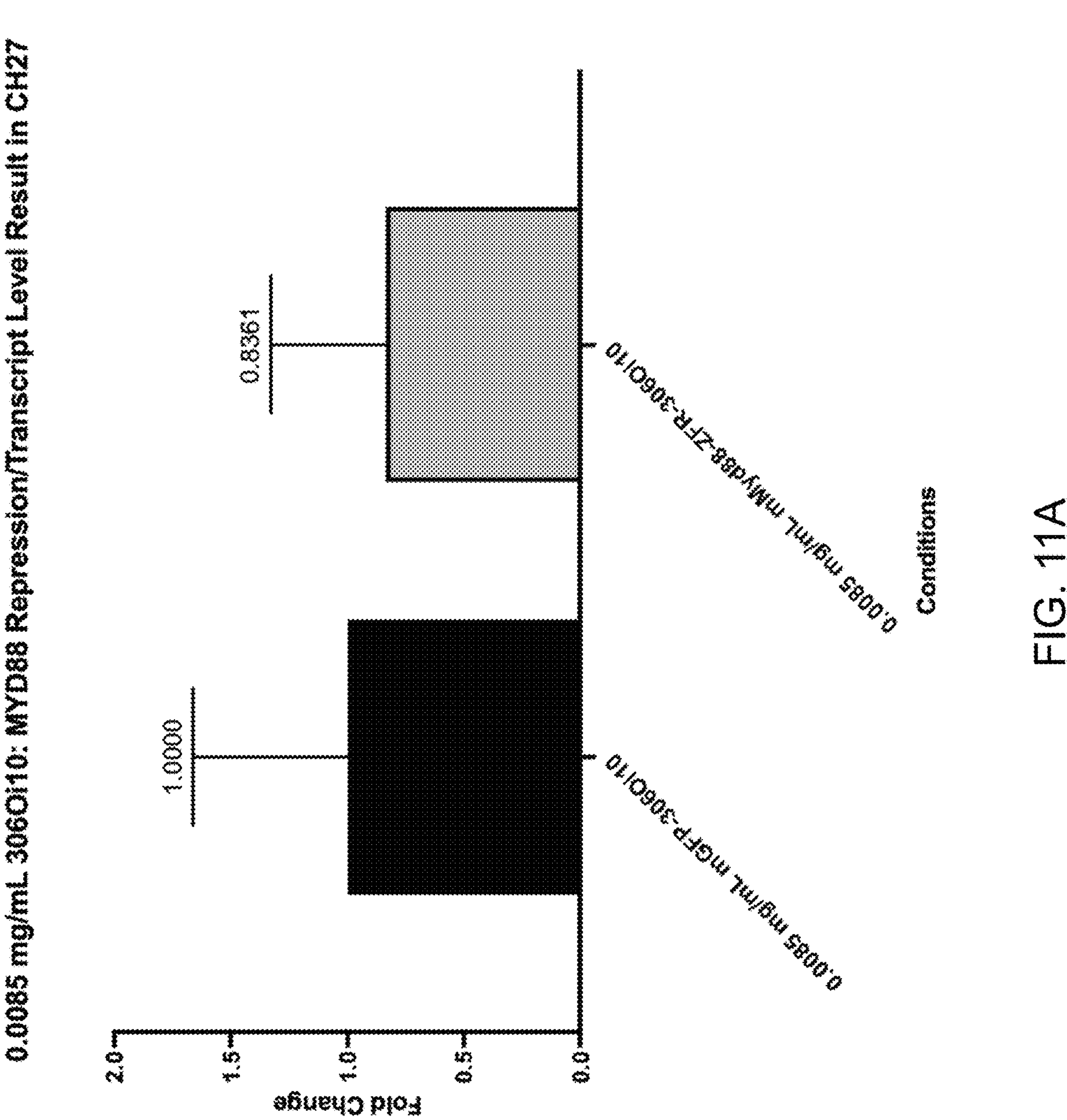
Figure 11B:
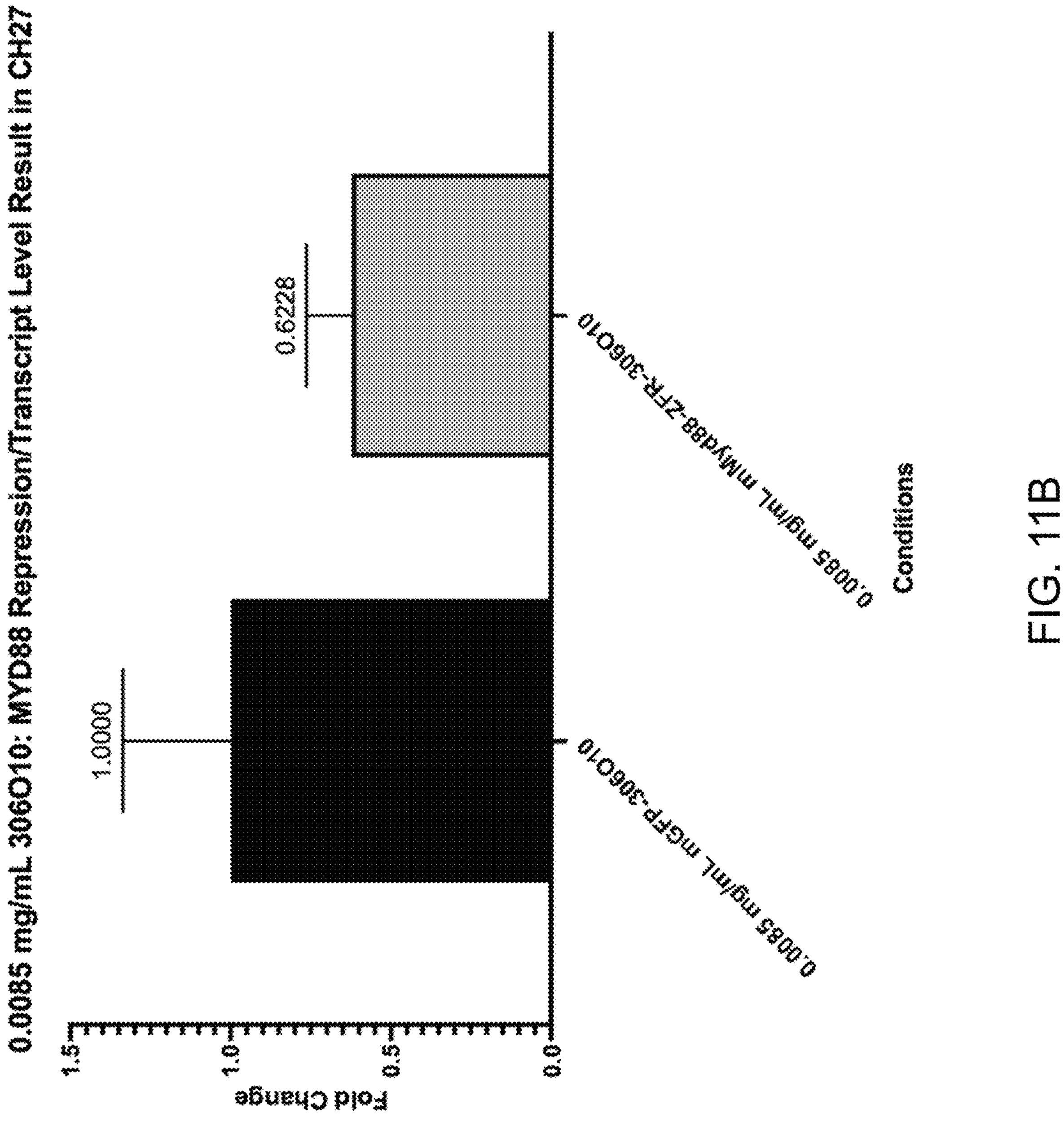

FIGS. 11A-11B are graphs showing the fold change in Myd88 gene expression following transfection of CH27 cells with (i) mGFP-3060i10 or mMYD88-ZFR-3060i10 (A) or (ii) mGFP-306$O_{10}$ or mMYD88-ZFR-306$O_{10}$ (B).

Figure 12B:
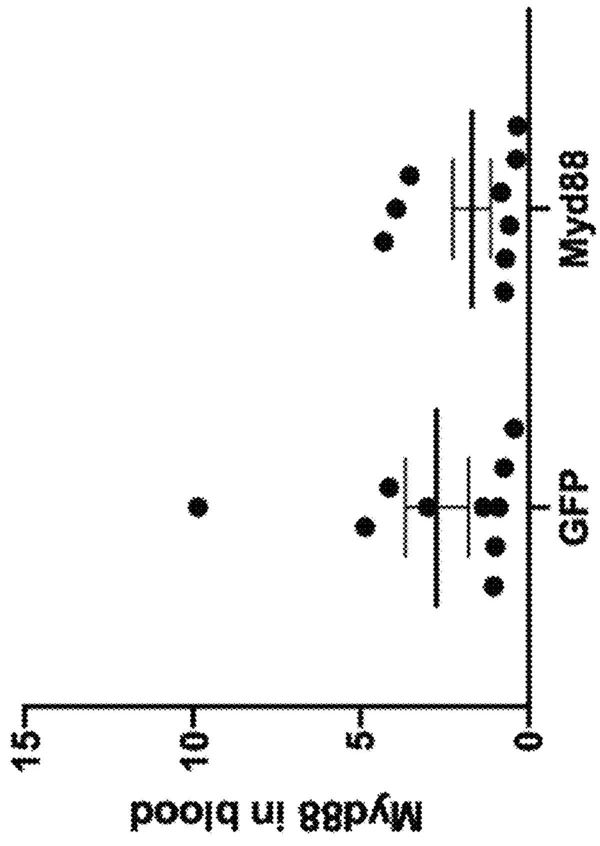
Figure 12A:
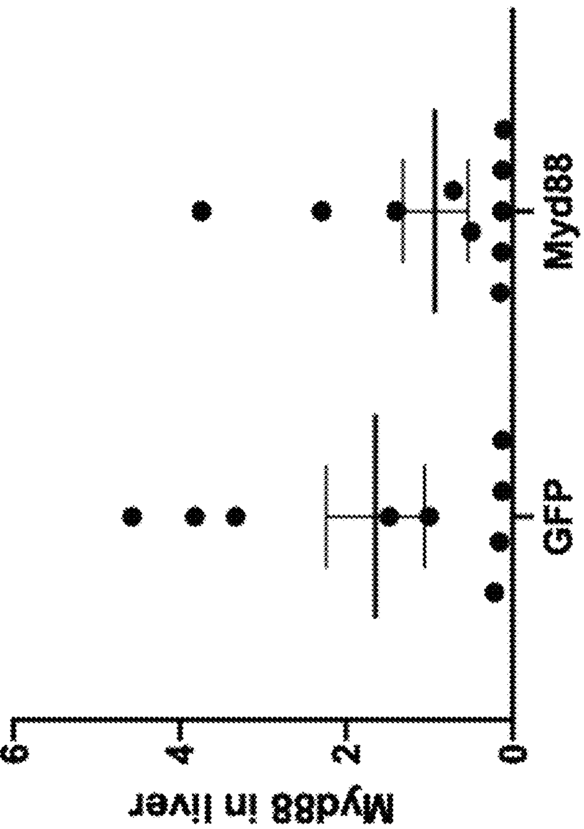
Figure 13B:
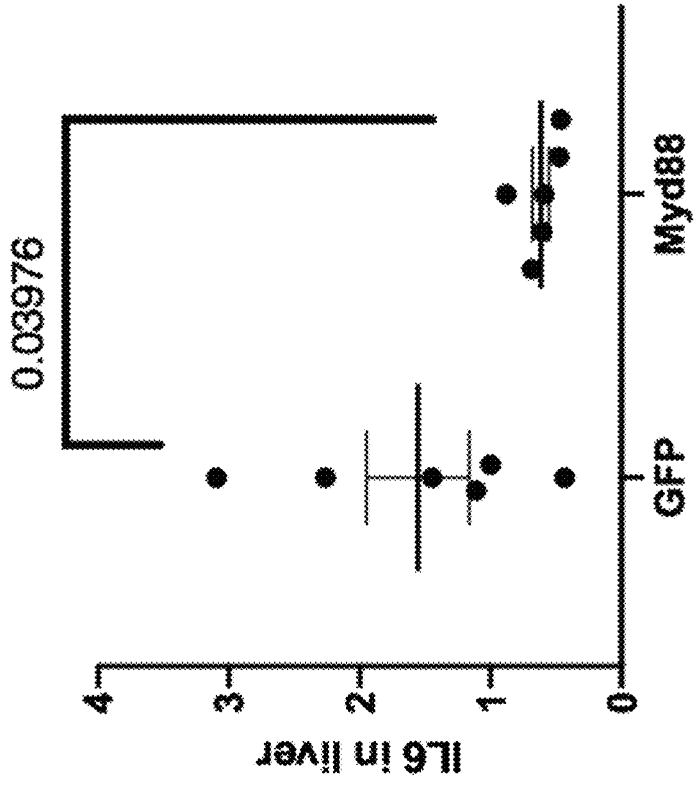
Figure 13A:
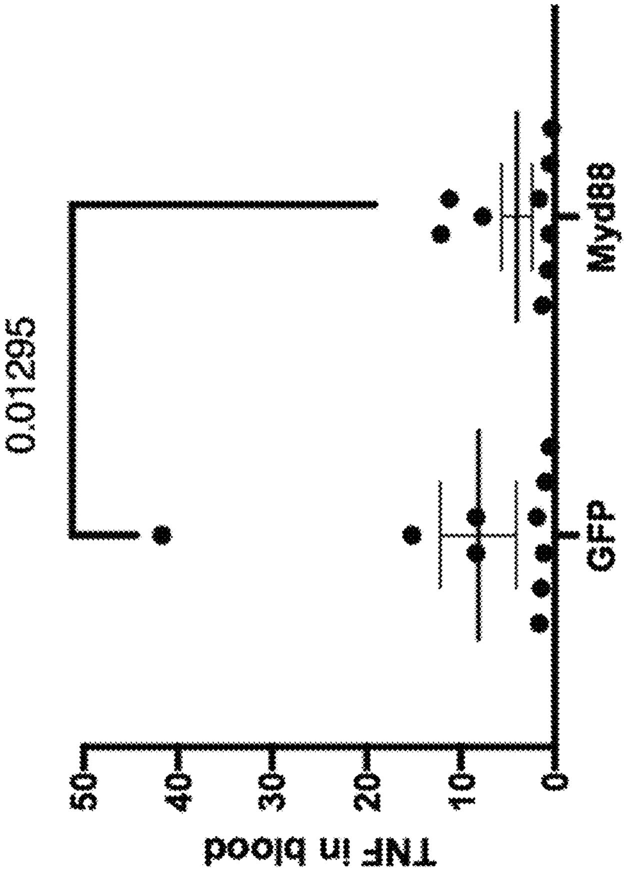
Figure 13D:
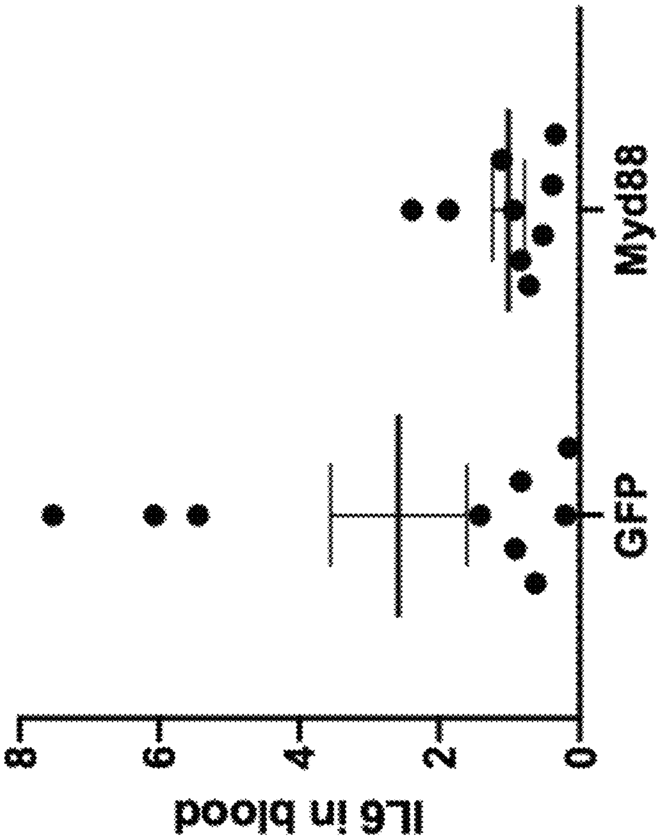
Figure 13C:
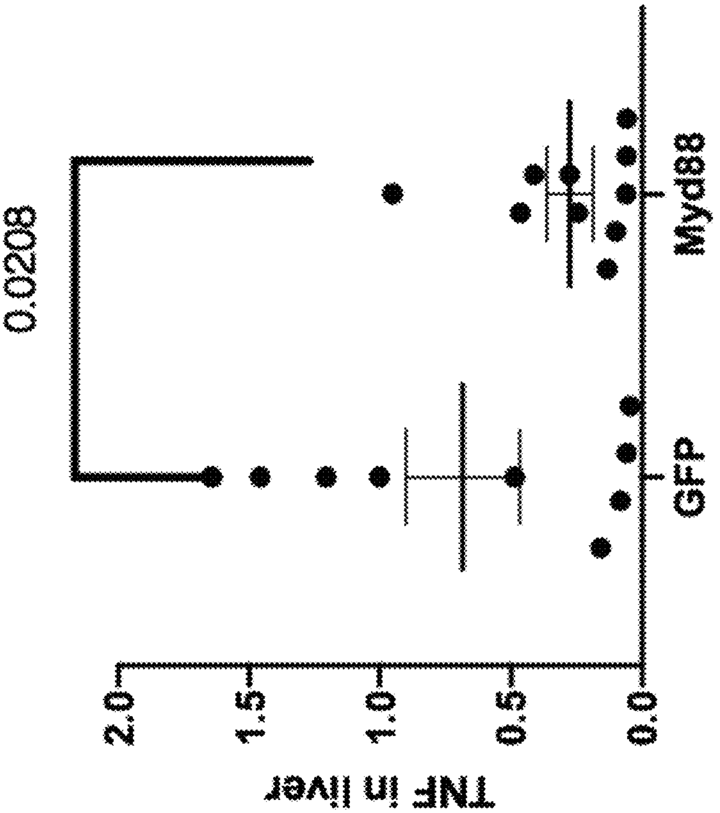
Figure 14A:
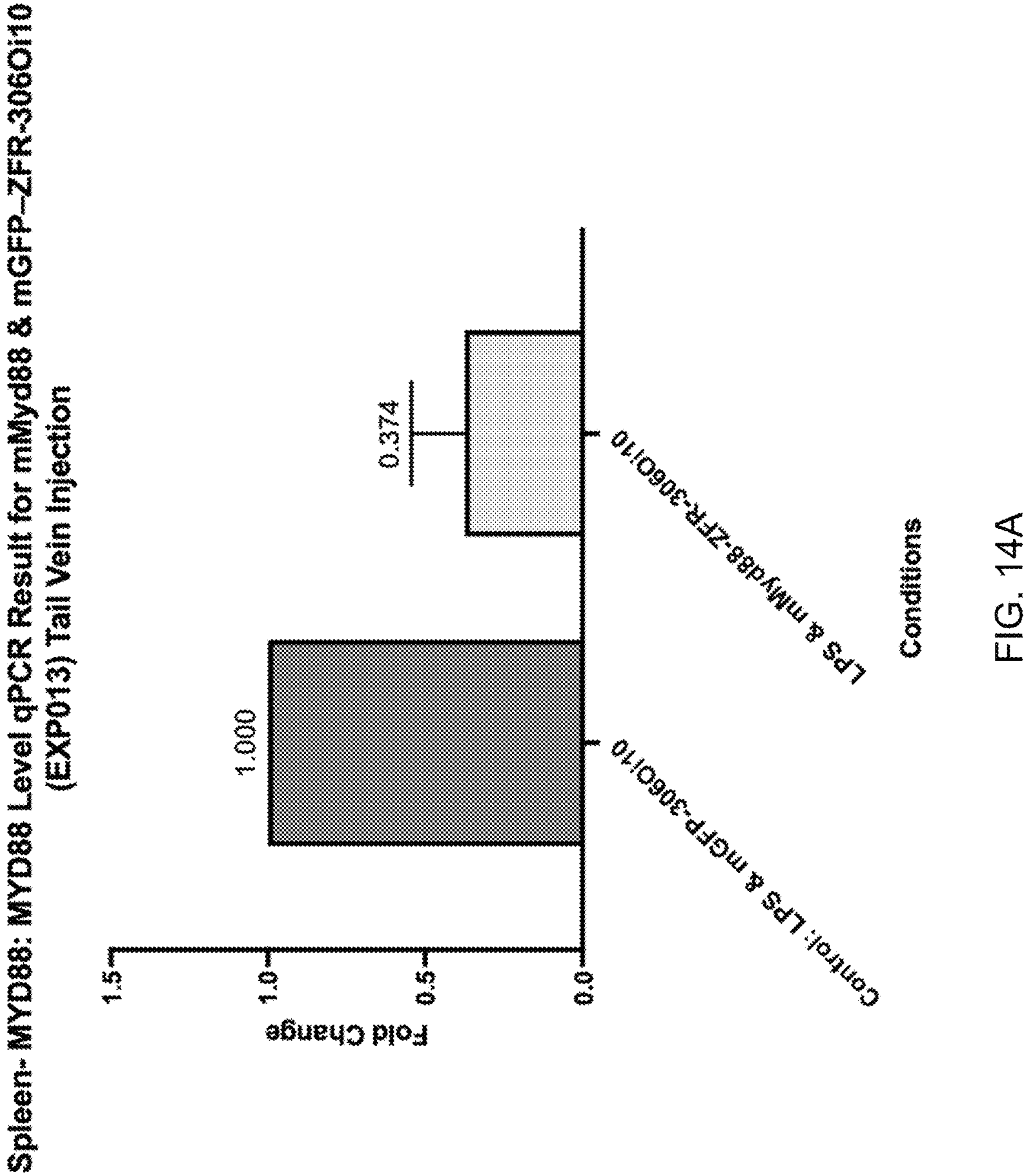
Figure 14B:
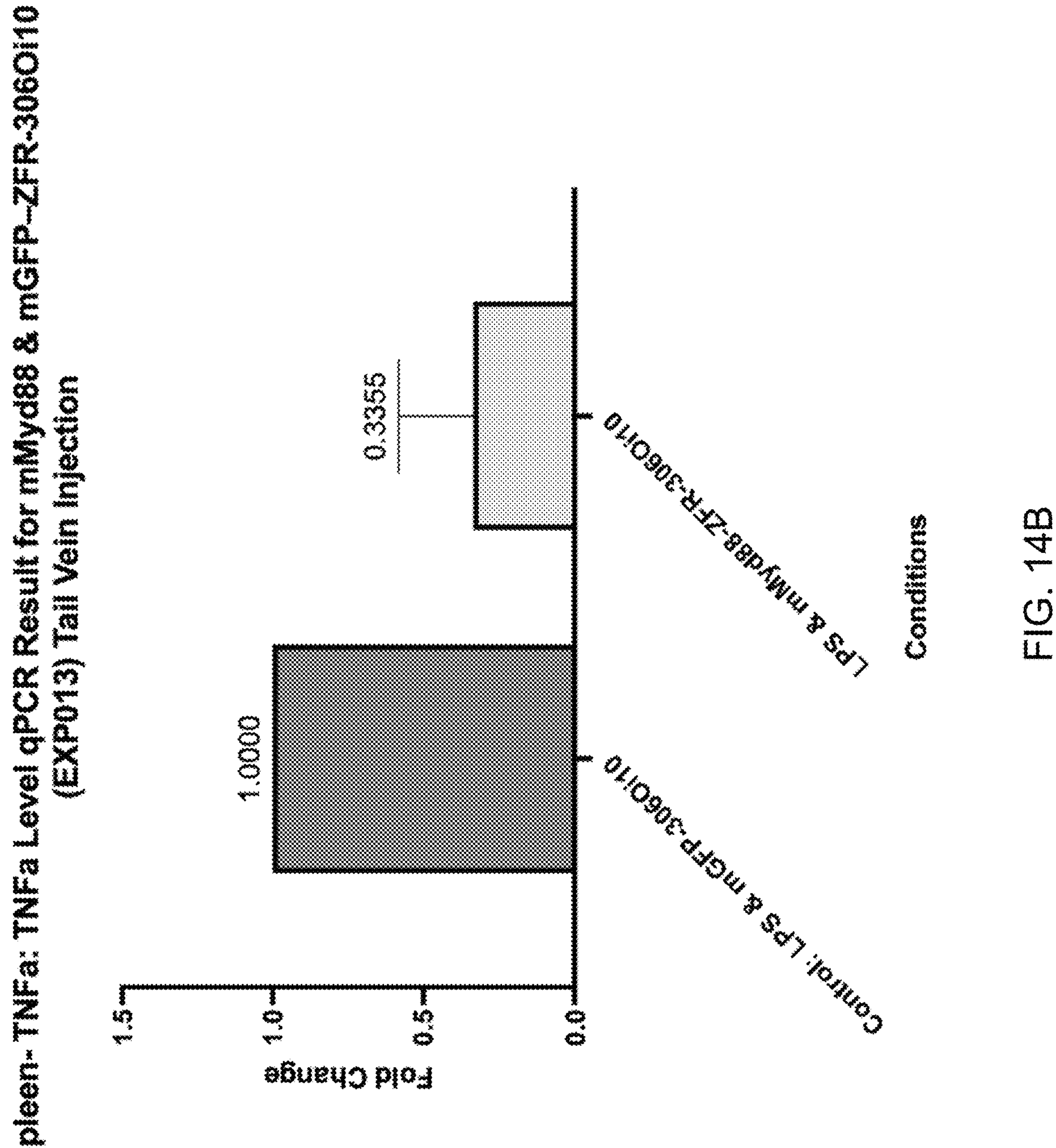
Figure 14C:
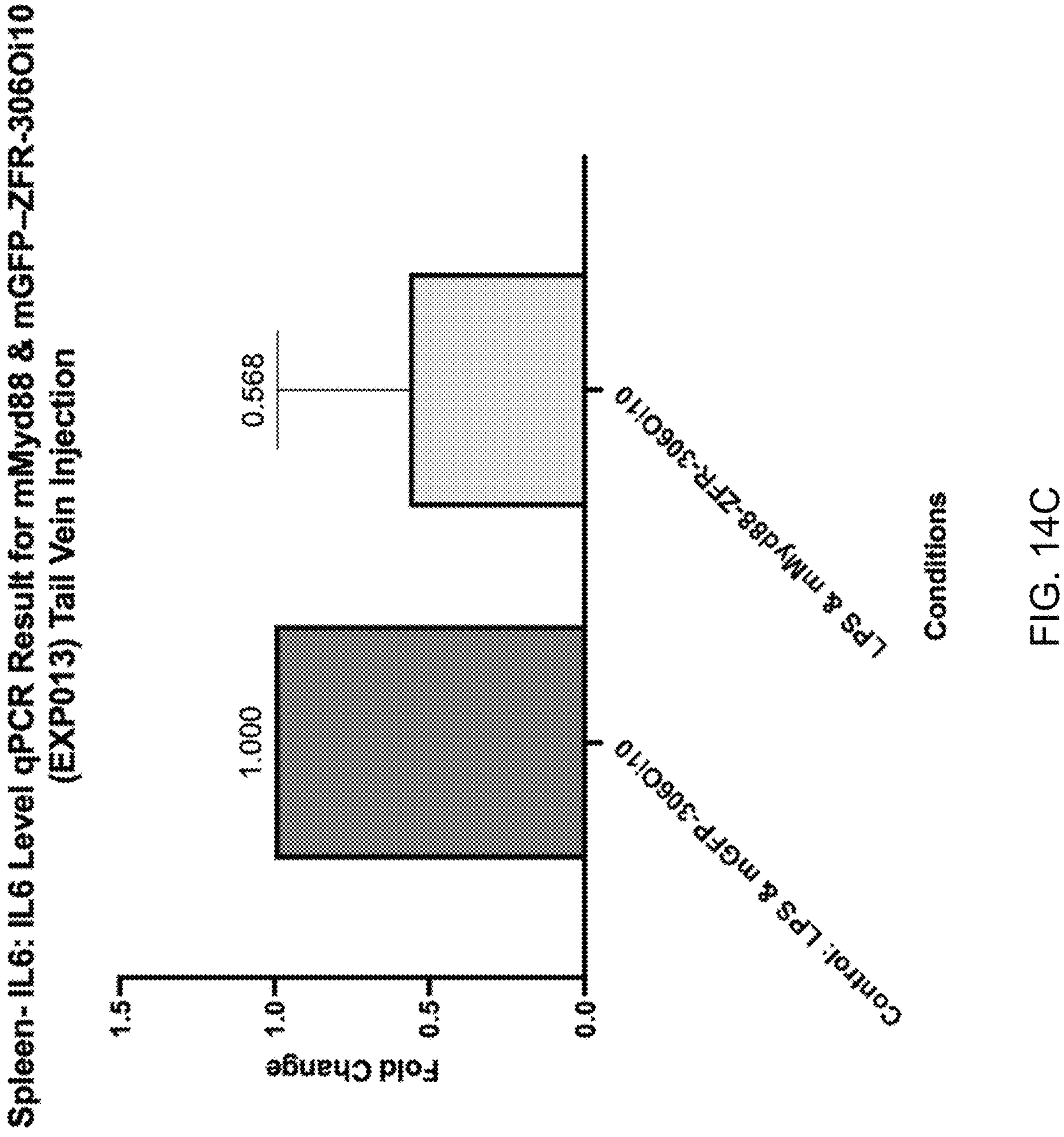
Figure 14D:
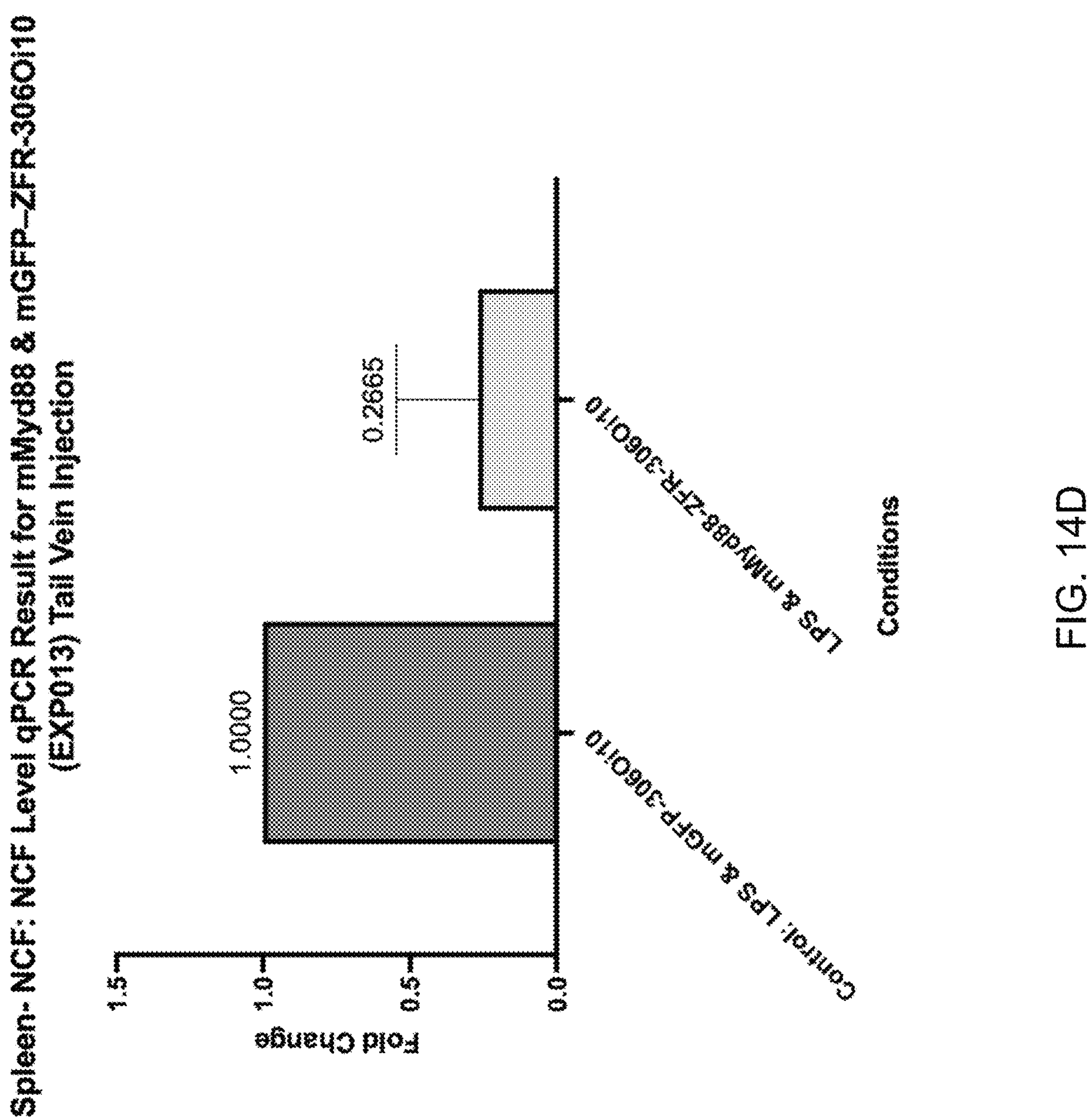
Figure 14E:
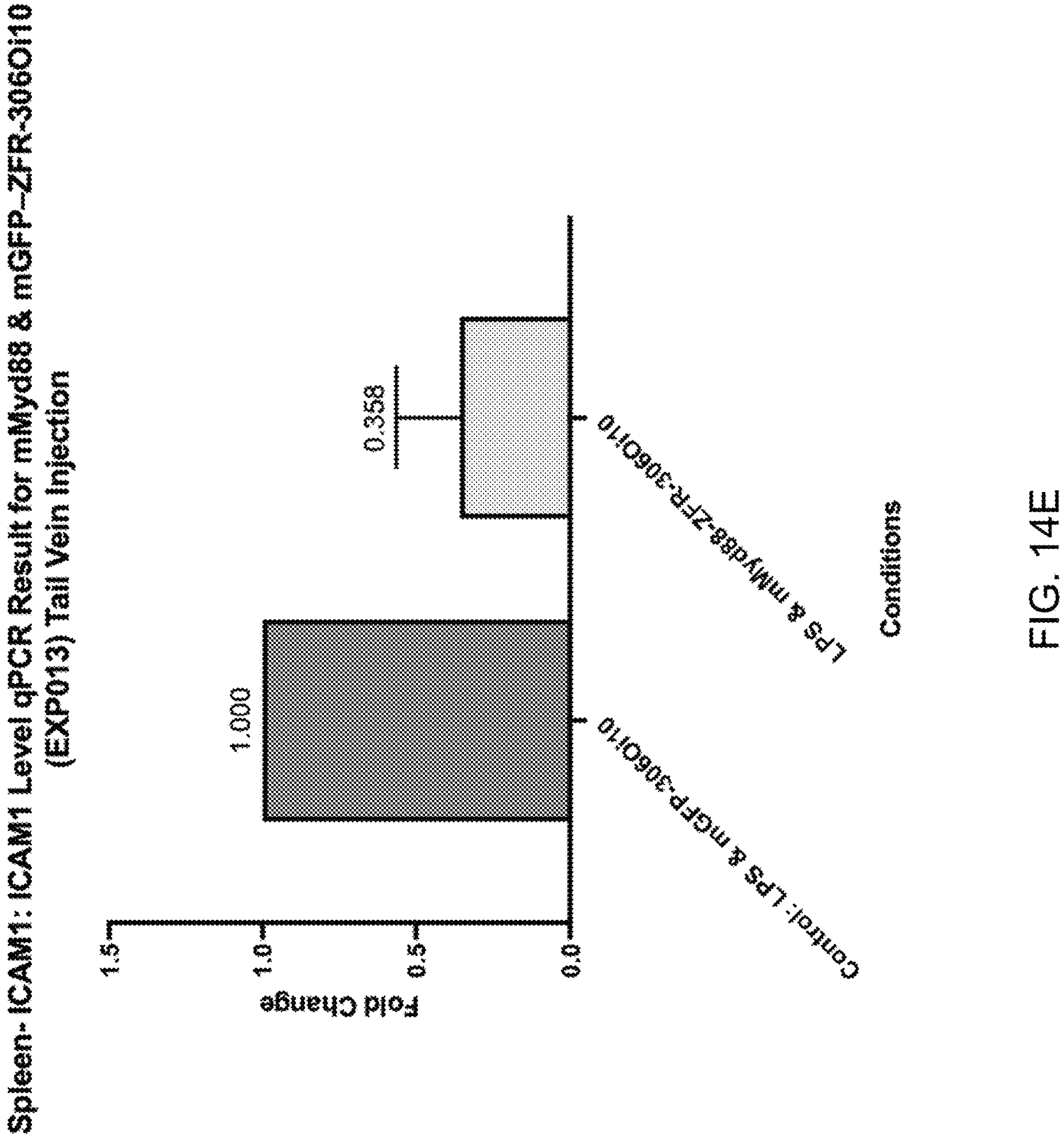
Figure 14F:
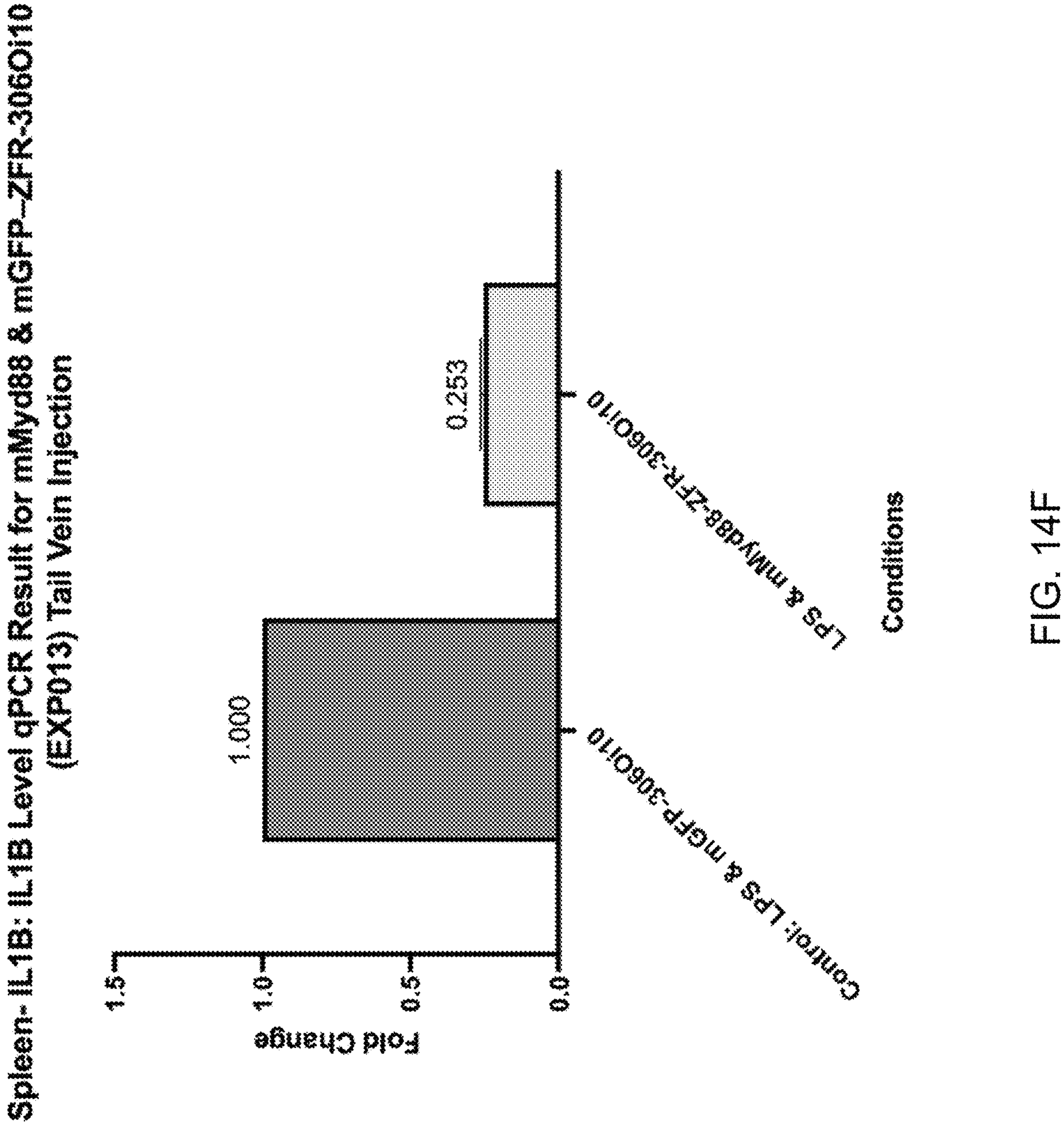
Figure 15A:
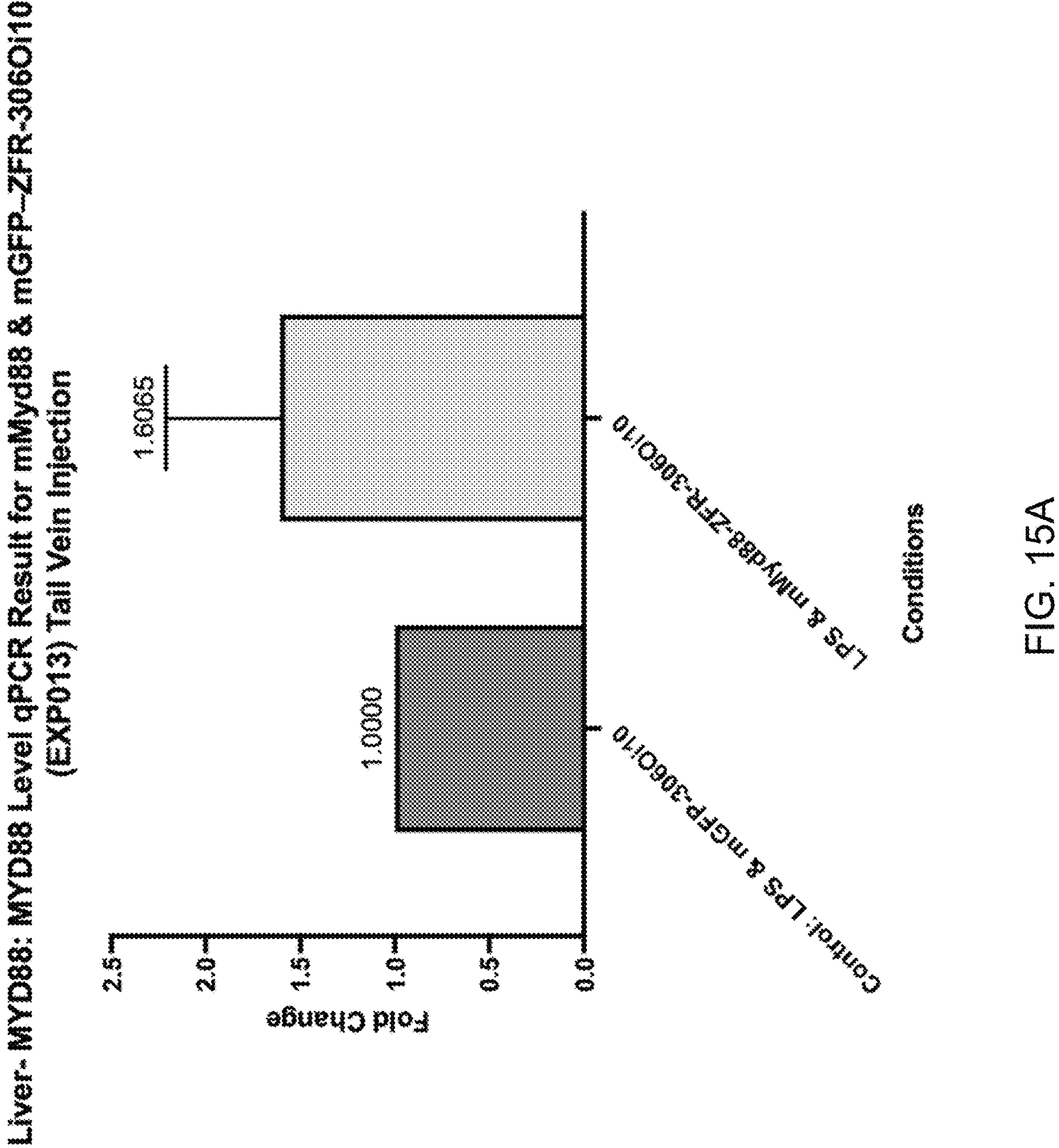
Figure 15B:
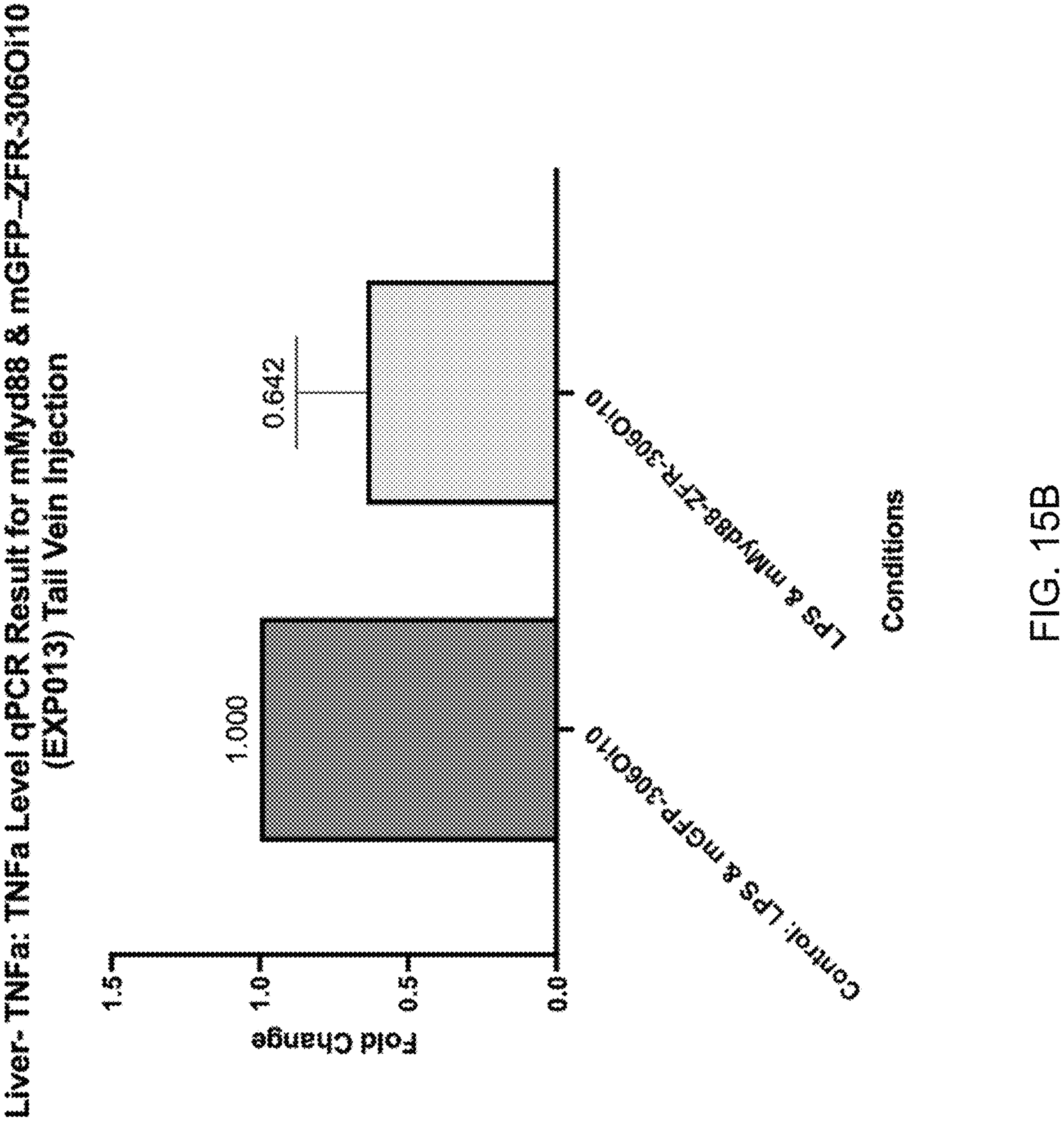
Figure 15C:
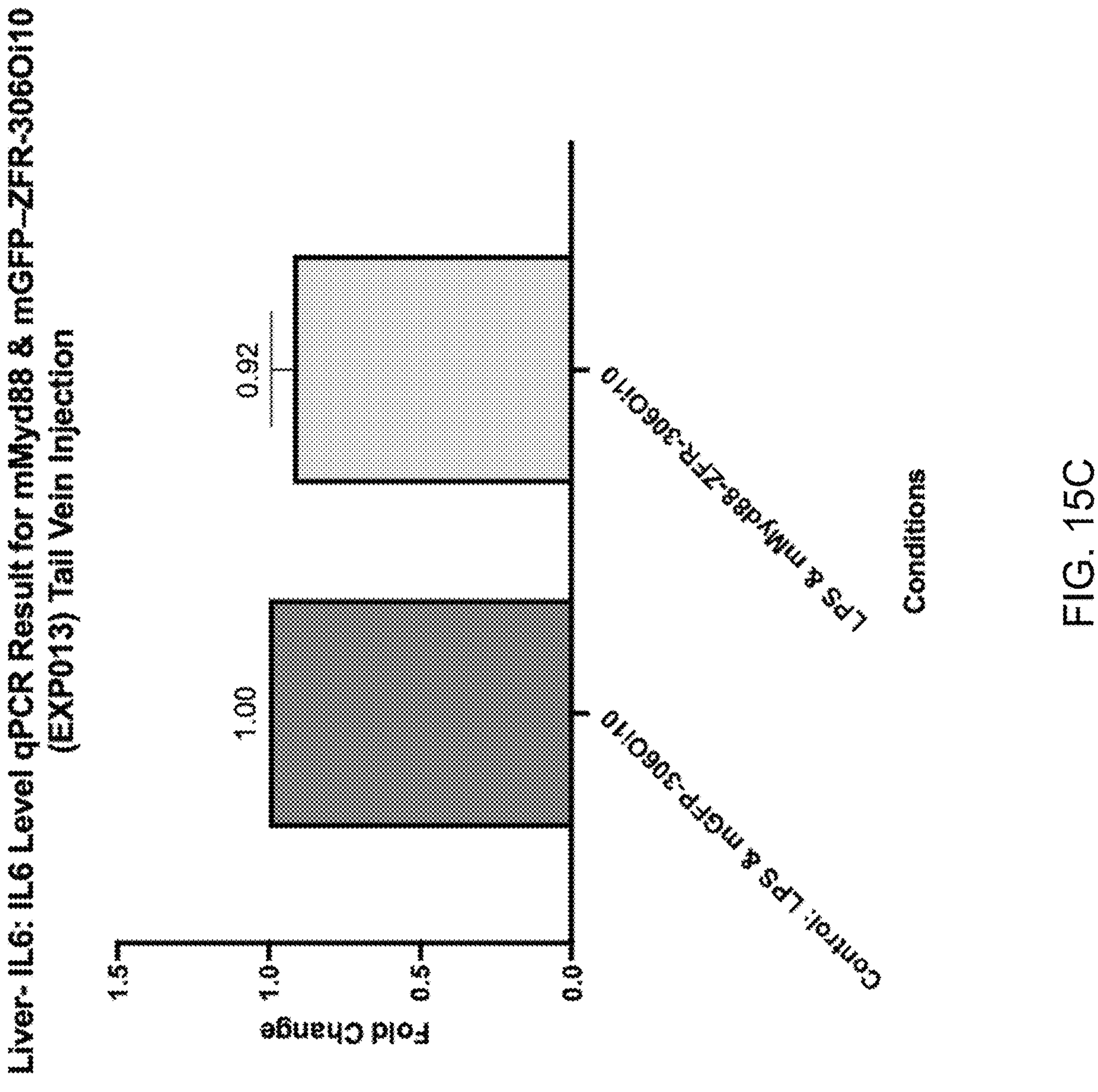
Figure 15D:
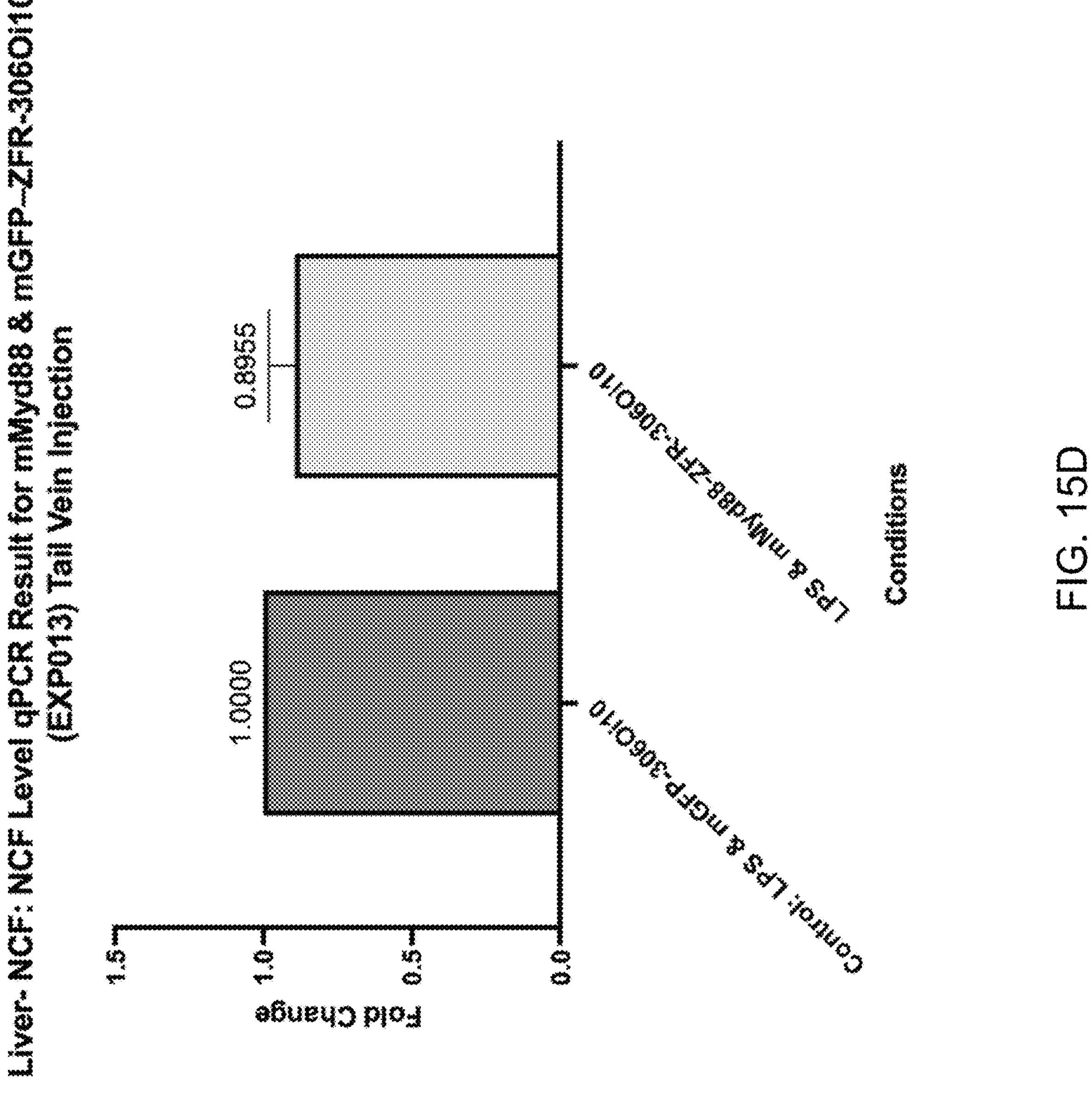
Figure 15E:
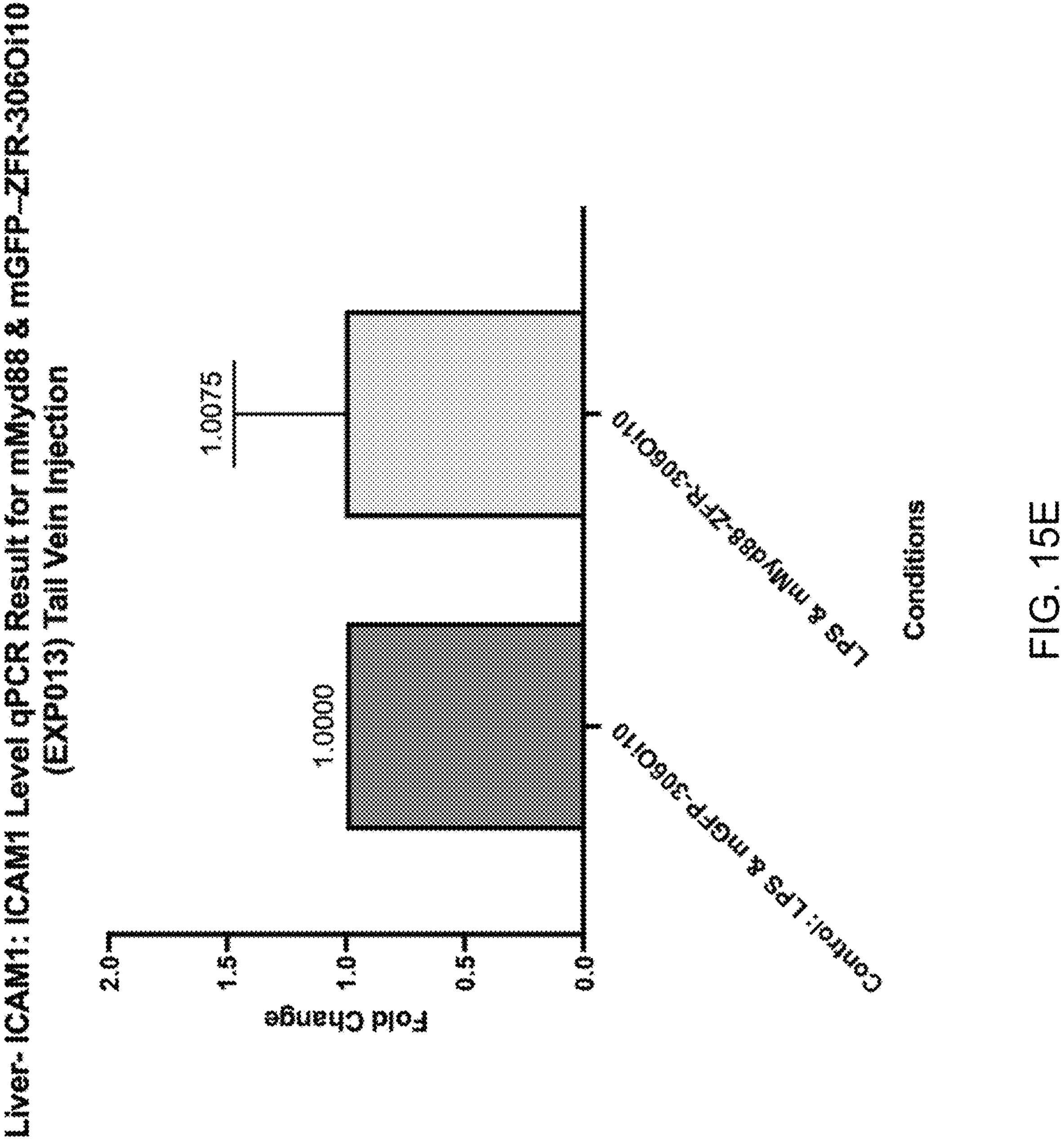
Figure 15F:
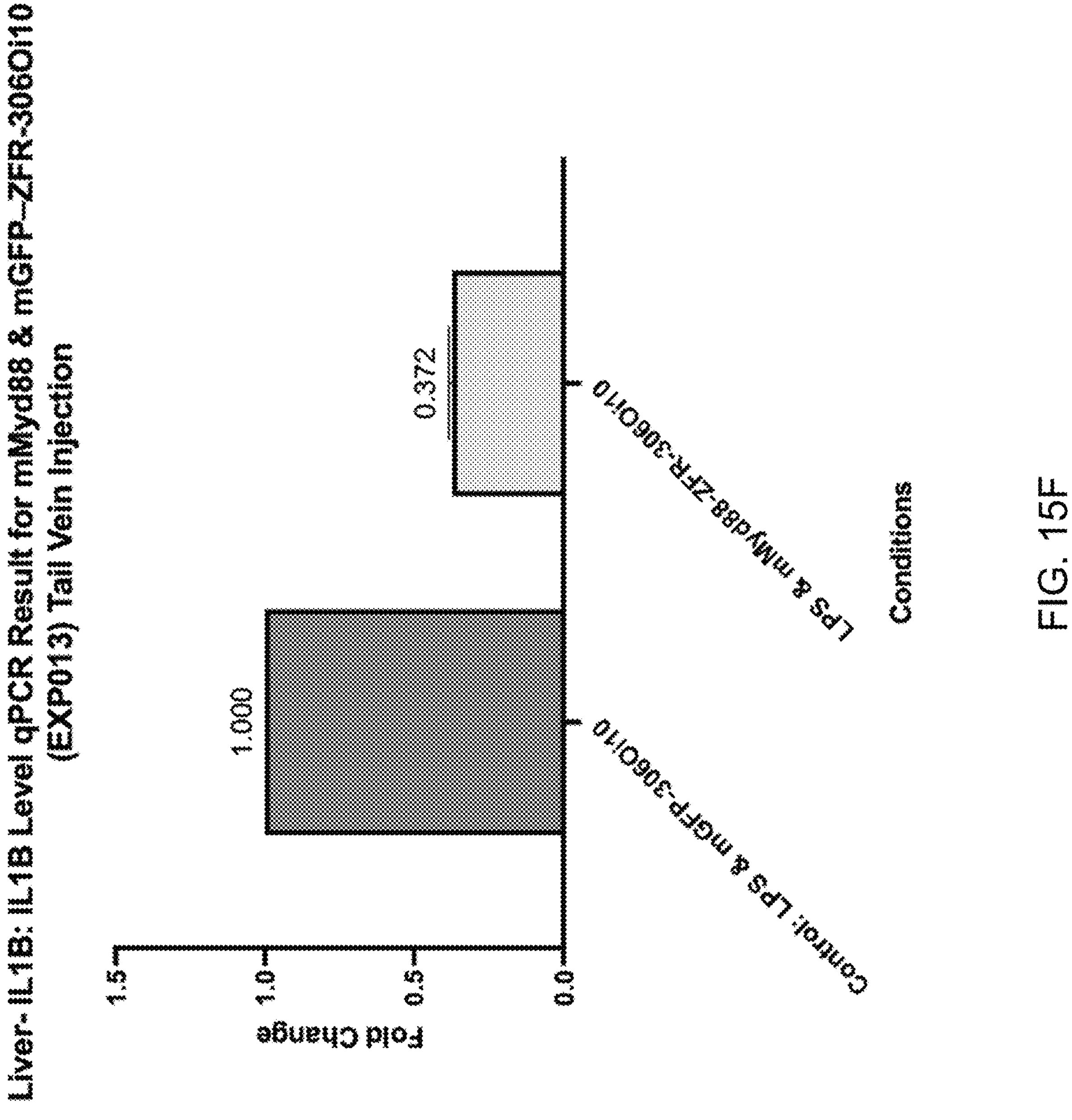

FIGS. 12A-12B are graphs showing the fold change in MYD88 transcript levels (as measured by qPCR) in mice treated with LPS and either (i) mGFP-306$O_{10}$ or (ii) mMYD88-ZFR-306$O_{10}$ in liver (A) and blood (B).

FIGS. 13A-13D are graphs showing the levels of TNF alpha (A and C) and IL-6 (B and D) in mice treated with LPS and either (i) mGFP-306$O_{10}$ or (ii) mMYD88-ZFR-306$O_{10}$ in liver (B and C) and blood (A and D).

FIGS. 14A-14F are graphs showing the fold change in MYD88 (A), TNF alpha (B), IL-6 (C), NCF (D), ICAM1 (E), and IL-1B (F) transcript levels (as measured by qPCR) in mice treated with LPS and either (i) mGFP-3060i10 or (ii) mMYD88-ZFR-3060i10 in spleen.

FIGS. 15A-15F are graphs showing the fold change in MYD88 (A), TNF alpha (B), IL-6 (C), NCF (D), ICAM1 (E), and IL-1B (F) transcript levels (as measured by qPCR) in mice treated with LPS and either (i) mGFP-3060i10 or (ii) mMYD88-ZFR-3060i10 in liver.

Figure 16A:
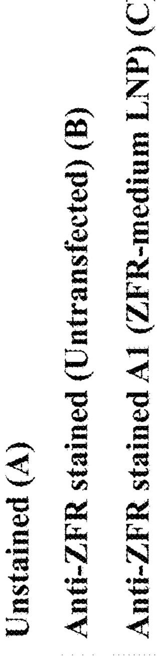
Figure 16A:
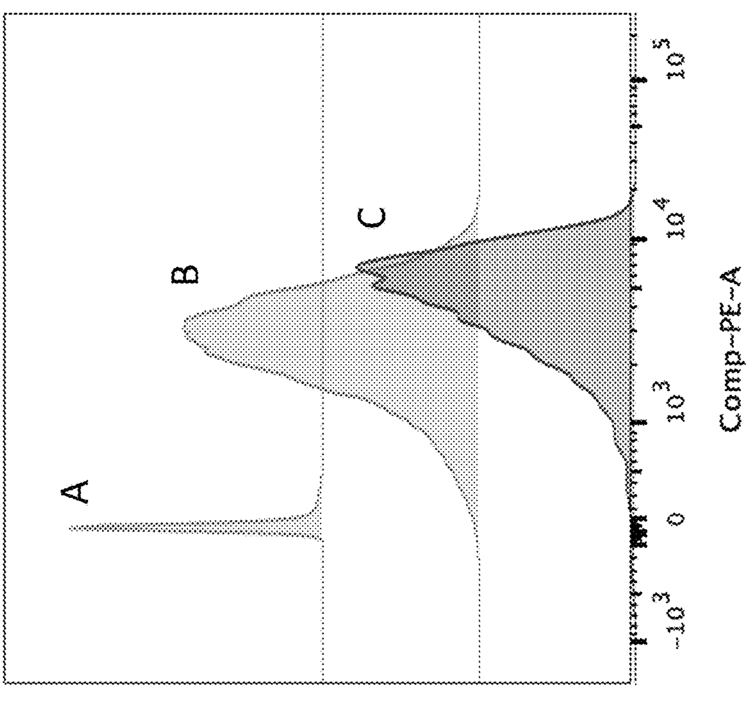
Figure 16B:
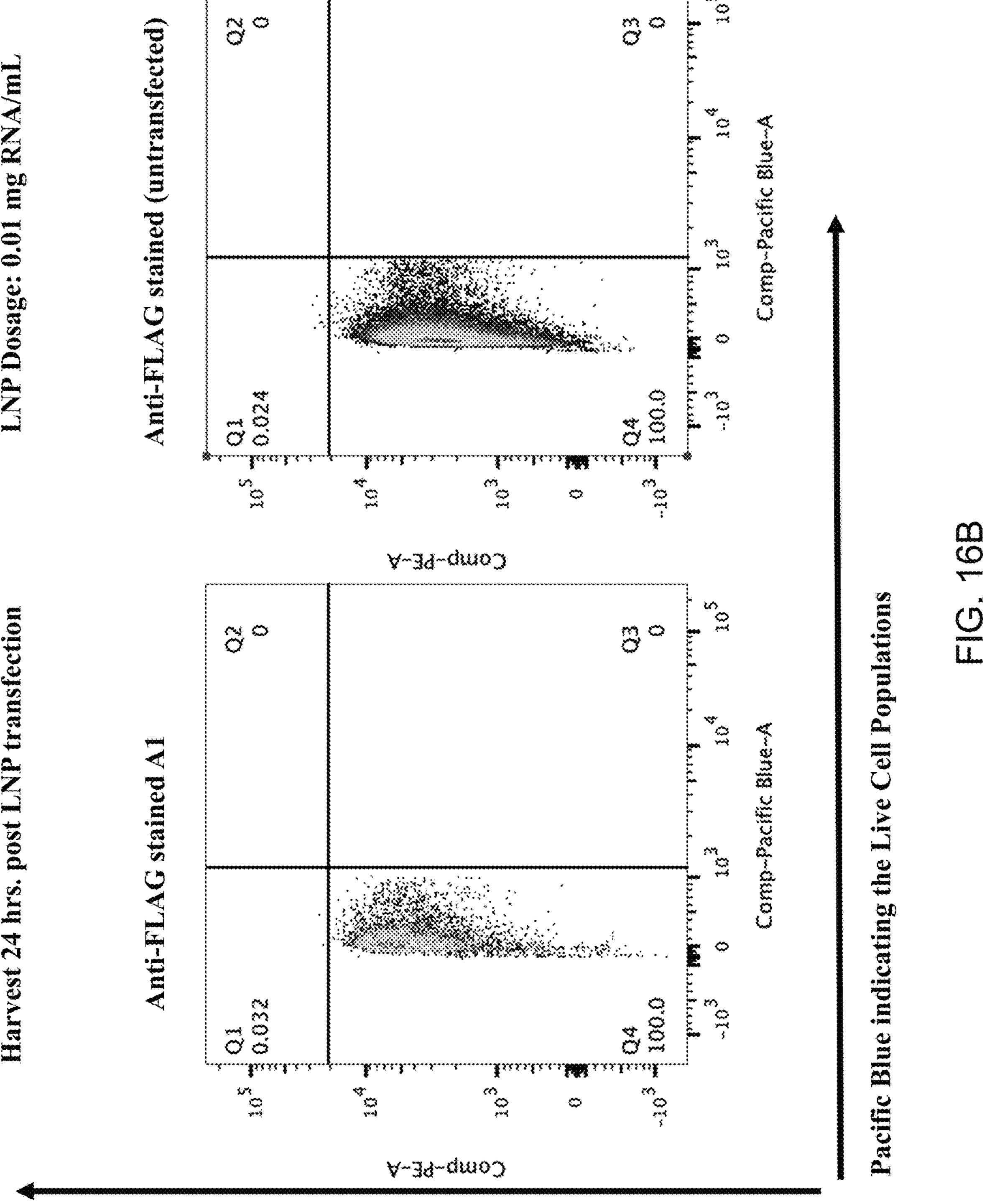

FIGS. 16A-16B show a histogram (A) and dot plots (B) showing the results of FACS analysis of cells that were unstained or stained with PE-conjugated anti-FLAG antibodies for sample A1 of Table 2. Stained cells were untransfected or transfected with mMYD88-ZFR-306$O_{10}$.

Figure 17A:
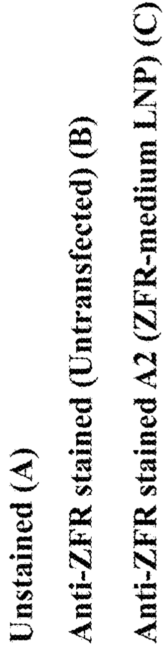
Figure 17A:
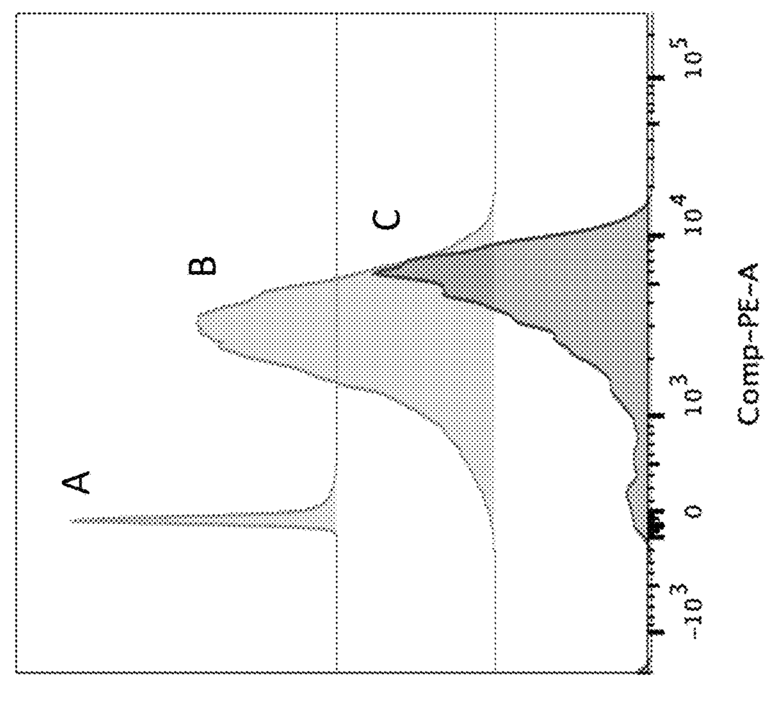
Figure 17B:
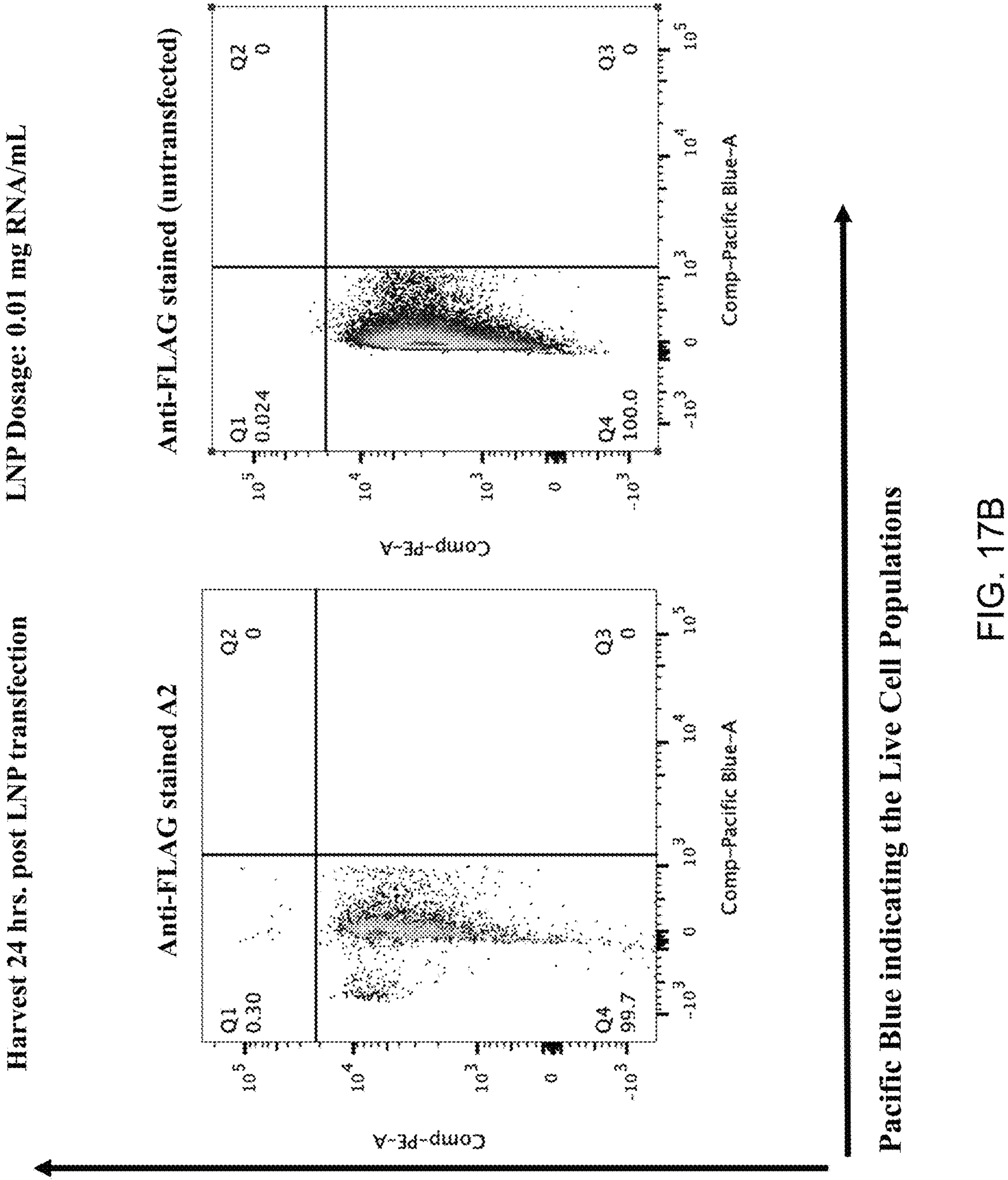

FIGS. 17A-17B show a histogram (A) and dot plots (B) showing the results of FACS analysis of cells that were unstained or stained with PE-conjugated anti-FLAG antibodies for sample A2 of Table 2. Stained cells were untransfected or transfected with mMYD88-ZFR-306$O_{10}$.

Figure 18A:
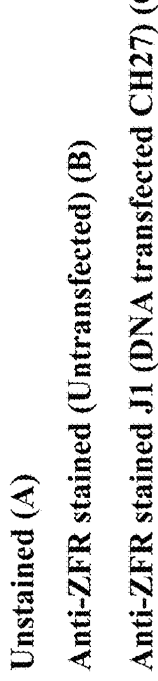
Figure 18A:
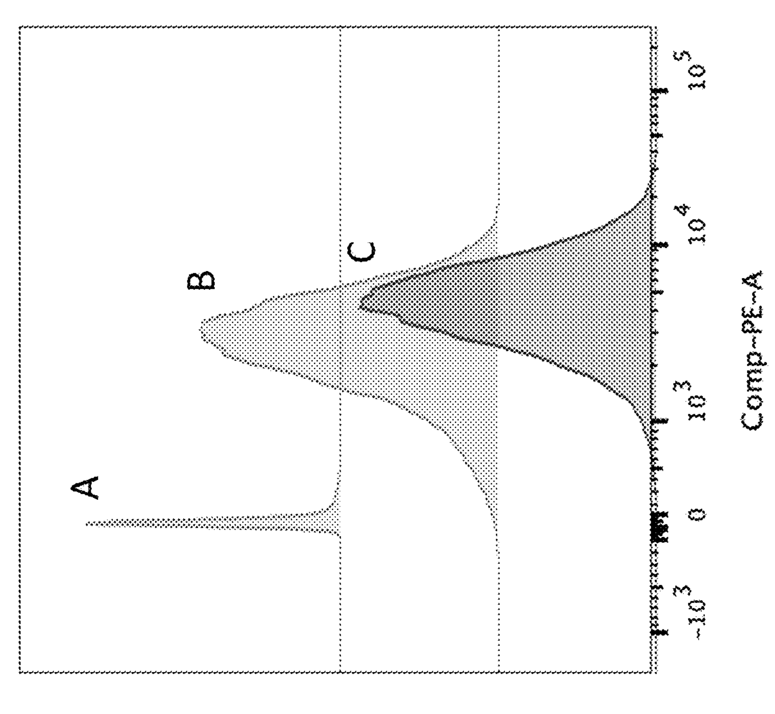
Figure 18B:
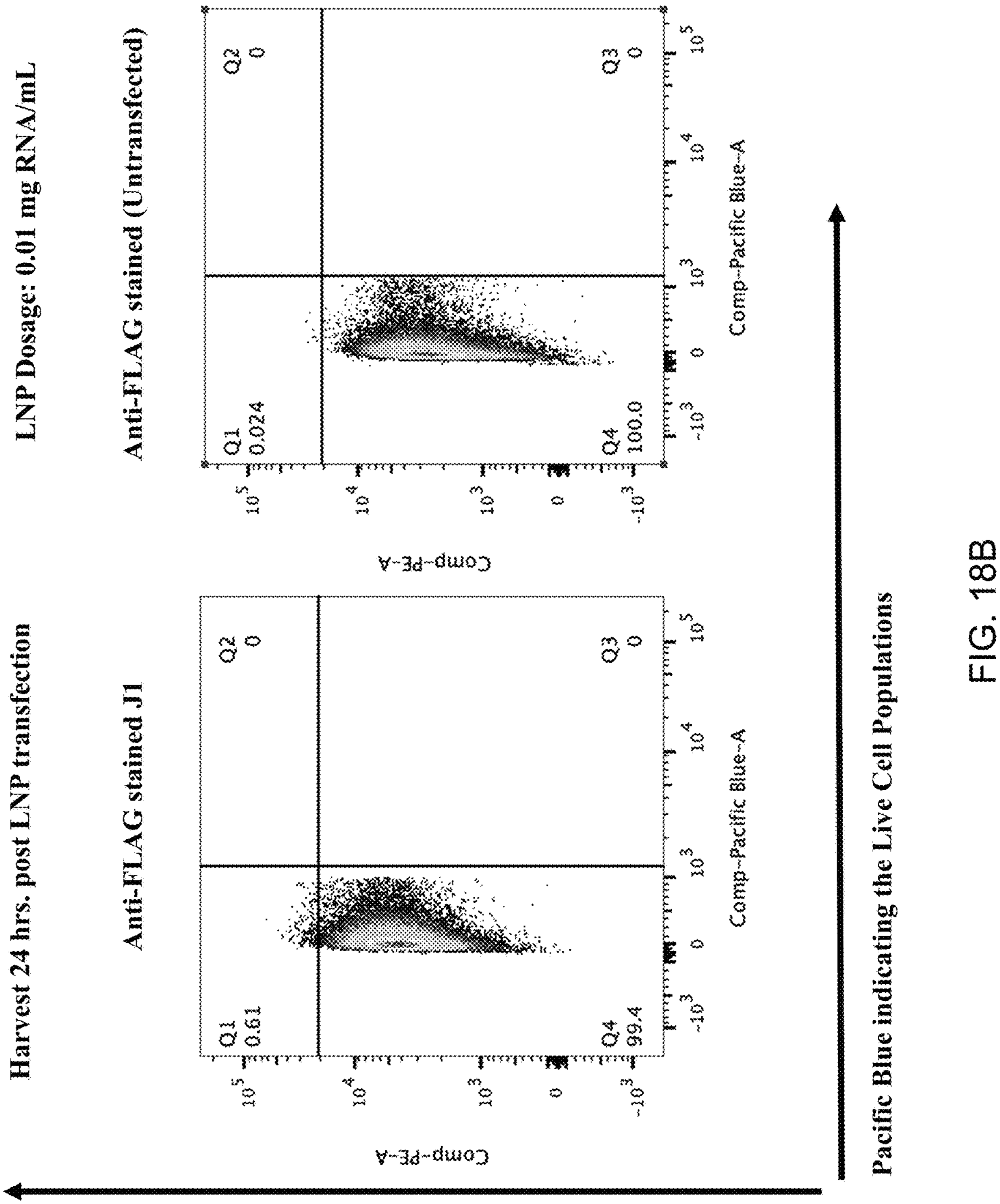

FIGS. 18A-18B show a histogram (A) and dot plots (B) showing the results of FACS analysis of cells that were unstained or stained with PE-conjugated anti-FLAG antibodies for sample J1 of Table 2. Stained cells were untransfected or transfected with DNA plasmid.

Figure 19A:
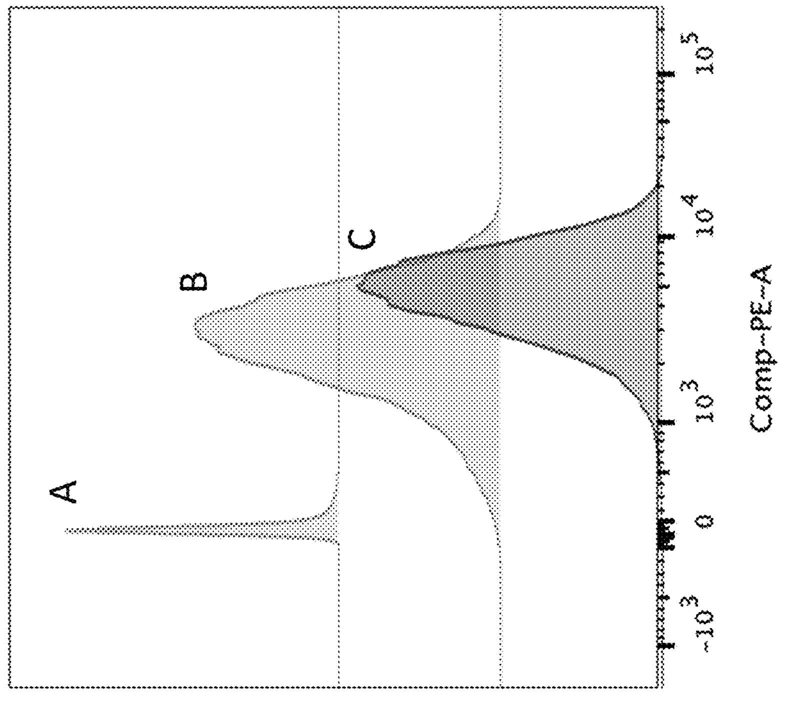
Figure 19B:
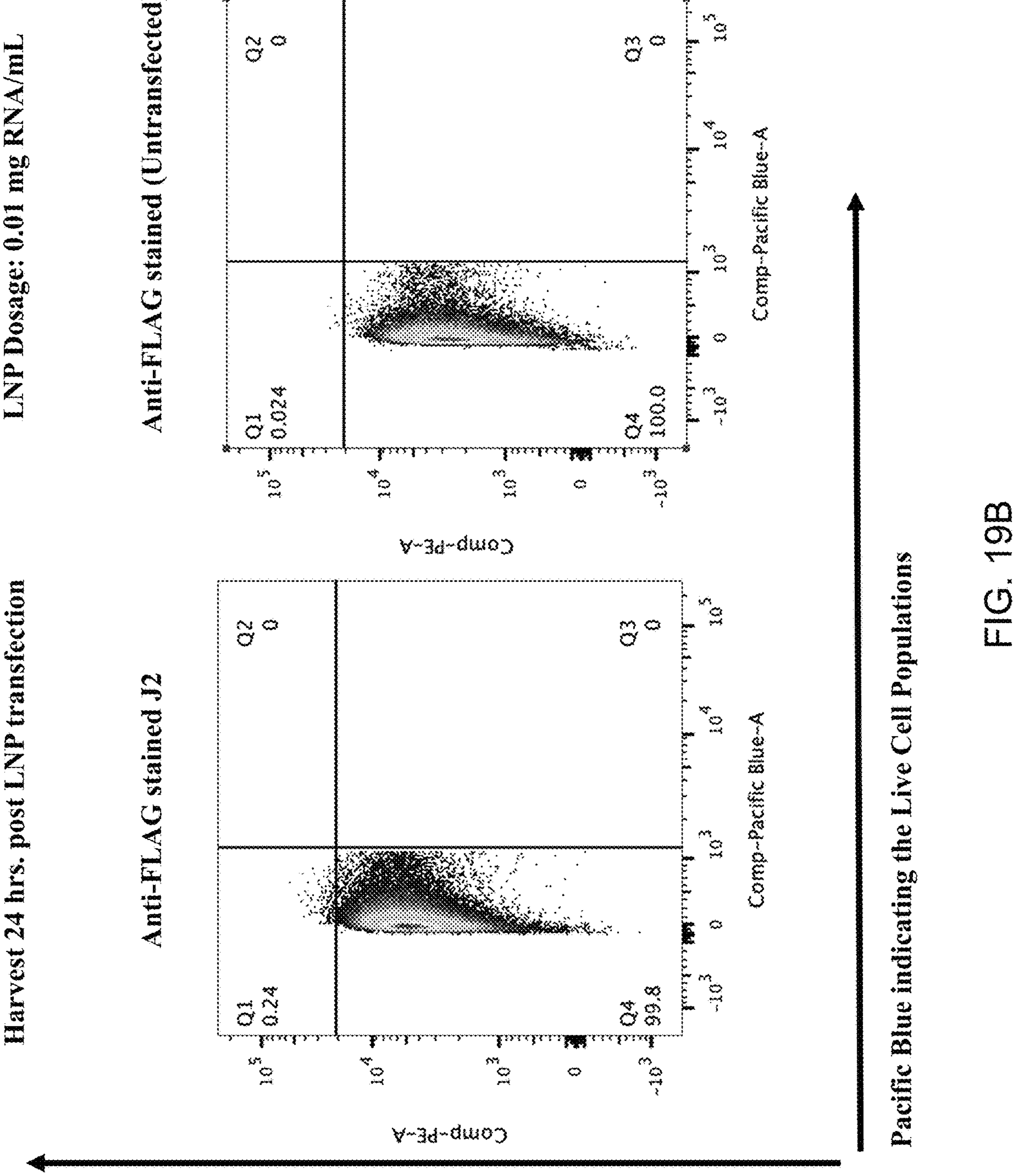

FIGS. 19A-19B show a histogram (A) and dot plots (B) showing the results of FACS analysis of cells that were unstained or stained with PE-conjugated anti-FLAG antibodies for sample J2 of Table 2. Stained cells were untransfected or transfected with DNA plasmid.

Figure 20:
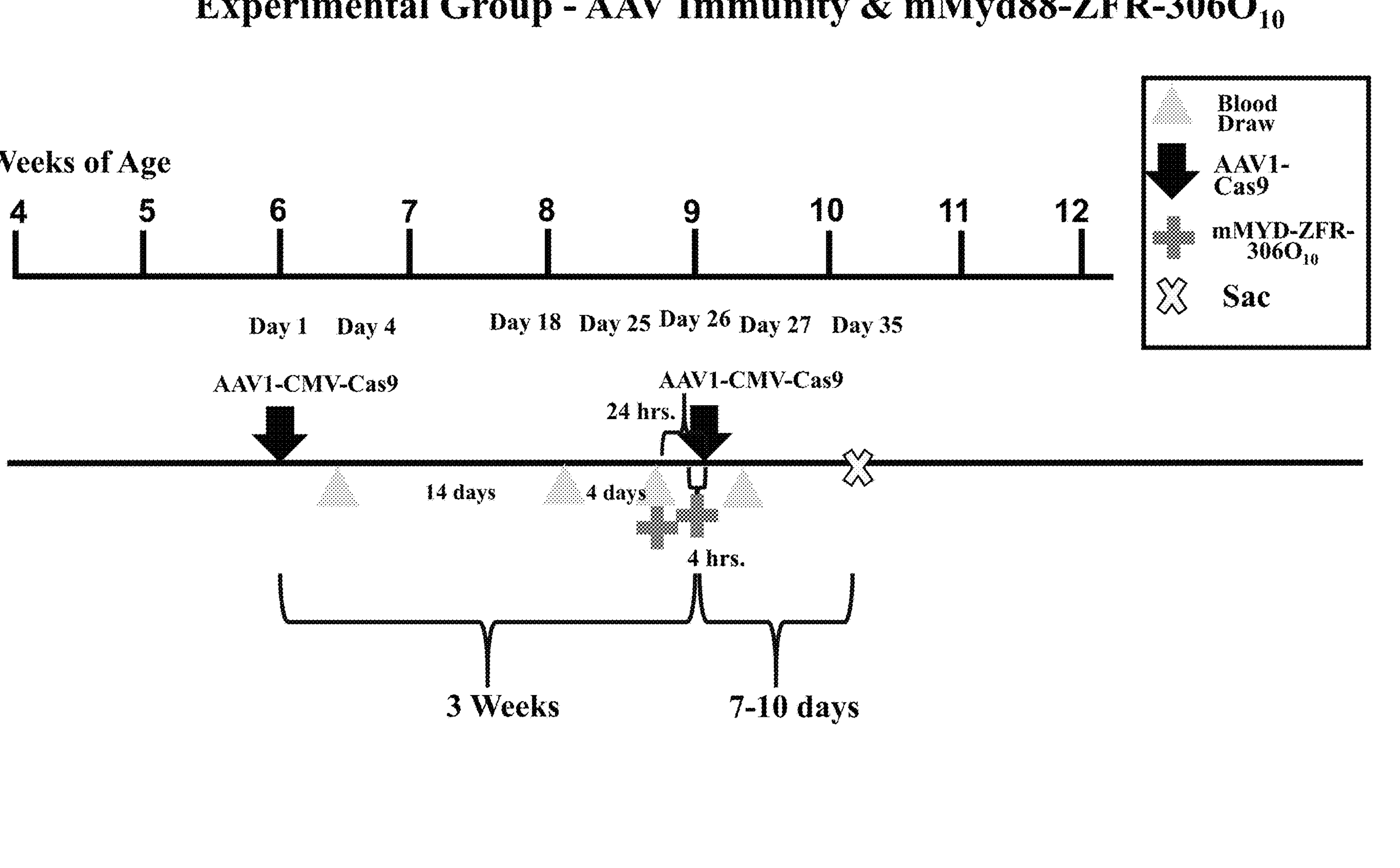

FIG. 20 is a schematic illustrating the time points at which mice were administered (i) LNP including an AAV1-CMV-Cas9 vector and (ii) mMYD88-ZFR-306$O_{10}$ (IP) and blood was drawn from the mice. LNP dosage is 0.75 mg/kg. “Sac” indicates when mice were sacrificed.

Figure 21:
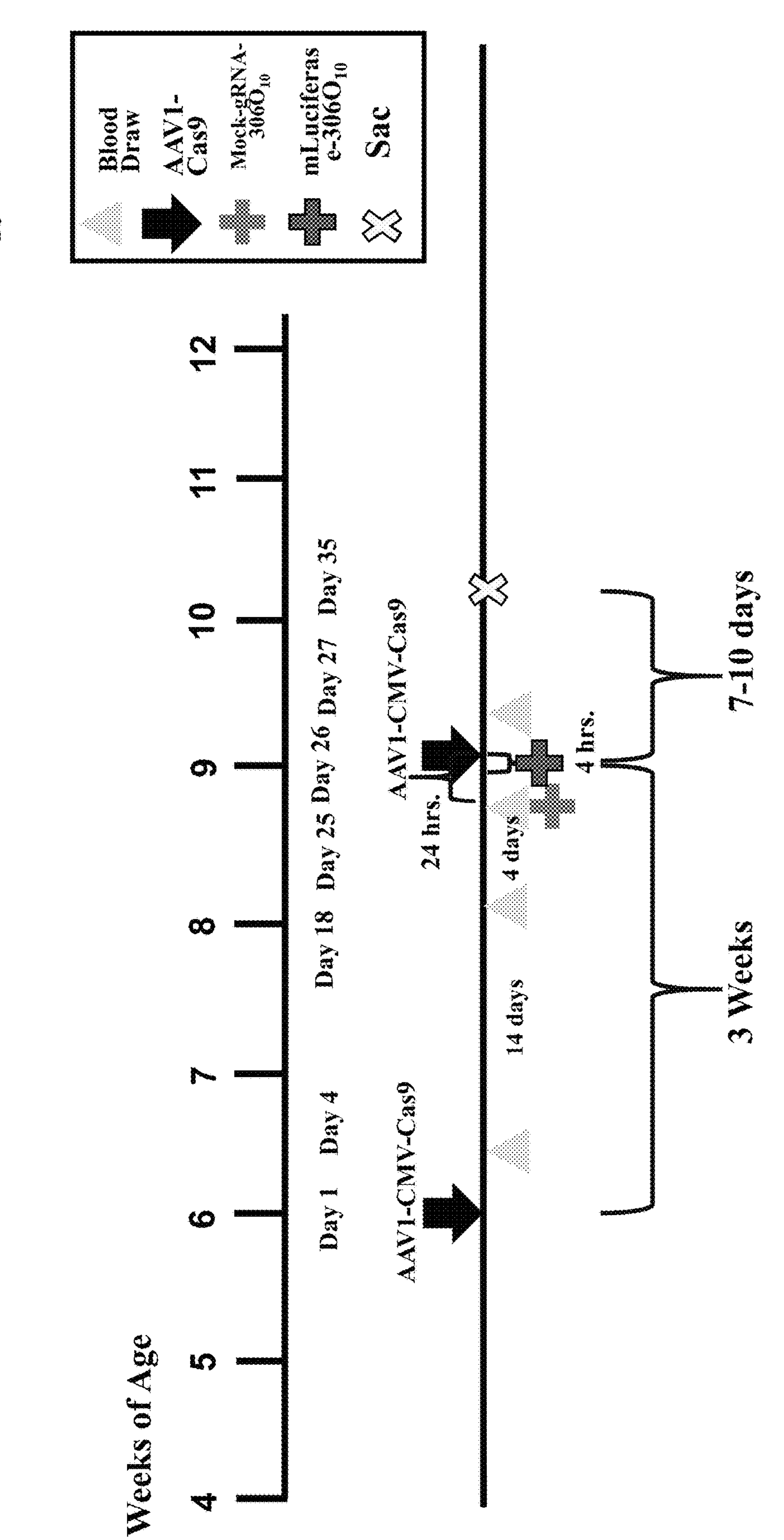

FIG. 21 is a schematic illustrating the time points at which mice were administered (i) LNP including an AAV1-CMV-Cas9 vector, (ii) Mock-gRNA-306$O_{10}$, and (iii) mLuciferase-306$O_{10}$ (IP) and blood was drawn. LNP dosage is 0.75 mg/kg. “Sac” indicates when mice were sacrificed.

Figure 22A:
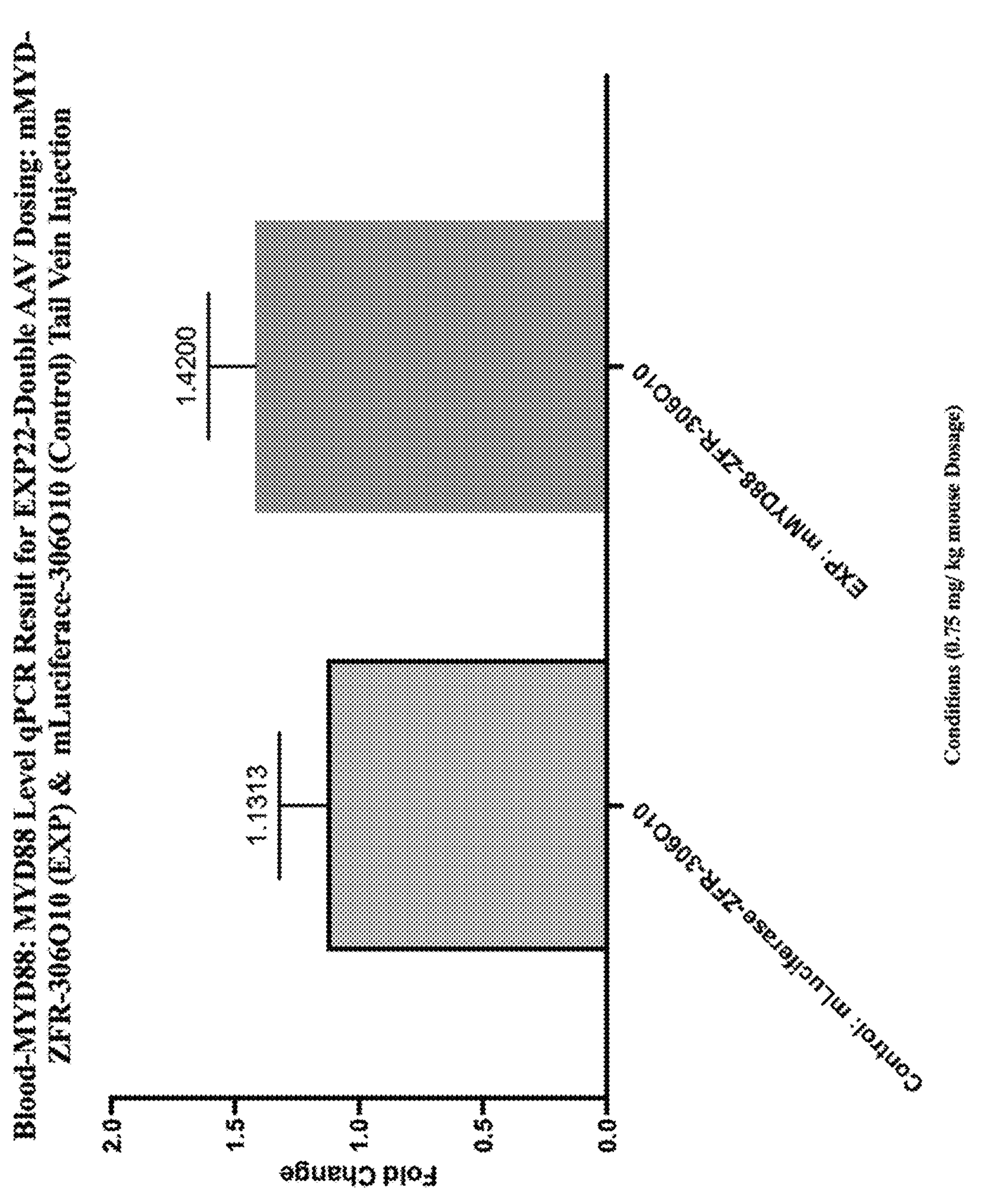
Figure 22B:
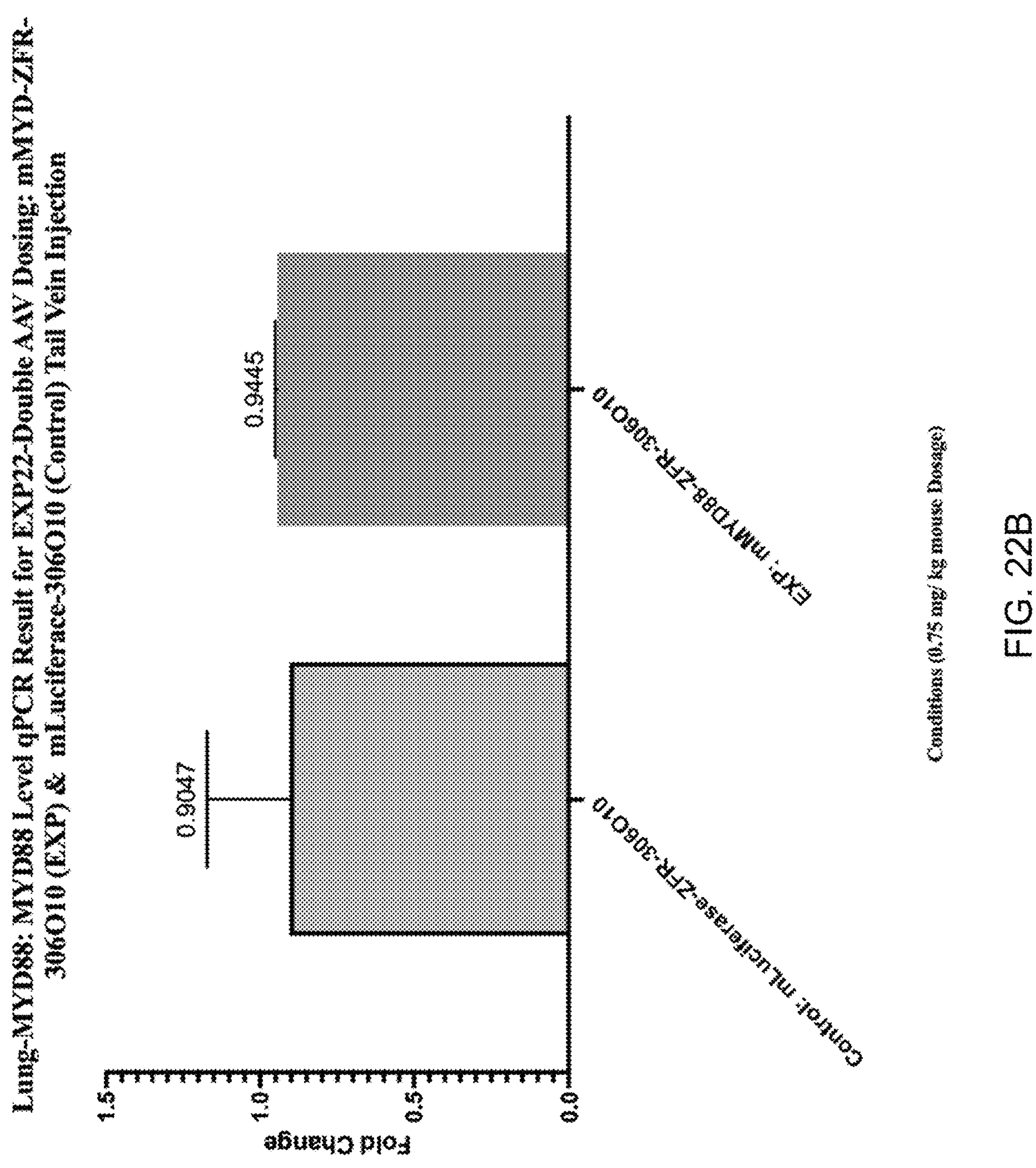

FIGS. 22A-22B are graphs showing the fold change in MYD88 transcript levels (as measured by qPCR) in mice treated with AAV1-CMV-Cas9 vector and either (i) mLuciferase-306$O_{10}$ or (ii) mMYD88-ZFR-306$O_{10}$ in blood (A) and lung (B). LNP dosage is 0.75 mg/kg.

Figure 23A:
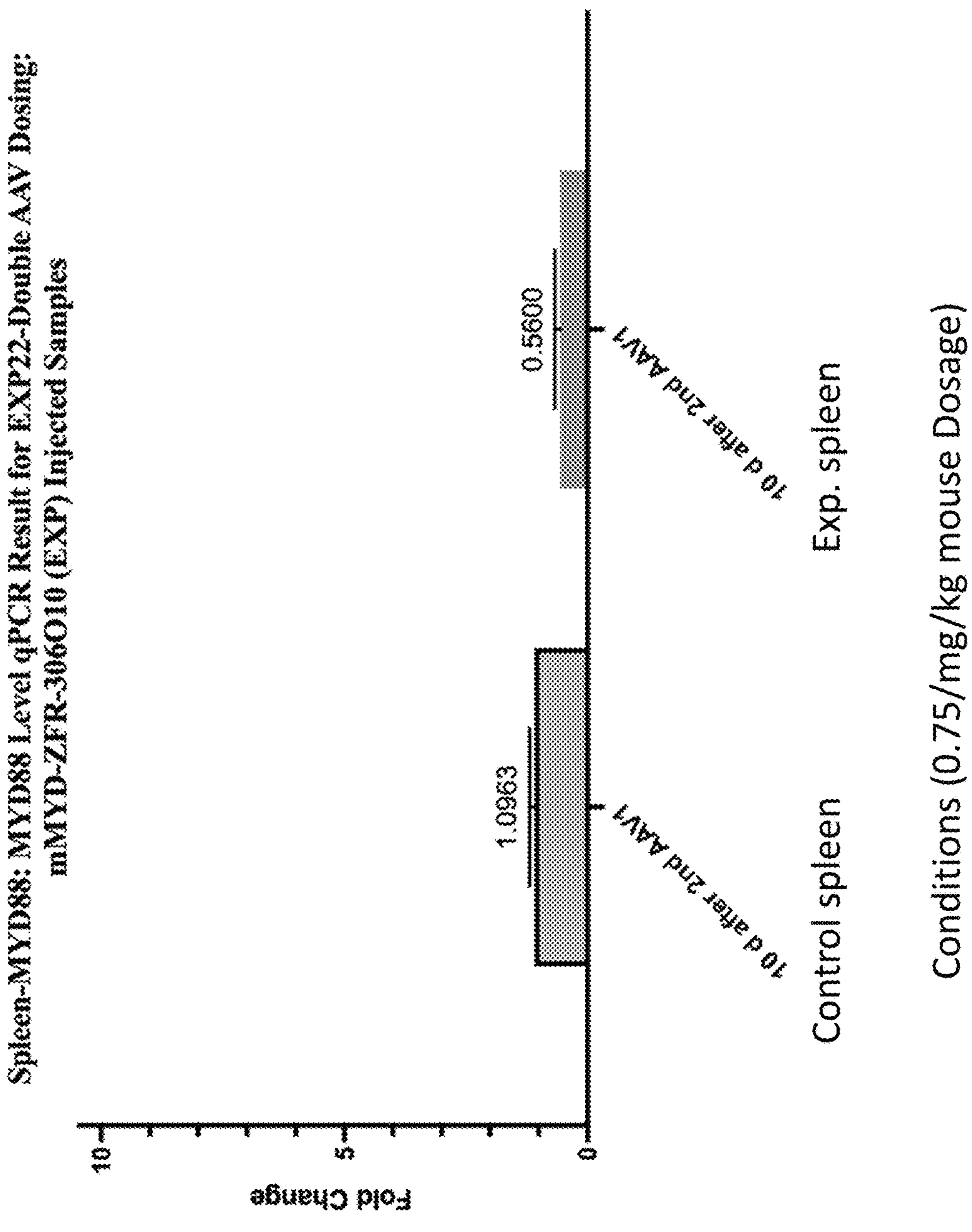
Figure 23B:
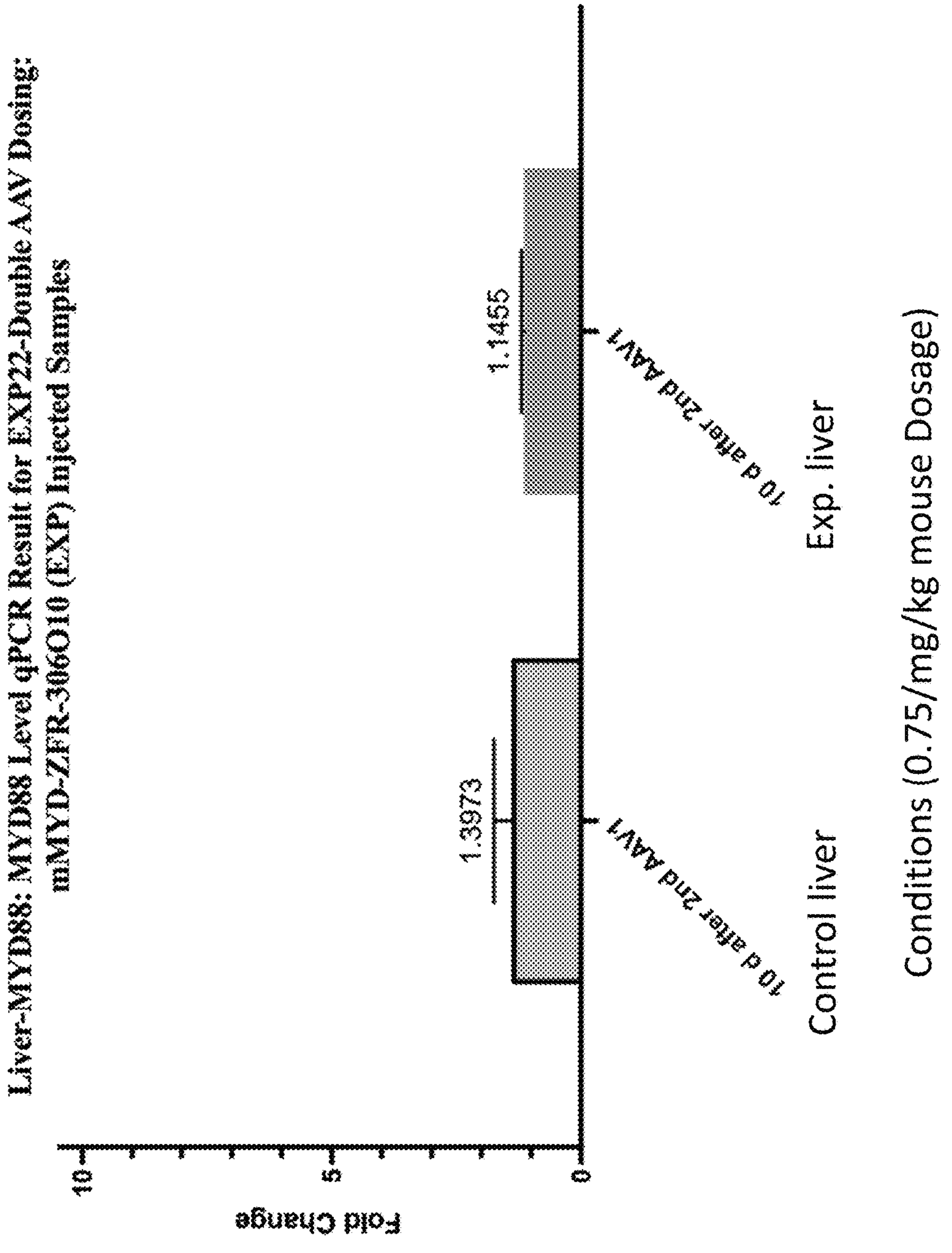

FIGS. 23A-23B are graphs showing the fold change in MYD88 transcript levels (as measured by qPCR) in mice treated with AAV1-CMV-Cas9 vector and either (i) mLuciferase-306$O_{10}$ or (ii) mMYD88-ZFR-306$O_{10}$ in spleen (A) and liver (B). LNP dosage is 0.75 mg/kg.

Figure 24:
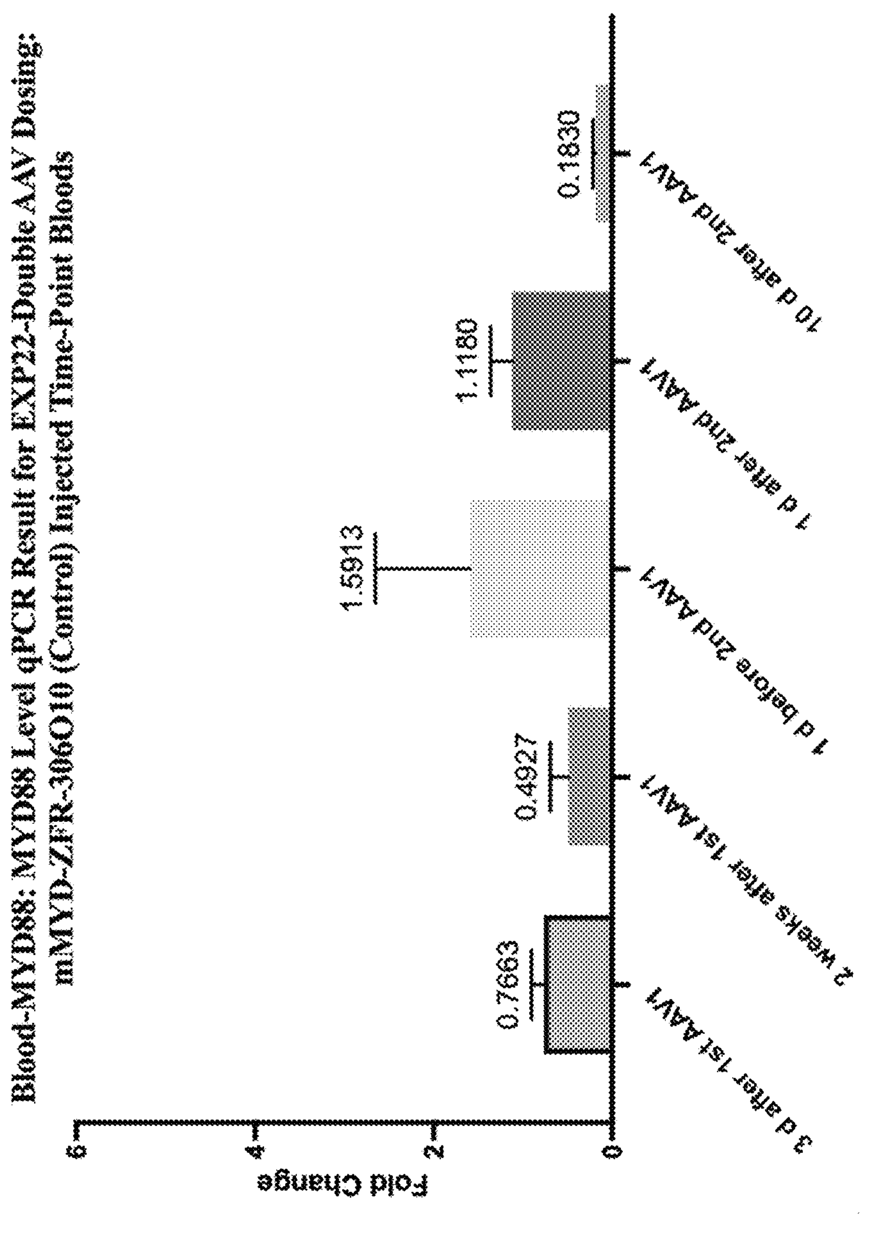

FIG. 24 is a graph showing the fold change in MYD88 transcript levels (as measured by qPCR) in mice treated with AAV1-CMV-Cas9 vector and Mock-gRNA-306$O_{10}$ LNP in blood at various time points before and after AAV1 vector administration. LNP dosage is 0.75 mg/kg.

Figure 25:
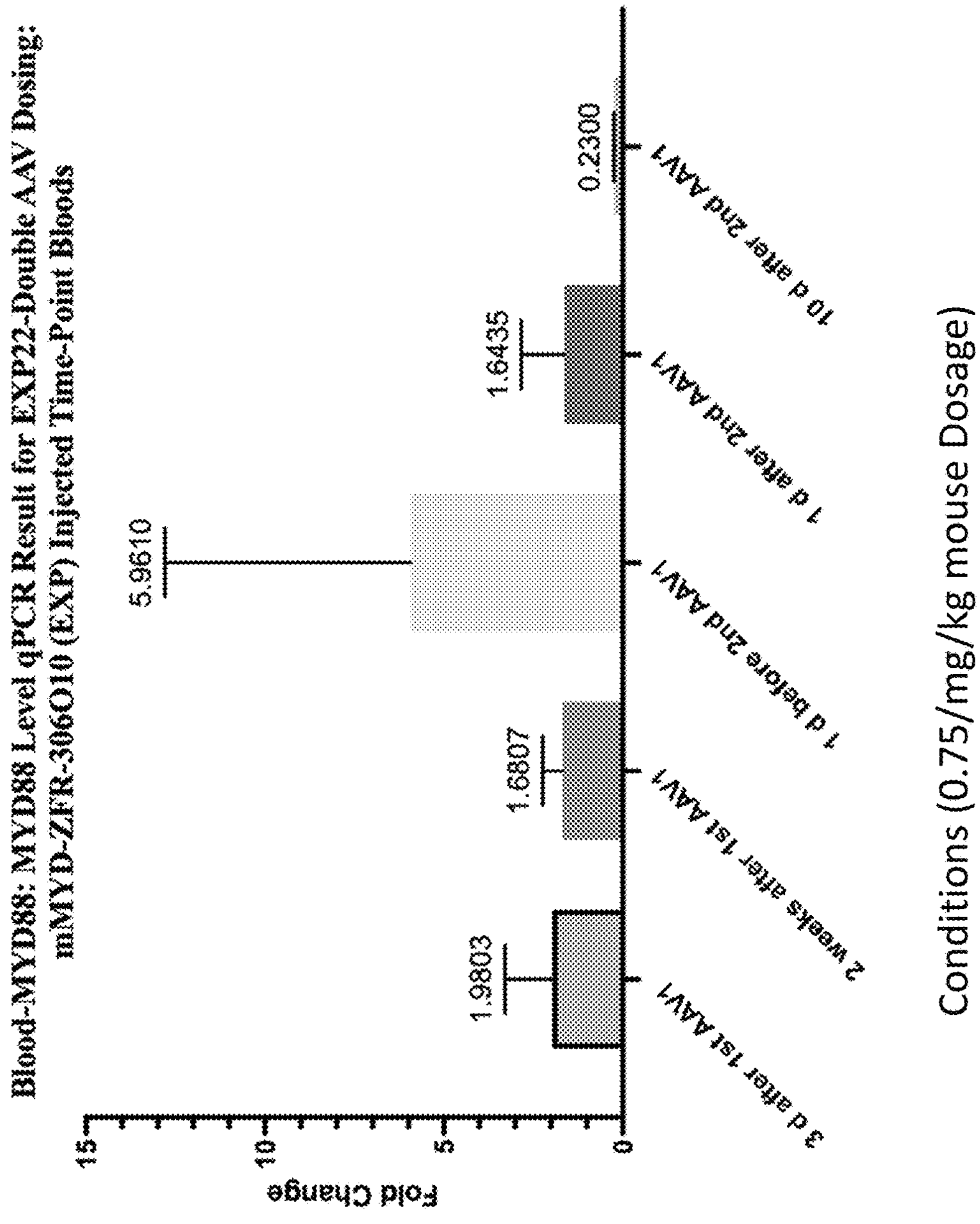

FIG. 25 is a graph showing the fold change in MYD88 transcript levels (as measured by qPCR) in mice treated with AAV1-CMV-Cas9 vector and mMYD88-ZFR-306$O_{10}$ LNP in blood at various time points before and after AAV1 vector administration. LNP dosage is 0.75 mg/kg.

Figure 26:
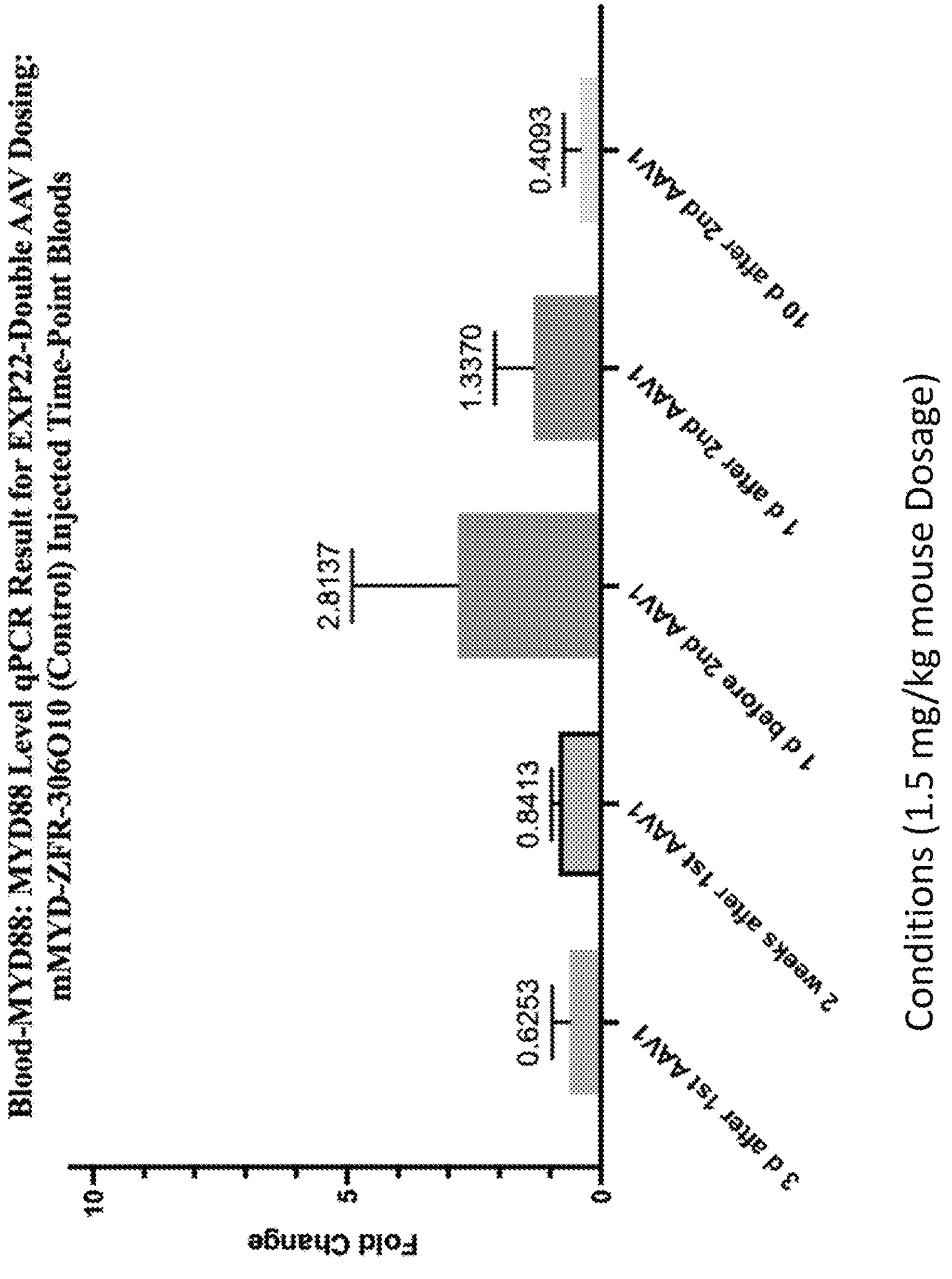

FIG. 26 is a graph showing the fold change in MYD88 transcript levels (as measured by qPCR) in mice treated with AAV1-CMV-Cas9 vector and Mock-gRNA-306$O_{10}$ LNP in blood at various time points before and after AAV1 vector administration. LNP dosage is 1.5 mg/kg.

Figure 27:
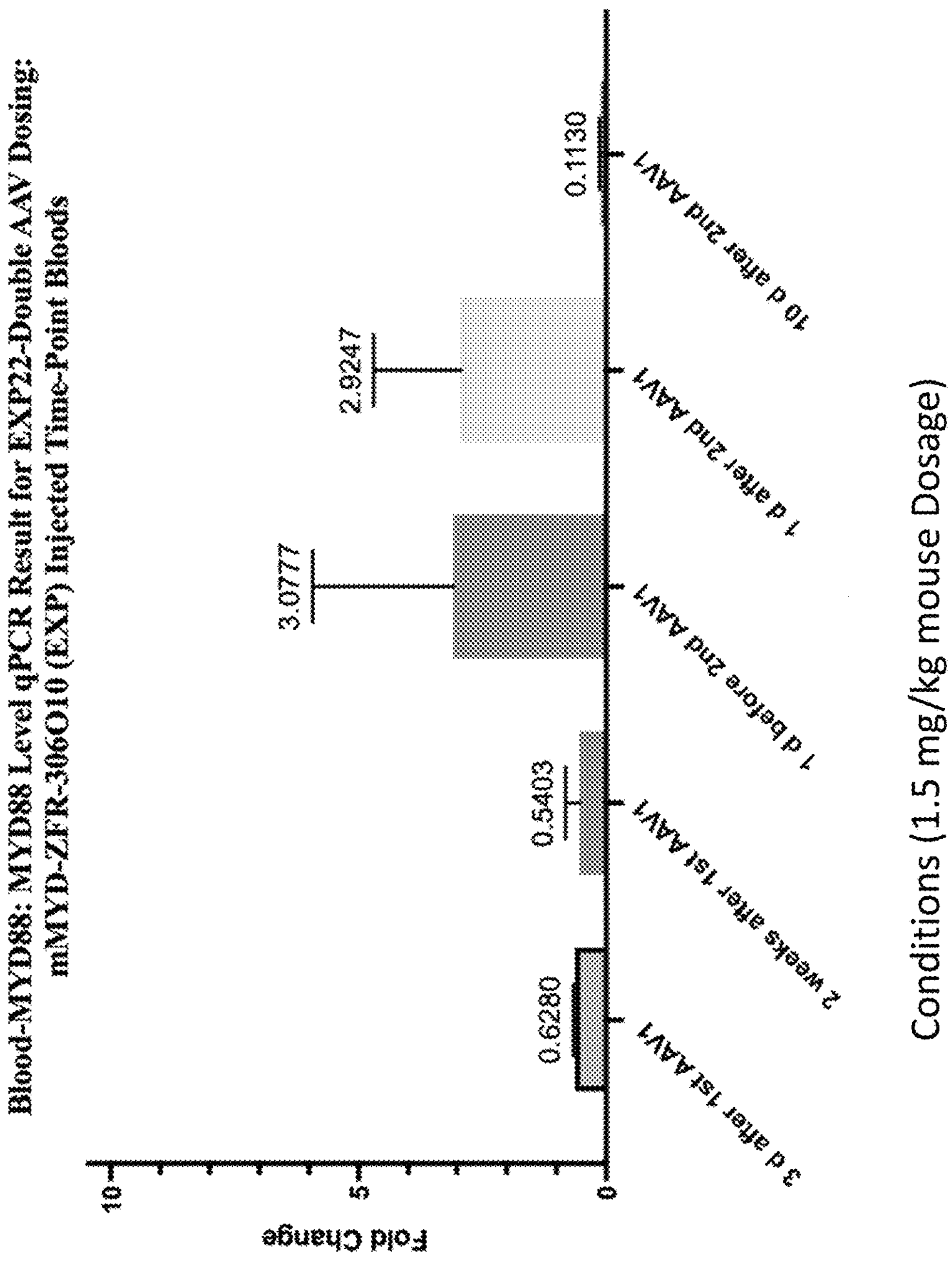

FIG. 27 is a graph showing the fold change in MYD88 transcript levels (as measured by qPCR) in mice treated with AAV1-CMV-Cas9 vector and mMYD88-ZFR-306$O_{10}$ LNP in blood at various time points before and after AAV1 vector administration. LNP dosage is 1.5 mg/kg.

Figure 28:
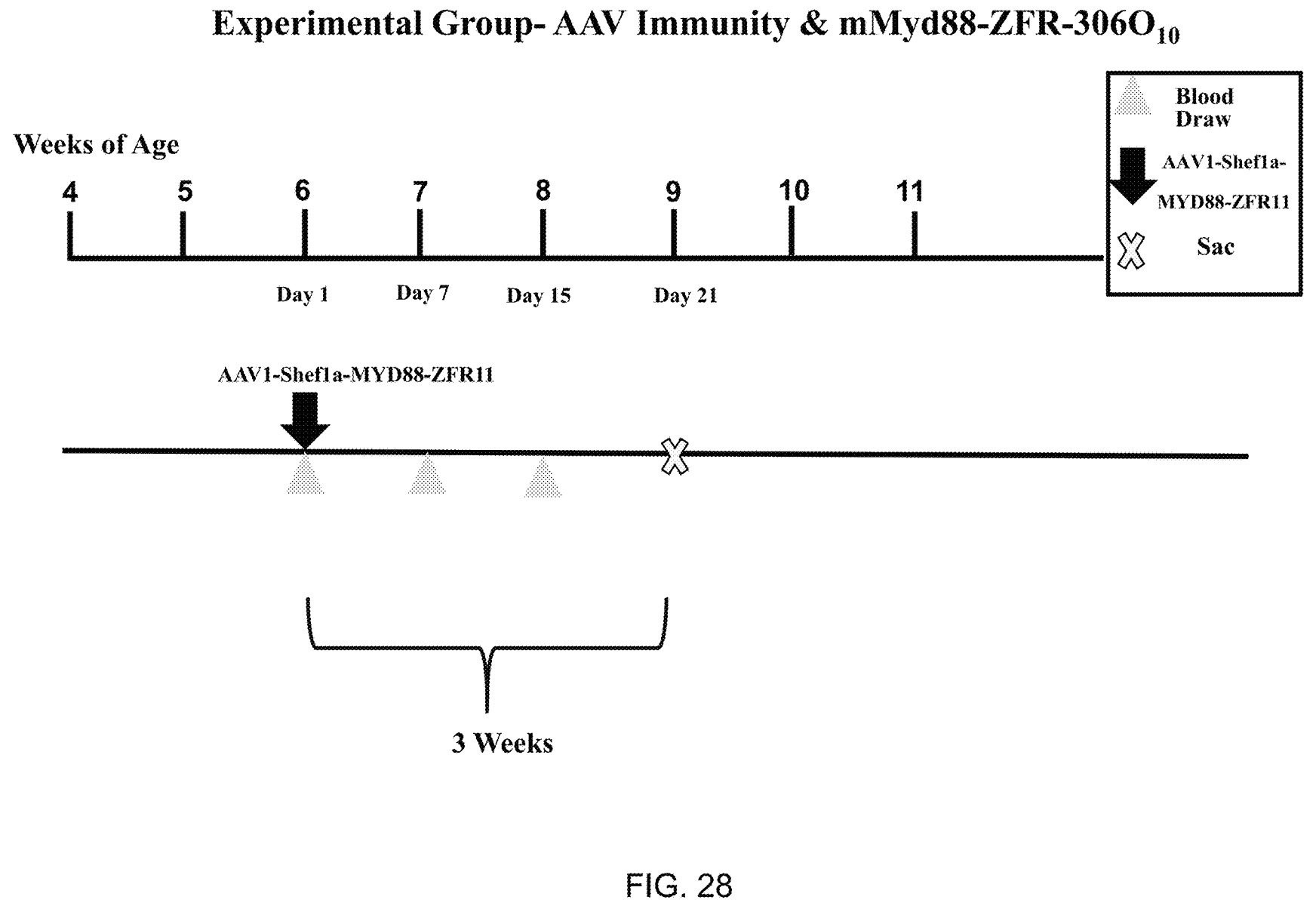

FIG. 28 is a schematic illustrating the time points at which mice were administered LNP including a single AAV1-Shef1a-MYD88-ZFR11 vector and blood was drawn from the mice. “Sac” indicates when mice were sacrificed.

Figure 29:
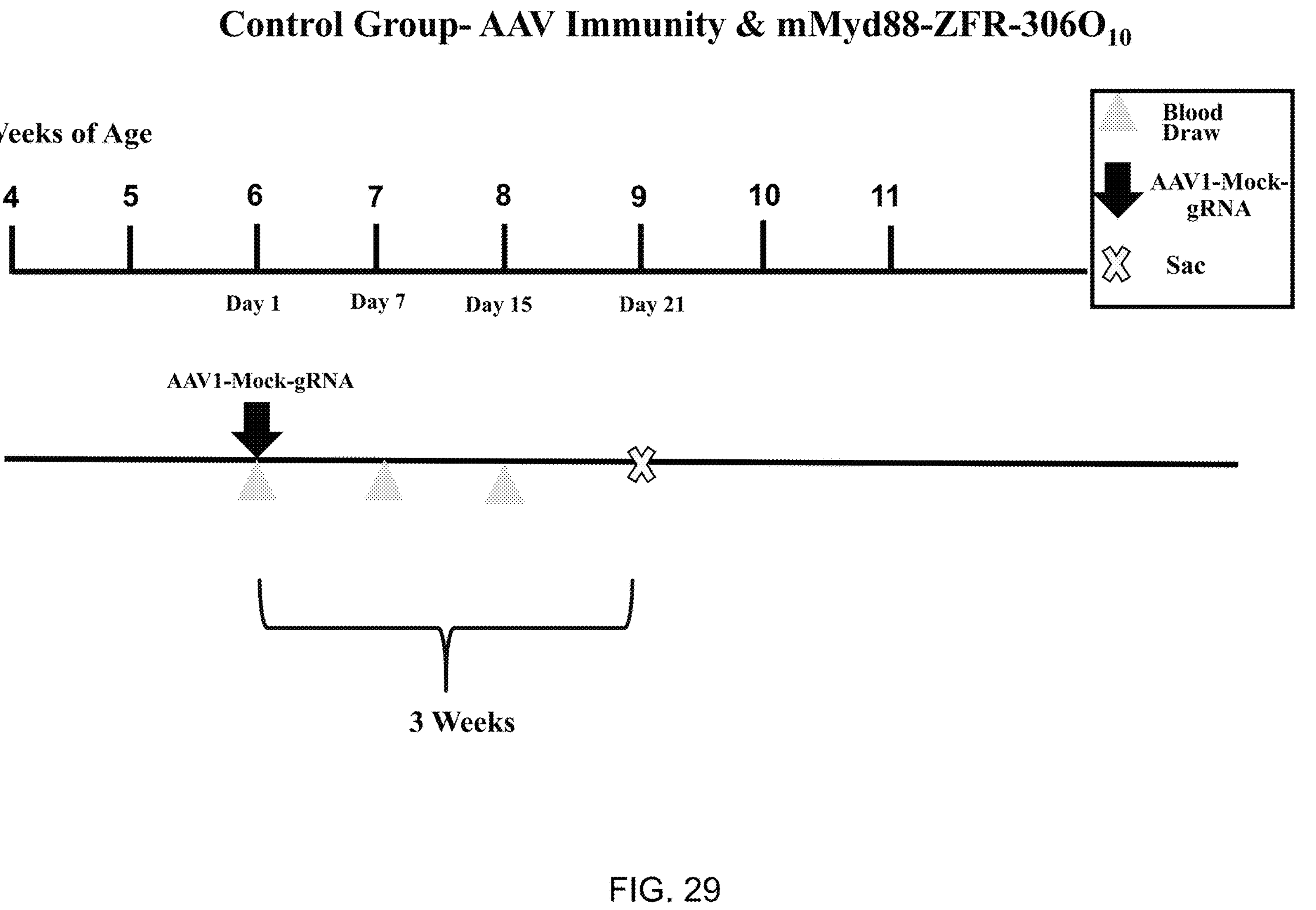

FIG. 29 is a schematic illustrating the time points at which mice were administered a single AAV1-Mock-gRNA vector and blood was drawn from the mice. “Sac” indicates when mice were sacrificed.

Figure 30A:
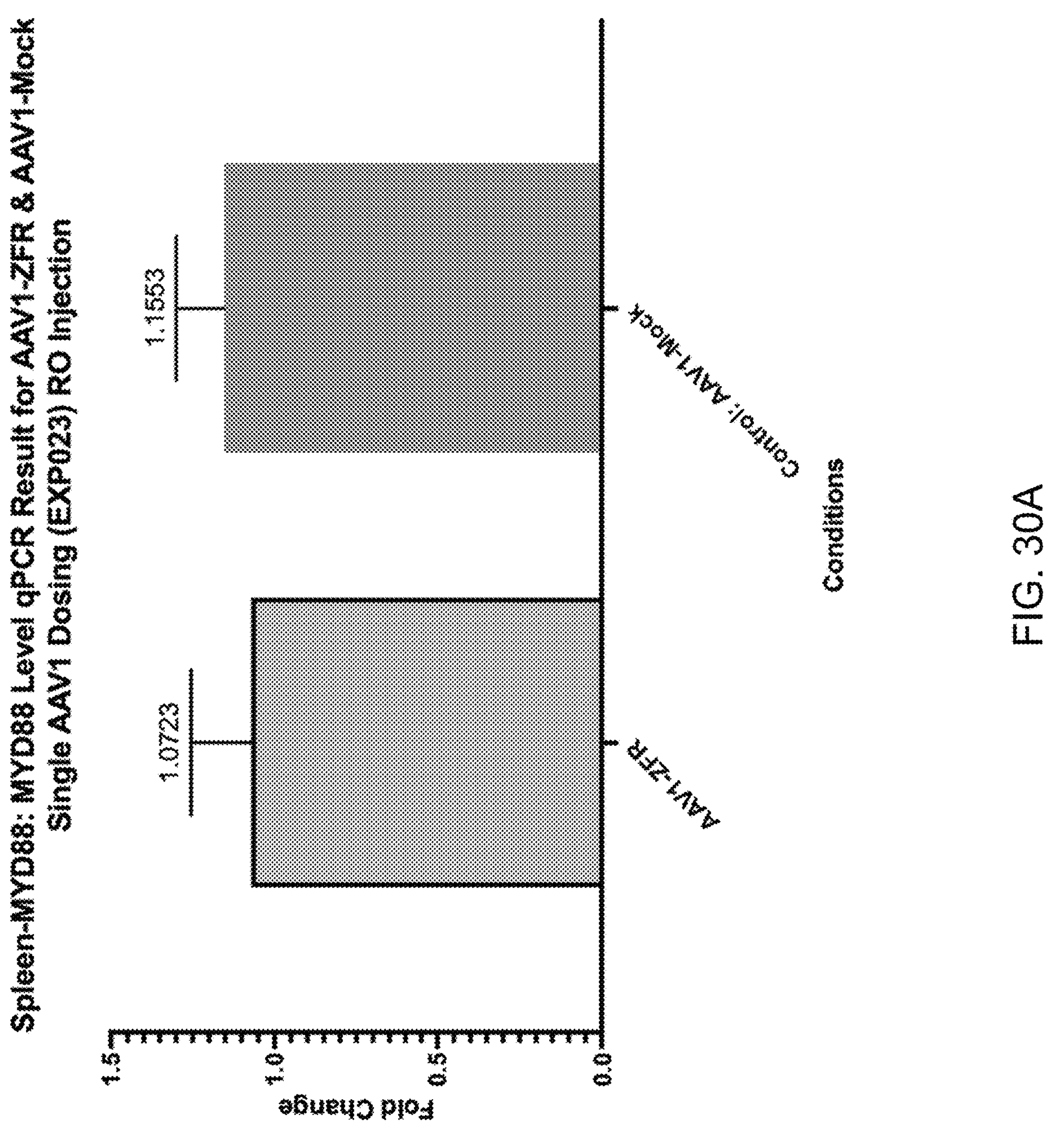
Figure 30B:
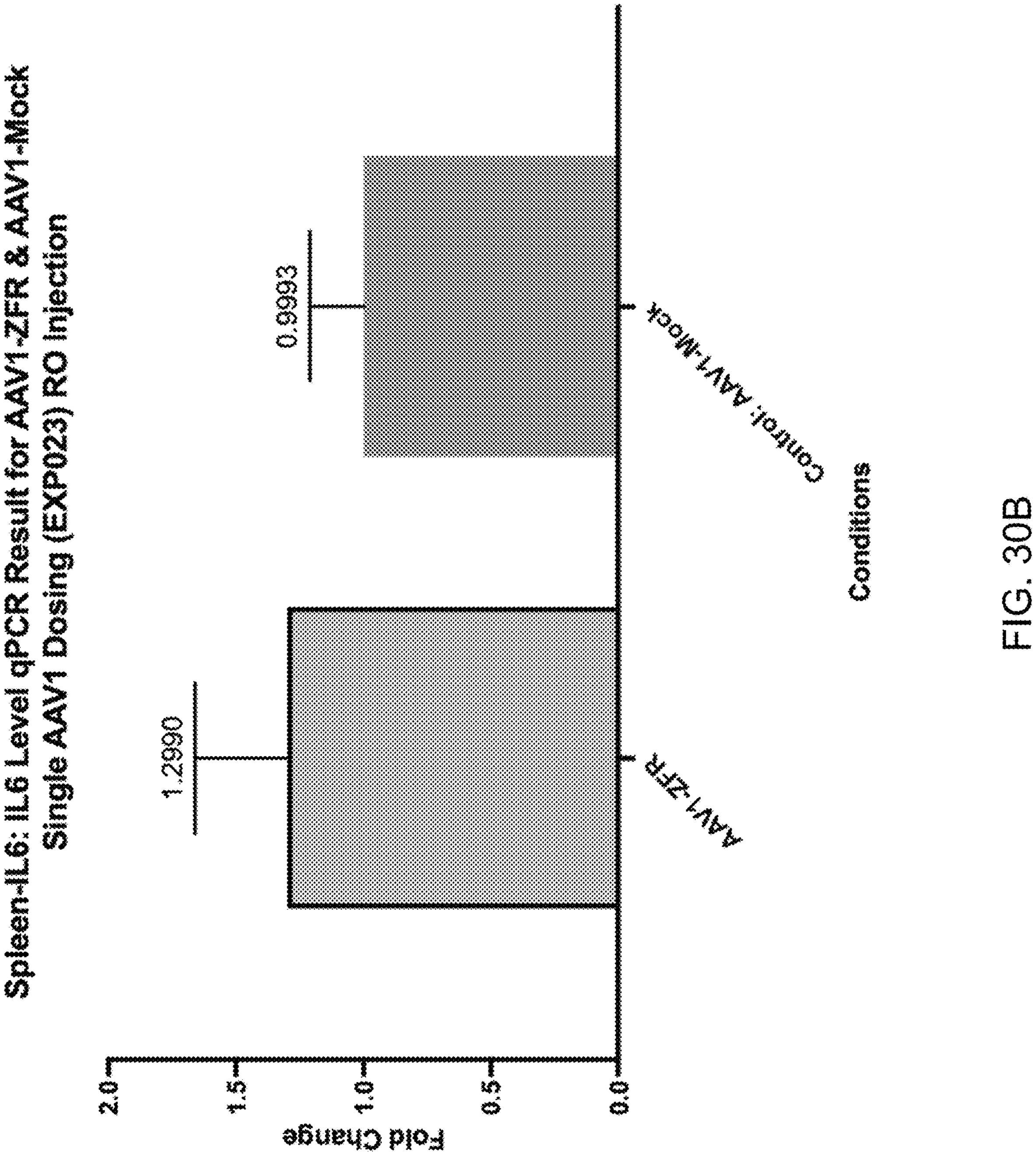

FIGS. 30A-30B are graphs showing the fold change in MYD88 transcript levels (A) and IL-6 transcript levels (B)

(as measured by qPCR) in mice treated with AAV1-Shef1a-MYD88-ZFR11 or AAV1-Mock-gRNA in spleen.

Figure 31A:
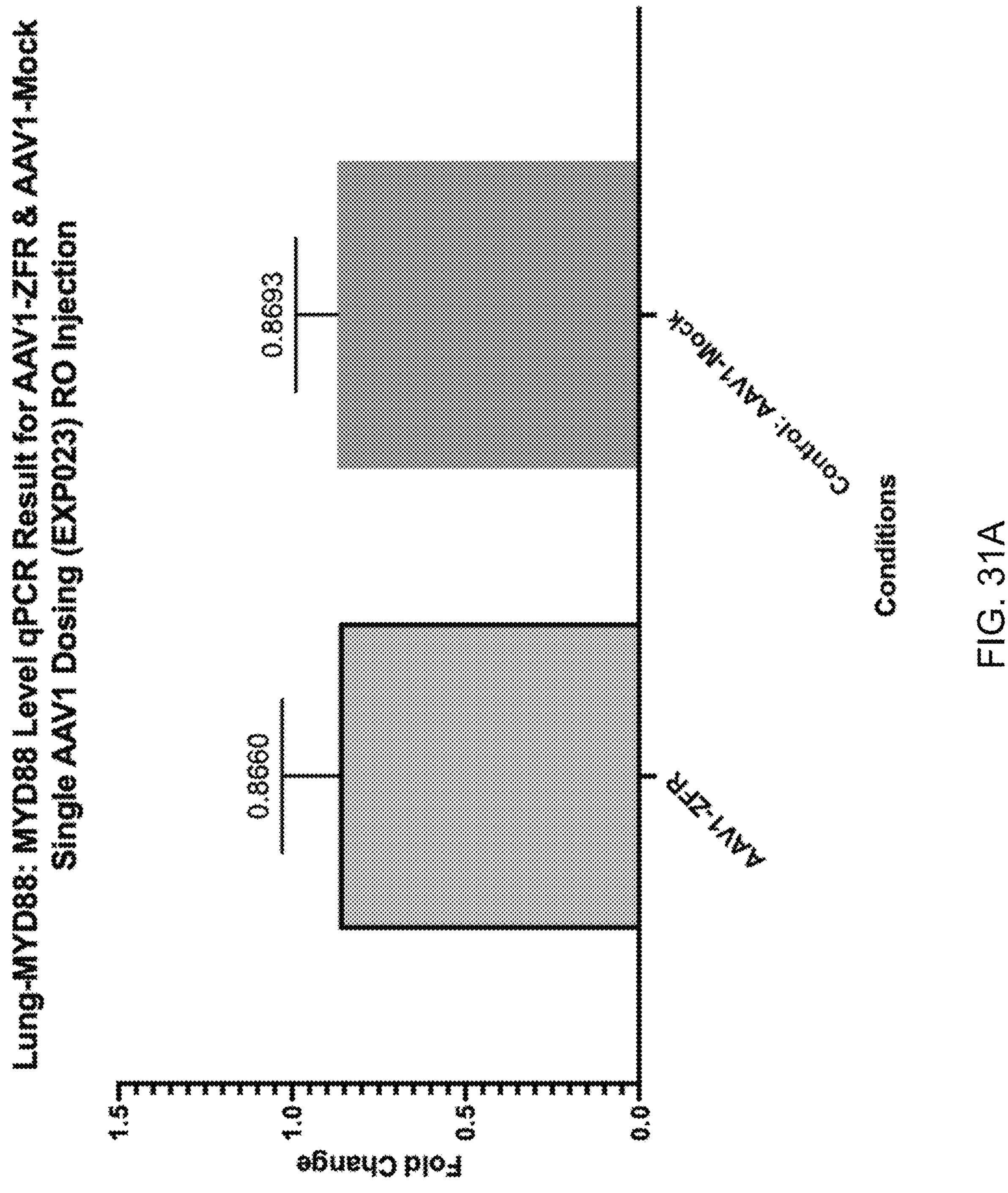
Figure 31B:
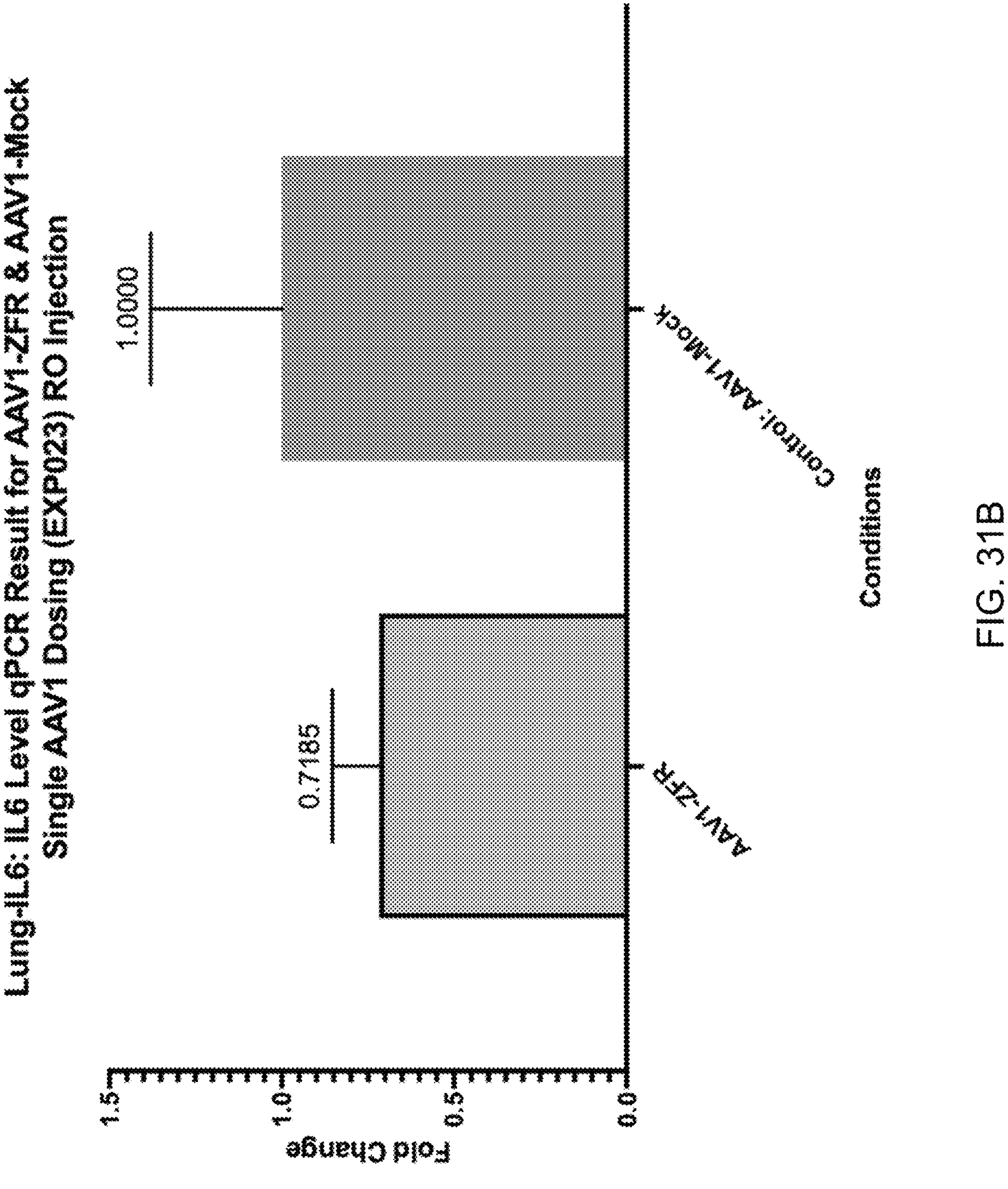

FIGS. 31A-31B are graphs showing the fold change in MYD88 transcript levels (A) and IL-6 transcript levels (B) (as measured by qPCR) in mice treated with AAV1-Shef1a-MYD88-ZFR11 or AAV1-Mock-gRNA in lung.

Figure 32A:
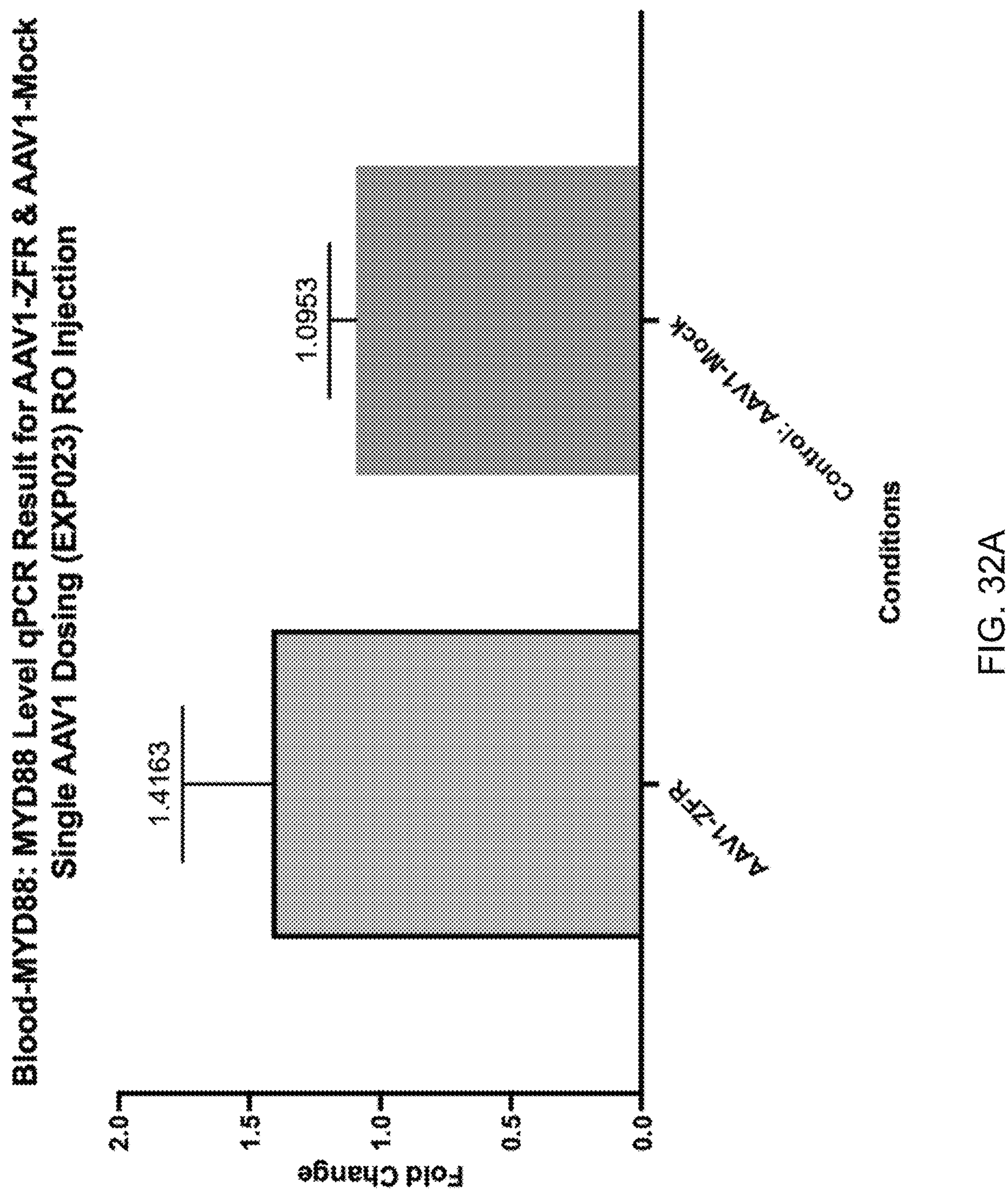
Figure 32B:
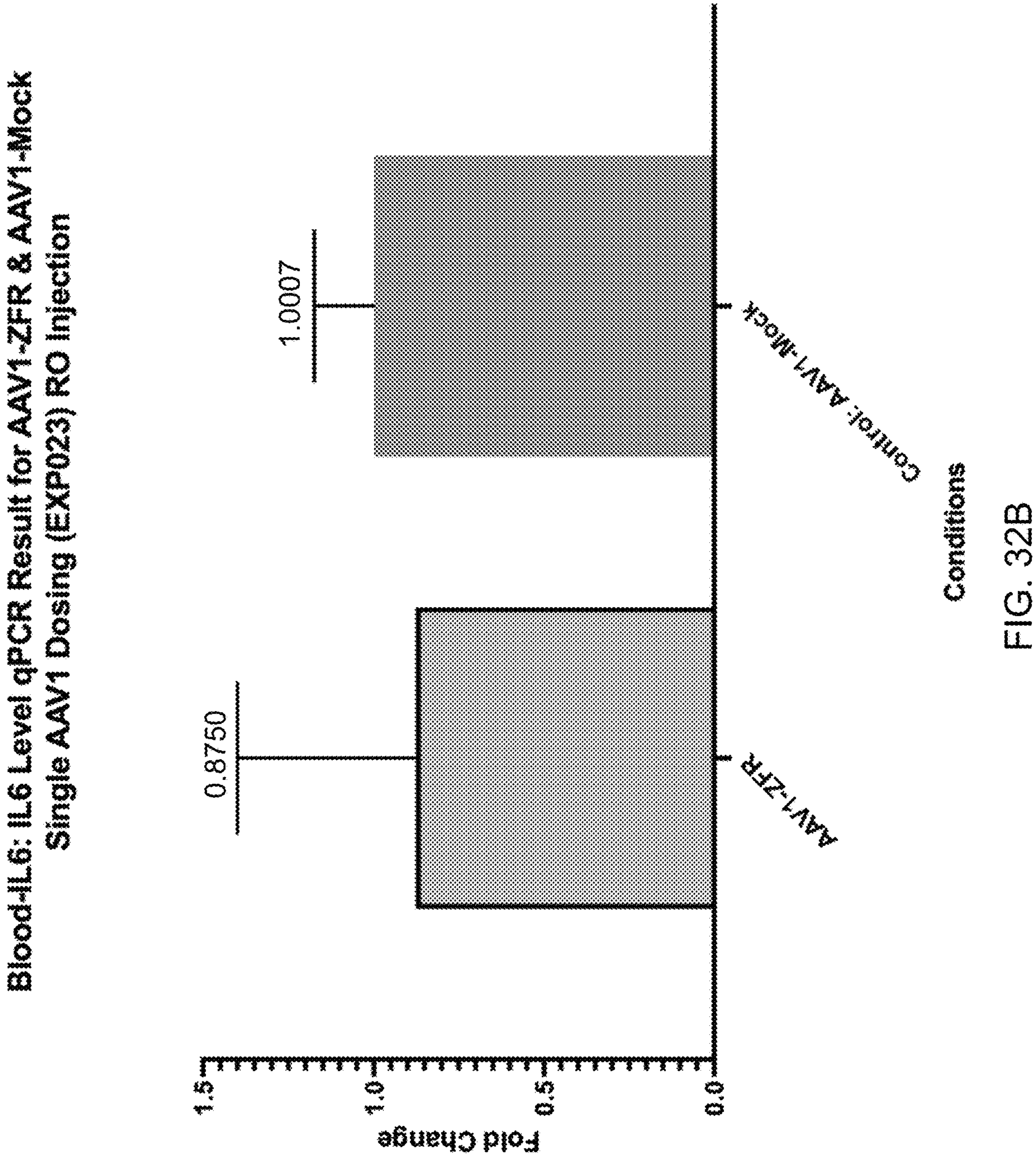

FIGS. 32A-32B are graphs showing the fold change in MYD88 transcript levels (A) and IL-6 transcript levels (B) (as measured by qPCR) in mice treated with AAV1-Shef1a-MYD88-ZFR11 or AAV1-Mock-gRNA in blood.

Figure 33A:
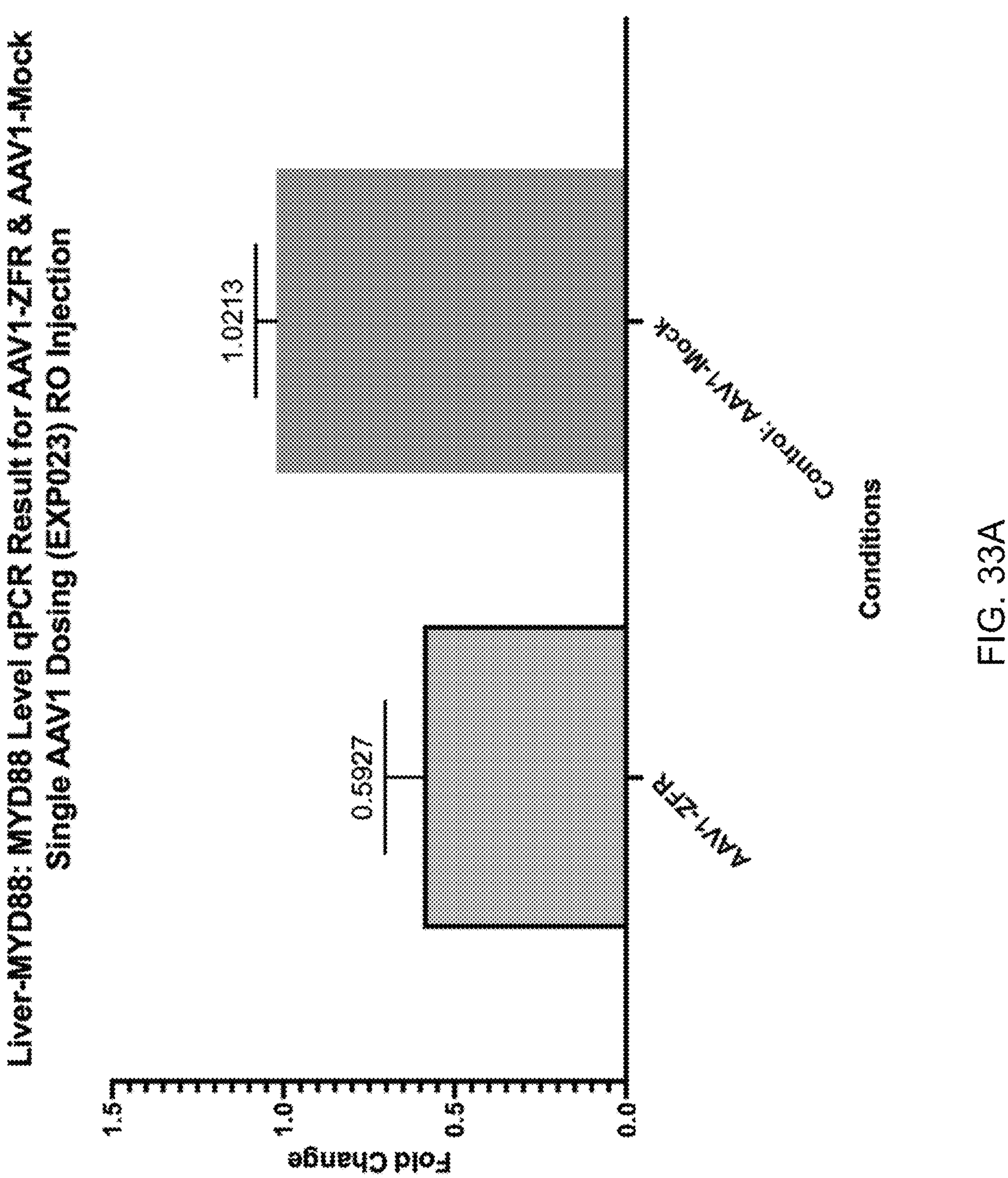

FIGS. 33A-33B are graphs showing the fold change in MYD88 transcript levels (A) and IL-6 transcript levels (B) (as measured by qPCR) in mice treated with AAV1-Shef1a-MYD88-ZFR11 or AAV1-Mock-gRNA in liver.

DETAILED DESCRIPTION OF THE INVENTION

Zinc fingers are proteins derived from eukaryotic systems that pose less safety challenges than CRISPR, such as immunogenicity, for targeting certain sequences in subjects. The advantage of using zinc fingers for transcriptional regulation lies in their eukaryotic origin, which facilitates the use of Myd88-based immunomodulation in human subjects. By targeting the promoter region of the Myd88 gene to repress Myd88 expression, the zinc finger protein can ameliorate inflammation and/or immune response (e.g., an improper or unwanted immune response) in a subject to which the zinc finger protein is administered.

An aspect of the invention provides a non-naturally occurring zinc finger protein, wherein the zinc finger protein specifically binds to the promoter region of the Myd88 gene.

In one aspect, the zinc finger protein comprises one or more (e.g., one, two, three, four, five, or six) of the following (i) a N-terminal fixed domain, (ii) a N-terminal backbone domain, (iii) a variable recognition helix, (iv) a C-terminal backbone domain, (v) a zinc finger linker, and (vi) a C-terminal domain.

Any suitable (i) a N-terminal fixed domain, (ii) a N-terminal backbone domain, (iii) a variable recognition helix, (iv) a C-terminal backbone domain, (v) a zinc finger linker, and (vi) a C-terminal domain can be utilized in the zinc finger protein. Exemplary (i) a N-terminal fixed domain, (ii) a N-terminal backbone domain, (iv) a C-terminal backbone domain, (v) a zinc finger linker, and (vi) a C-terminal domain sequences include SEQ ID NOs: 1-5, respectively.

The variable recognition helix is determined by the target sequence, i.e., the promoter region of the Myd88 gene. The target sequence, i.e., the promoter region of the Myd88 gene, can be from any suitable subject, including human, mouse, rat, guinea pig, hamster, rabbit, cat, dog, pig, cow, horse, or non-human primate. The genomic sequences of Myd88 gene (including the promoter sequence) are known in the art. For example, the genomic sequences of the Myd88 gene in mice and human are described in omim.org/entry/602170 (see also Hardiman et al., *Genomics,* 45:332-339 (1997); and Bonnert et al. (*FEBS Lett.,* 402:81-84 (1997)).

The target sequence can contain any suitable portion of the promoter region of the Myd88 gene. In one aspect, the target sequence contains 10-25 (e.g., 10, 11, 12, 13, 14, 15, 16, 17, 18, 19, 20, 21, 22, 23, 24, 25, 26, 27, 28, 29, 30, or any ranges thereof) nucleotides of the promoter region of the Myd88 gene. An exemplary portion of the promoter region of the Myd88 gene comprises SEQ ID NO: 12.

In one aspect, the zinc finger protein comprises the amino acid sequence encoded by the nucleotide sequence of SEQ ID NO: 6 or SEQ ID NO: 7 (which correspond to zinc finger proteins 3 and 11 described in the Example).

The zinc finger protein can further comprise one or more repressors. In that regard, an aspect of the invention provides a fusion protein that comprises the zinc finger protein and one or more repressors.

The repressors for use in aspects of the invention include, but are not limited to, Krüppel-associated box (Krab), MeCP2, SIN3A, HDT1, MBD2B, NIPP1, HP1A, and combinations thereof. In one aspect, the repressors are selected from the group consisting of Hp1a, Krab, MeCP2, and combinations thereof. In one aspect, the Hp1a repressor effector comprises the amino acid sequence encoded by the nucleotide sequence of SEQ ID NO: 8. In another aspect, the Krab repressor effector comprises the amino acid sequence encoded by the nucleotide sequence of SEQ ID NO: 9.

In a further aspect of the invention, the zinc finger protein comprises both of the Hp1a and Krab repressors (e.g., the amino acid sequence encoded by the nucleotide sequence of SEQ ID NO: 8 and SEQ ID NO: 9). A non-limiting example of the Hp1a-Krab repressor effector sequence comprises the amino acid sequence encoded by the nucleotide sequence of SEQ ID NO: 13.

Exemplary zinc finger proteins comprising the Hp1a-Krab repressor effector comprise the amino acid sequence encoded by the nucleotide sequence of SEQ ID NO: 10 (Zinc Finger 3—HP1a-krab) and the amino acid sequence encoded by the nucleotide sequence of SEQ ID NO: 11 (Zinc Finger 11—HP1a-krab).

The zinc finger protein can comprise a peptide or protein tag (e.g., for protein purification or detection). Peptide/protein tags are known in the art, such as those described in Johnson, "Protein/Peptide Tags," DOI//dx.doi.org/10.13070/mm.en.2.116 including but not limited to yellow fluorescent protein (YFP), red florescent protein (RFP), green fluorescent protein (GFP), FLAG, Myc epitope, polyhistidine, glutathione-S-transferase (GST), HA, V5, ABDz1-tag, Adenylate kinase (AK-tag), BC2-tag, Calmodulin-binding peptide, CusF, Fc, Fh8, Halo tag, Heparin binding peptide (HB-tag), Ketosteroid isomerase (KSI), maltose-binding protein (MBP), thioredoxin, PA (NZ-1), Poly-Arg, Poly-Lys, S-tag, SBP/Streptavidin-Binding Peptide, SNAP, Strep-II (Twin-Strep), and SUMO/SUMO2. Tags can be at either end of the protein.

The zinc finger protein can contain one or more linkers (e.g., flexible linkers, rigid linkers, and in vivo cleavable linkers) when other components (e.g., one or more repressors) are included. Besides the basic role in linking the functional domains together (as in flexible and rigid linkers) or releasing free functional domain in vivo (as in in vivo cleavable linkers), linkers offer many other advantages for the production of fusion proteins, such as improving biological activity, increasing expression yield, and achieving desirable pharmacokinetic profiles. Linkers are known in the art (see, e.g., Chen et al., Adv Drug Deliv Rev. 65 (10): 1357-1369 (2013)).

Flexible linkers are used when the joined domains require a certain degree of movement or interaction. They are generally composed of small, non-polar (e.g. Gly) or polar (e.g. Ser or Thr) amino acids. The small size of these amino acids provides flexibility, and allows for mobility of the connecting functional domains. The incorporation of Ser or Thr can maintain the stability of the linker in aqueous solutions by forming hydrogen bonds with the water molecules, and therefore reduces the unfavorable interaction between the linker and the protein moieties.

The zinc finger also can contain a signal peptide (i.e., a signal sequence, targeting signal, localization signal, localization sequence, transit peptide, leader sequence, or leader peptide), which is a short peptide present at the N-terminus or occasionally C-terminus of most newly synthesized proteins that are destined toward the secretory pathway. These proteins include those that reside either inside certain organelles (the endoplasmic reticulum, Golgi or endosomes), secreted from the cell, or inserted into most cellular membranes. Exemplary signal peptides are known in the art and a person of ordinary skill in the art would recognize how to select a particular signal peptide for use in aspects of the invention.

It has also been discovered that targeting expression of the Myd88 gene using RNAi interference may be useful for the development of tolerogenic vaccines. Tolerogenic vaccines induce immunological tolerance toward a target antigen against which an immune response is undesirable. The target antigen may be, for example, a viral antigen, for example, a viral antigen associated with a gene therapy virus. For example, the target antigen may be VP1 of an AAV virus. The gene therapy virus may be as described herein with respect to other aspects of the invention.

In an aspect, the RNAi agent may comprise a small interfering RNA (siRNA), a short hairpin miRNA (shMIR), a microRNA (miRNA), or an antisense nucleic acid. In some aspects, the RNAi agent employed cleaves the Myd88 mRNA. In other embodiments, the RNAi agent employed does not cleave the Myd88 mRNA. In an aspect, the RNAi agent comprises a nucleotide sequence complementary to at least about 8, at least about 15, at least about 19, or from about 19 to about 22 nucleotides of a nucleic acid encoding one or both of Myd88 mRNA and Myd88 protein or a complement thereof. In an aspect, the siRNA may comprise, e.g., trans-acting siRNAs (tasiRNAs) and/or repeat-associated siRNAs (rasiRNAs). In another embodiment, the miRNA may comprise, e.g., a short hairpin miRNA (shMIR).

An aspect of the invention also provides a nucleic acid (polynucleotide) encoding the zinc fusion protein or RNAi agent. The nucleic acid can comprise DNA, cDNA, and/or RNA, can be single or double stranded, and can be naturally-occurring, synthetic, and/or recombinant. In one aspect, the polynucleotide is an mRNA.

Furthermore, the nucleic acid can comprise nucleotide analogues or derivatives (e.g., inosine or phophorothioate nucleotides and the like). Silent mutations in the coding sequence result from the degeneracy (i.e., redundancy) of the genetic code, whereby more than one codon can encode the same amino acid residue. Thus, for example, leucine can be encoded by CTT, CTC, CTA, CTG, TTA, or TTG: serine can be encoded by TCT, TCC, TCA, TCG, AGT, or AGC: asparagine can be encoded by AAT or AAC: aspartic acid can be encoded by GAT or GAC: cysteine can be encoded by TGT or TGC: alanine can be encoded by GCT, GCC, GCA, or GCG: glutamine can be encoded by CAA or CAG: tyrosine can be encoded by TAT or TAC: and isoleucine can be encoded by ATT, ATC, or ATA.

The polynucleotide can encode the zinc finger protein alone or as part of a fusion protein (e.g., comprising one or more repressors). The polynucleotide encoding the zinc finger protein or RNAi agent can be provided as part of a construct comprising the nucleic acid and elements that enable delivery of the nucleic acid to a cell, and/or expression of the nucleic acid in a cell. For example, the polynucleotide sequence encoding the zinc finger protein or RNAi agent can be operatively linked to expression control sequences. An expression control sequence operatively linked to a coding sequence is ligated such that expression of the coding sequence is achieved under conditions compatible with the expression control sequences. The expression control sequences include, but are not limited to, appropriate promoters, enhancers, transcription terminators, a start codon (i.e., ATG) in front of a protein-encoding gene, splicing signal for introns, maintenance of the correct reading frame of that gene to permit proper translation of mRNA, and stop codons. Suitable promoters include, but are not limited to, an SV40 early promoter, RSV promoter, adenovirus major late promoter, human CMV immediate early I promoter, poxvirus promoter, 30K promoter, I3 promoter, sE/L promoter, 7.5K promoter, 40K promoter, and C1 promoter.

A polynucleotide encoding the RNAi agent, zinc finger protein or fusion protein can be cloned or amplified by in vitro methods, such as the polymerase chain reaction (PCR), the ligase chain reaction (LCR), the transcription-based amplification system (TAS), the self-sustained sequence replication system (3SR) and the Qβ replicase amplification system (QB). For example, a polynucleotide encoding the RNAi agent or zinc finger protein can be isolated by polymerase chain reaction of cDNA using primers based on the DNA sequence of the molecule. A wide variety of cloning and in vitro amplification methodologies are well known to persons skilled in the art.

An aspect of the invention further provides a vector comprising the polynucleotide. Examples of suitable vectors include plasmids (e.g., DNA plasmids), bacterial vectors, and viral vectors, such as adenovirus vectors, adeno-associated virus (AAV) vectors, poxvirus vectors, retrovirus vectors, herpes virus vectors, polio virus vectors, and alphavirus vectors. When the vector is a plasmid (e.g., DNA plasmid), the plasmid can be complexed with chitosan. In a one aspect, the vector is an AAV or HSV (e.g., HSV-1) vector. In one aspect, the vector comprising the polynucleotide further comprises a polynucleotide encoding viral antigen (e.g., VP1 coat protein for AAV).

The vector for use in aspects of the invention can include an expression control sequence operatively linked to coding sequence, such that expression of the coding sequence is achieved under conditions compatible with the expression control sequences. The expression control sequences include, but are not limited to, appropriate promoters, enhancers, transcription terminators, a start codon (i.e., ATG) in front of a protein-encoding gene, splicing signal for introns, maintenance of the correct reading frame of that gene to permit proper translation of mRNA, and stop codons.

The term "enhancer" as used herein, refers to a DNA sequence that increases transcription of, for example, a nucleotide sequence to which it is operably linked. Enhancers can be located many kilobases away from the coding region of the nucleotide sequence and can mediate the binding of regulatory factors, patterns of DNA methylation, or changes in DNA structure. A large number of enhancers from a variety of different sources are well known in the art and are available as or within cloned polynucleotides (from, e.g., depositories such as the ATCC as well as other commercial or individual sources). A number of polynucleotides comprising promoters (such as the commonly-used CMV promoter) also comprise enhancer sequences. Enhancers can be located upstream, within, or downstream of coding sequences. For example, the nucleotide encoding the polypeptide can be operably linked to a CMV enhancer/chicken β-actin promoter (also referred to as a "CAG promoter").

Additionally, the vector can comprise nucleic acid sequence encoding a reporter to identify the transfection/transduction efficiency of the vector.

A cell (e.g., isolated cell or host cell) comprising the RNAi agent, zinc finger protein, polynucleotide, or vector also is provided herein. Suitable cells include prokaryotic and eukaryotic cells, e.g., mammalian cells, fungi (e.g., yeast), and bacteria (such as *E. coli, Salmonella* (e.g., *S. typhimurium*), or *Listeria* (e.g., *L. monocytogenes*). The cell can be in vitro, as is useful for research or for production of the RNAi agent or zinc finger protein, or the cell can be in vivo. Transformation of a host cell with recombinant DNA can be carried out by conventional techniques as are well known to those skilled in the art.

The RNAi agent, zinc finger protein, polynucleotide, vector, or cell can be formulated as a composition (e.g., pharmaceutical composition) comprising the RNAi agent, zinc finger protein, polynucleotide, vector, or cell and a carrier (e.g., a pharmaceutically or physiologically acceptable carrier). Furthermore, the RNAi agent, zinc finger protein, polynucleotide, vector, or cell, or composition of aspects of the invention can be used in the methods described herein alone or as part of a pharmaceutical formulation.

The composition (e.g., pharmaceutical composition) can comprise more than one RNAi agent, zinc finger protein, polynucleotide, vector, or cell or composition of aspects of the invention. Alternatively, or in addition, the composition can comprise one or more other additional therapeutic agents. Examples of such additional therapeutic agents that may be suitable for use in the pharmaceutical composition include gene therapies, immunosuppressants, anti-inflammatoires, and agents or drugs that decrease an immune response, such as for use in the treatment of autoimmune disorders, with organ transplants, and for the treatment of inflammatory conditions. The compositions may be useful for developing tolerogenic vaccines. In aspects wherein the composition is a tolerogenic vaccine, the composition may further comprise a target antigen against which immune tolerance is desired or a polynucleotide encoding the target antigen. Examples of such target antigens may include viral antigens.

Exemplary additional therapeutic agents include gene therapies (e.g., cystic fibrosis gene therapy), corticosteroids (e.g., prednisone, budesonide, and prednisolone), Janus kinase inhibitors (e.g., tofacitinib), calcineurin inhibitors (cyclosporine and tacrolimus), mTOR inhibors (sirolimus and everolimus), IMDH inhibitors (azathioprine, leflunomide, and mycophenolate), biologics (abatacept, adalimumab, anakinra, certolizumab, etanercept, golimumab, infliximab, ixekizumab, natalizumab, rituximab, secukinumab, tocilizumab, ustekinumab, and vedolizumab), monoclonal antibodies (e.g., basiliximab and daclizumab, and NSAIDS (e.g., aspirin, choline and magnesium salicylates, celecoxib, diclofenac potassium, diclofenac sodium, diclofenac sodium with misoprostol, diflunisal, etodolac, fenoprofen calcium, flurbiprofen, ibuprofen, indomethacin, ketoprofen, magnesium salicylate, meclofenamate sodium, mefenamic acid, meloxicam, nabumetone, naproxen, naproxen sodium, oxaprozin, piroxicam, salsalate, sodium salicylate, sulindac, tolmetin sodium, and valdecoxib).

The zinc finger protein, polynucleotide, vector, cell, or composition thereof may be useful as a tolerogenic vaccine. Tolerogenic vaccines induce immunological tolerance toward a target antigen against which an immune response is undesirable. The tolerogenic vaccine may be therapeutic or prophylactic. In this regard, the composition may comprise (A) one or more zinc finger proteins, one or more polynucleotides, one or more vectors, one or more cells, or one or more compositions thereof: (B) a target antigen against which immune tolerance is desired or a polynucleotide encoding the target antigen: and (C) a gene therapy. The gene therapy may be as described herein with respect to other aspects of the invention. The target antigen may be, for example, a viral antigen, for example, a viral antigen associated with a gene therapy virus. For example, the target antigen may be VP1 of an AAV virus. The gene therapy virus may be as described herein with respect to other aspects of the invention. In an aspect. (A), (B), and (C) may be administered to a subject simultaneously in separate compositions or combined together in a single composition. In an aspect of the invention, the composition comprises (A), (B), and (C) in a single composition. In another aspect, (A), (B), and (C) may be administered to a subject sequentially. In this regard, an aspect of the invention provides a single set of separate compositions, each respective composition separately comprising (A), (B), or (C). Alternatively, the set may comprise (A) and (B) together in a first composition and (C) in a second composition. Each of (A), (B), and (C) may further comprise a pharmaceutically acceptable carrier, as described herein with respect to other aspects of the invention.

The RNAi agent targeting the Myd88 gene, polynucleotide, vector, cell, or composition thereof may be useful as a tolerogenic vaccine. An aspect of the invention provides a pharmaceutical composition comprising a pharmaceutically acceptable carrier and: (A) (i) one or more RNA interference (RNAi) agents targeting the Myd88 gene, (ii) one or more cells comprising the one or more RNAi agents, (iii) one or more polynucleotides encoding the one or more RNAi agents, or (iv) one or more vectors comprising the one or more polynucleotides: (B) a target antigen or a polynucleotide encoding the target antigen; and (C) a gene therapy. The target antigen and the gene therapy may be as described herein with respect to other aspects of the invention. In an aspect, (A), (B), and (C) may be administered to a subject simultaneously in separate compositions or combined together in a single composition. In an aspect of the invention, the composition comprises (A), (B), and (C) in a single composition. In another aspect, (A), (B), and (C) may be administered to a subject sequentially. In this regard, an aspect of the invention provides a single set of separate compositions, each respective composition separately comprising (A), (B), or (C). Alternatively, the set may comprise (A) and (B) together in a first composition and (C) in a second composition. Each of (A), (B), and (C) may further comprise a pharmaceutically acceptable carrier, as described herein with respect to other aspects of the invention.

The carrier can be any of those conventionally used and is limited only by physio-chemical considerations, such as solubility and lack of reactivity with the active compound(s) and by the route of administration. The pharmaceutically acceptable carriers described herein, for example, vehicles, adjuvants, excipients, and diluents, are well-known to those skilled in the art and are readily available to the public. It is preferred that the pharmaceutically acceptable carrier be one which is chemically inert to the active agent(s) and one which has no detrimental side effects or toxicity under the conditions of use.

The choice of carrier will be determined in part by the particular RNAi agent, zinc finger protein, polynucleotide, vector, cell, or composition thereof and other active agents or drugs used, as well as by the particular method used to administer the RNAi agent, zinc finger protein, polynucleotide, vector, cell, or composition thereof. In one aspect, the pharmaceutically accepted carrier is lipid nanoparticles (LNP). In one aspect, the composition comprises mRNA encoding a zinc finger protein in an LNP formulation delivered using adeno-associated virus.

In an aspect, the composition may further comprise a gene therapy or foreign antigen. For example, a vector comprising a polynucleotide encoding the RNAi agent, zinc finger protein may further comprise a polynucleotide encoding a gene therapy carrier, cargo or portion thereof. In an aspect, the composition further comprises rapamycin, an mTor inhibitor.

An aspect of the invention provides a method for ameliorating inflammation and/or immune response in a subject, the method comprising administering to the subject a therapeutically effective amount of (i) one or more of the zinc finger proteins, (ii) one or more of the cells, (iii) one or more of the polynucleotides, (iv) one or more of the vectors, or (v) a pharmaceutical composition thereof, thereby ameliorating inflammation and/or immune response in the subject.

In some aspects, the inflammation and/or immune response (i.e., improper or unwanted immune response) may be associated with an inflammatory disorder, autoimmune disorder, or organ transplant in the subject. Exemplary disorders include, but are not limited to, asthma, ulcer, psoriasis, lupus, rheumatoid arthritis, Crohn's disease, multiple sclerosis, or immunogenicity to gene therapies (e.g., cystic fibrosis gene therapy).

In some aspects, the inflammation and/or immune response (i.e., improper or unwanted immune response) may be associated with gene therapy, e.g., gene therapy viruses or other foreign antigens.

The RNAi agent, zinc finger protein, polynucleotide, vector, cell, or composition thereof may be useful as a tolerogenic vaccine. The tolerogenic vaccine may be therapeutic or prophylactic. An aspect of the invention provides a method for inducing immune tolerance against a target antigen in a subject. The method may comprise administering to the subject a therapeutically or prophylactically effective amount of (i) one or more of the zinc finger proteins, (ii) a target antigen or a polynucleotide encoding the target antigen, (iii) one or more cells comprising (i) and (ii), (iv) one or more polynucleotides encoding (i), (v) one or more vectors comprising the one or more polynucleotides, or (vi) a pharmaceutical composition comprising any one of (i)-(v), thereby inducing immunogenic tolerance against the target antigen. The target antigen may be an antigen against which an immune response is undesirable and may be as described herein with respect to other aspects of the invention.

In an aspect, the method for ameliorating inflammation and/or immune response associated with gene therapy in a subject comprises administering a tolerogenic vaccine to the subject including: (A) the zinc finger protein, polynucleotide, vector, cell, or composition thereof: (B) a target antigen against which immune tolerance is desired or a polynucleotide encoding the target antigen: and (C) the gene therapy, wherein (A), (B), and (C) are administered to the subject simultaneously. In an aspect, the method for ameliorating inflammation and/or immune response associated with gene therapy in a subject comprises administering to the subject: (A) the zinc finger protein, polynucleotide, vector, cell, or composition thereof: (B) a target antigen against which immune tolerance is desired or a polynucleotide encoding the target antigen: and (C) the gene therapy, wherein (A), (B), and (C) are administered to the subject sequentially. In an aspect, the method comprises administering to (A) and (B) to the subject before administering (C) to the subject. In another aspect, the method comprises administering to (C) to the subject before administering (A) and (B) to the subject. The gene therapy administered to the subject may be viral or non-viral. In an aspect of the invention, the gene therapy comprises a gene therapy virus. The gene therapy virus may be, for example, a retrovirus, adenovirus, herpes simplex virus, vaccinia virus, or an adeno-associated virus. In an aspect, the gene therapy is a non-viral gene therapy. The non-viral gene therapy may comprise, for example, DNA or RNA (e.g., messenger RNA (mRNA)). In an aspect, the method further comprises administering rapamycin to the subject. The rapamycin may be packaged within LNPs or other carriers.

Another aspect of the invention provides a method for inducing immune tolerance in a subject comprising administering to the subject a therapeutically or prophylactically effective amount of: (A) (i) one or more RNA interference (RNAi) agents targeting the Myd88 gene, (ii) one or more cells comprising the one or more RNAi agents, (iii) one or more polynucleotides encoding the one or more RNAi agents, or (iv) one or more vectors comprising the one or more polynucleotides: (B) a target antigen or a polynucleotide encoding a target antigen: and (C) a gene therapy, thereby inducing immunogenic tolerance against the target antigen. The gene therapy and target antigen may be as described herein with respect to other aspects of the invention. In an aspect, (A), (B) and (C) are administered to the subject simultaneously. In another aspect, (A), (B) and (C) are administered to the subject sequentially. The method may comprise administering to (A) and (B) to the subject before administering (C) to the subject. Alternatively, the method may comprise administering to (C) to the subject before administering (A) and (B) to the subject.

The RNAi agent, zinc finger protein, polynucleotide, vector, cell, or composition thereof can be administered can be administered to a subject (e.g., a mammal, such as a non-human mammal including a mouse, rat, guinea pig, hamster, rabbit, cat, dog, pig, cow, horse, or non-human primate, or a human subject) by any suitable route including, but not limited to, parental (subcutaneous, intranasal, intramuscular, intradermal, intraperitoneal, intrathecal, intravenous, and intratumoral), systemic, topical, oral, or local administration. In one aspect, the RNAi agent, zinc finger protein, polynucleotide, vector, cell, or composition thereof is administered by subcutaneous injection. In a particular aspect, the subject is a mammal, such as a human subject.

The RNAi agent, zinc finger protein, polynucleotide, vector, cell, or composition thereof preferably targets immune cells for the amelioration of inflammation or immune response (e.g., the amelioration, reduction, inhibition, or elimination of inflammation or immune response) in the subject. Exemplary immune cells include, for example, lymphocytes, macrophages, dendritic cells, B cells, T cells, hematopoietic stem cells, and PBMCs.

Any suitable dose of the RNAi agent, zinc finger protein, polynucleotide, vector, cell, or composition thereof can be administered to a subject. The appropriate dose will vary depending upon such factors as the subject's age, weight, height, sex, general medical condition, previous medical history, and disease progression and can be determined by a clinician.

In another aspect, the RNAi agent, zinc finger protein, polynucleotide, vector, cell, or composition thereof is administered to the subject more than once (e.g., 2, 3, 4, 5, 6, 7, 8, 9, or 10 times). When multiple administrations are given, the administrations can be at one or more sites in a host and a single dose can be administered by dividing the single dose into equal portions for administration at one, two, three, four or more sites on the individual.

When the RNAi agent, zinc finger protein, polynucleotide, vector, cell, or composition thereof is administered with one or more additional therapeutic agents, the RNAi agent, zinc finger protein, polynucleotide, vector, cell, or composition thereof and one or more additional therapeutic agents can be co-administered to the subject. In this regard, the RNAi agent, zinc finger protein, polynucleotide, vector, cell, or composition thereof can be administered first and the one or more additional therapeutic agents can be administered second, or vice versa. Alternatively, the RNAi agent, zinc finger protein, polynucleotide, vector, cell, or composition thereof and the one or more additional therapeutic agents can be administered simultaneously.

In order to optimize the efficiency of Myd88 repression, sixteen different zinc finger proteins fused to the HP1a-krab repression effectors (ZFRs) were screened by in vitro transfection into mouse neuroblastoma cell line (N2A cells). Briefly, RNA was extracted after the transfection and cDNA synthesized, followed by qPCR. Transfection was performed with Lipo LTX. N2A passage number was 20. N2A seeding plate was collagen coated so that no cells were lost during media change with vacuum at the time of transfection. Cells were imaged and puromycin selected 24 hrs and 48 hrs after transfection.

ZFRs 1-16 were plated with 300 ng ZFR, 50 ng puromycin (puro), and 50 ng yellow fluorescent protein (YFP) (total 400 ng); n=2. For comparison purposes, the following were also plated (n=2) (Table 1):

TABLE 1

| | | | | | | Total |
|---|---|---|---|---|---|---|
| dCas9 plus Myd88 target sequence | 100 ng dCas9-HP 1a-krab | 200 ng Myd88-g1 20 nt | 50 ng puro | | 50 ng YFP | 400 ng |
| dCas9 only | 100 ng dCas9-HP 1a-krab | | 50 ng puro | 300 ng pIDT | 50 ng YFP | 400 ng |
| Cas9 plus Myd88 target sequence | 100 ng RSV Cas9 | 200 ng Myd88-g1 14 nt | 50 ng puro | | 50 ng YFP | 400 ng |
| Cas9 only | 100 ng RSV Cas9 | | 50 ng puro | 300 ng pIDT | 50 ng YFP | 400 ng |
| YPF Only | | | 50 ng puro | 300 ng pIDT | 50 ng YFP | 400 ng |
| Untransfected (with antibiotic) | | | | | | |
| Untransfected (without antibiotic) | | | | | | |

The following example further illustrates aspects of the invention but, of course, should not be construed as in any way limiting its scope.

Example 1

This example demonstrates the design of a zinc finger protein that specifically binds to the promoter region of the Myd88 gene.

Sixteen different 20 nt target regions inside the promoter sequence of the Myd88 gene were selected. Using an online Zinc finger design tool (zincfingertools.org), sixteen different Zinc fingers were designed for targeting the target regions of the Myd88 promoter. An exemplary target site of the promoter region of the Myd88 gene is GGA GGG GGA GGA AGG GGG (SEQ ID NO: 12), which corresponds to the mouse Myd88 gene.

Zinc finger proteins were designed with an N-terminal fixed domain (SEQ ID NO: 1), an N-terminal backbone domain (SEQ ID NO: 2), a variable recognition helix, a C-terminal backbone domain (SEQ ID NO: 3), a zinc finger linker (SEQ ID NO: 4), and a C-terminal domain (SEQ ID NO: 5). The variable recognition helix varied depending on the target site of the promoter region of the Myd88 gene. Exemplary sequences for the zinc finger proteins are SEQ ID NO: 6 (zinc finger 3) and SEQ ID NO: 7 (zinc finger 11).

Once zinc finger proteins were synthesized, they were fused to HP1a-krab repression effectors, such as the HP1a-krab repression effector of SEQ ID NO: 13.

Figure 1:
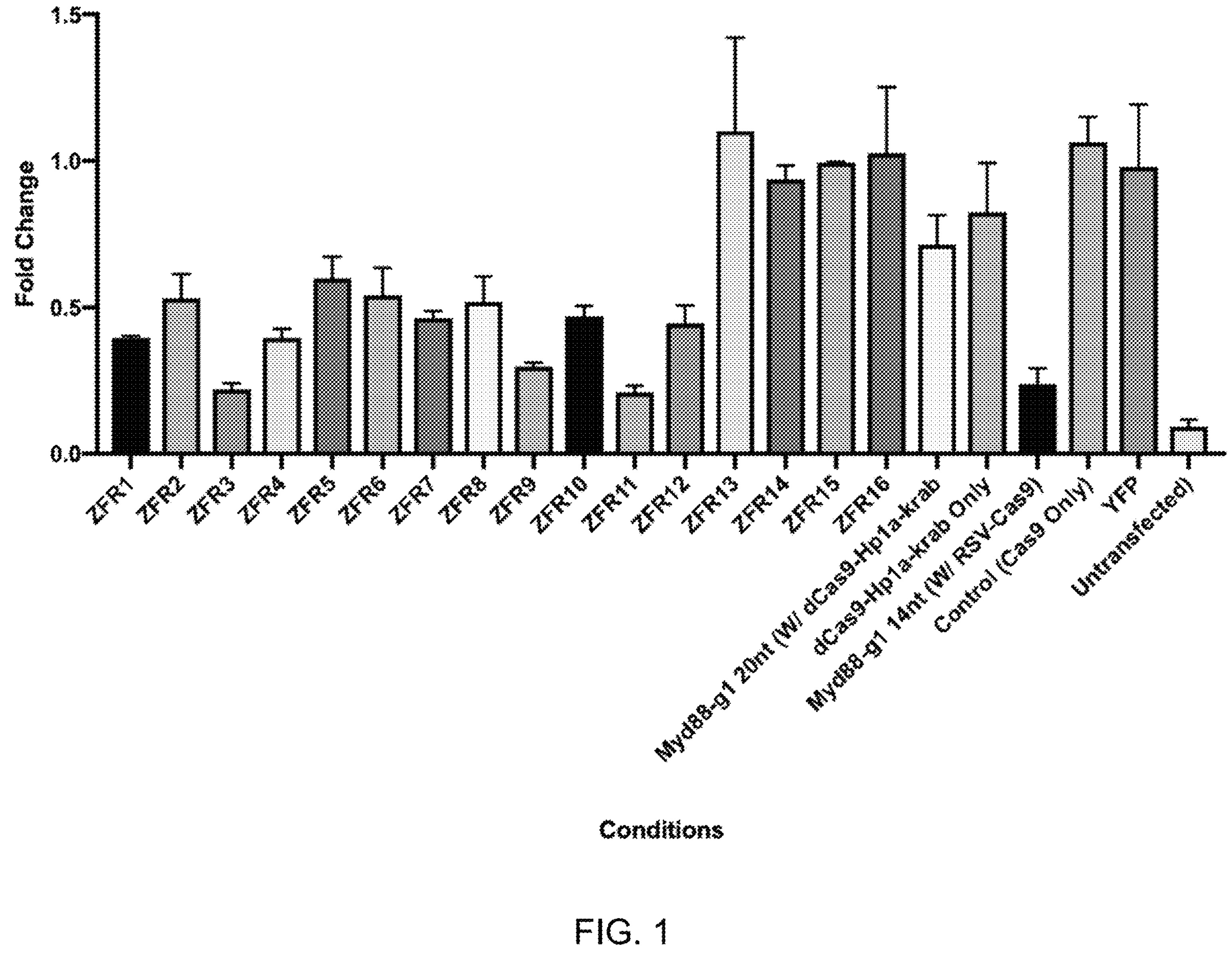
FIG. 1 is a Myd88 gene expression plot showing the fold change in Myd88 gene expression following transfection of N2A cells with zinc finger protein 1-16 fused to HP1a-krab repression effectors.
Figure 2A:
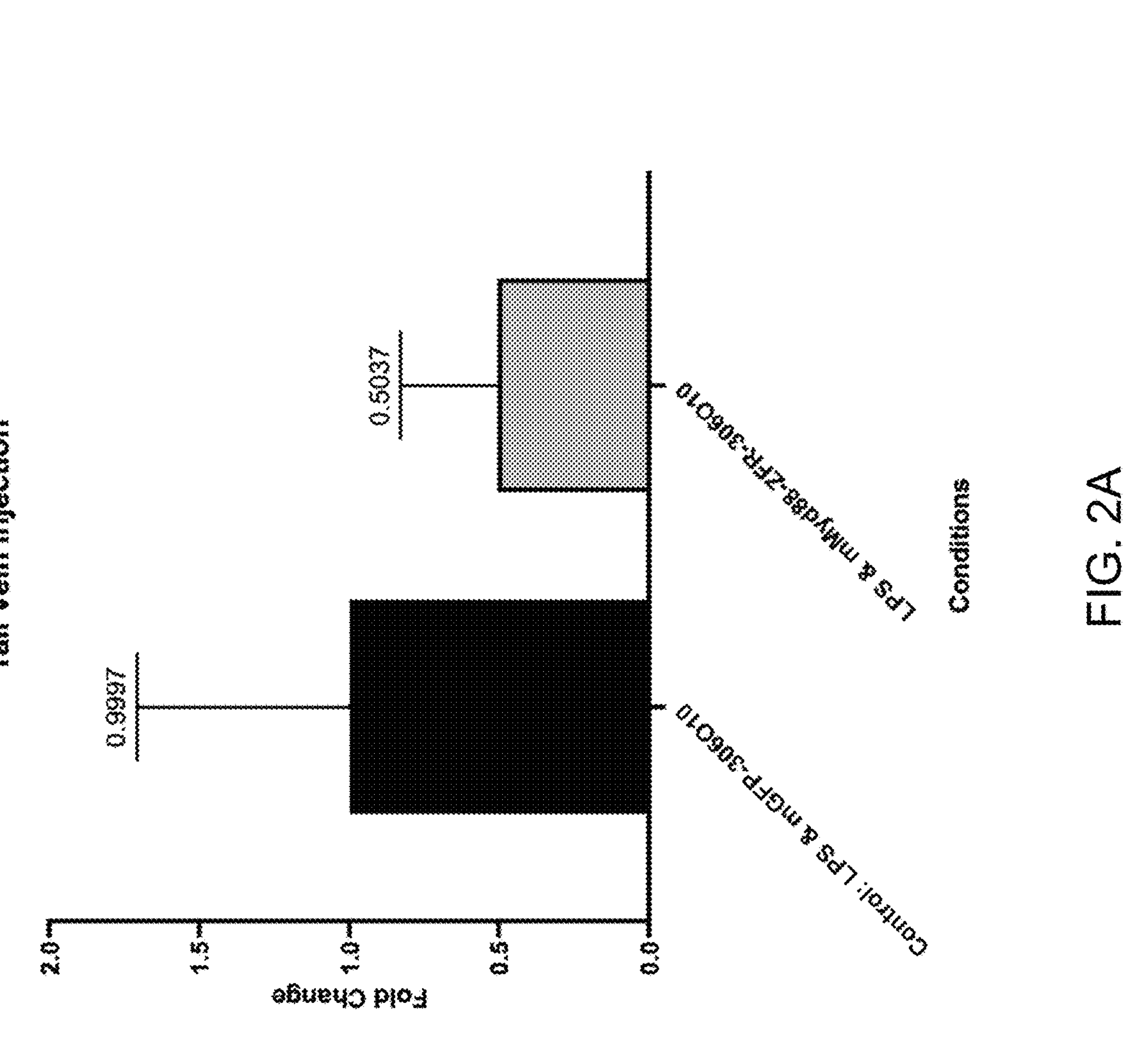
FIGS. 2A-2E are graphs showing the fold change in MYD88 transcript levels (as measured by qPCR) in mice treated with LPS and either (i) mGFP-306$O_{10}$ or (ii)
Figure 2B:
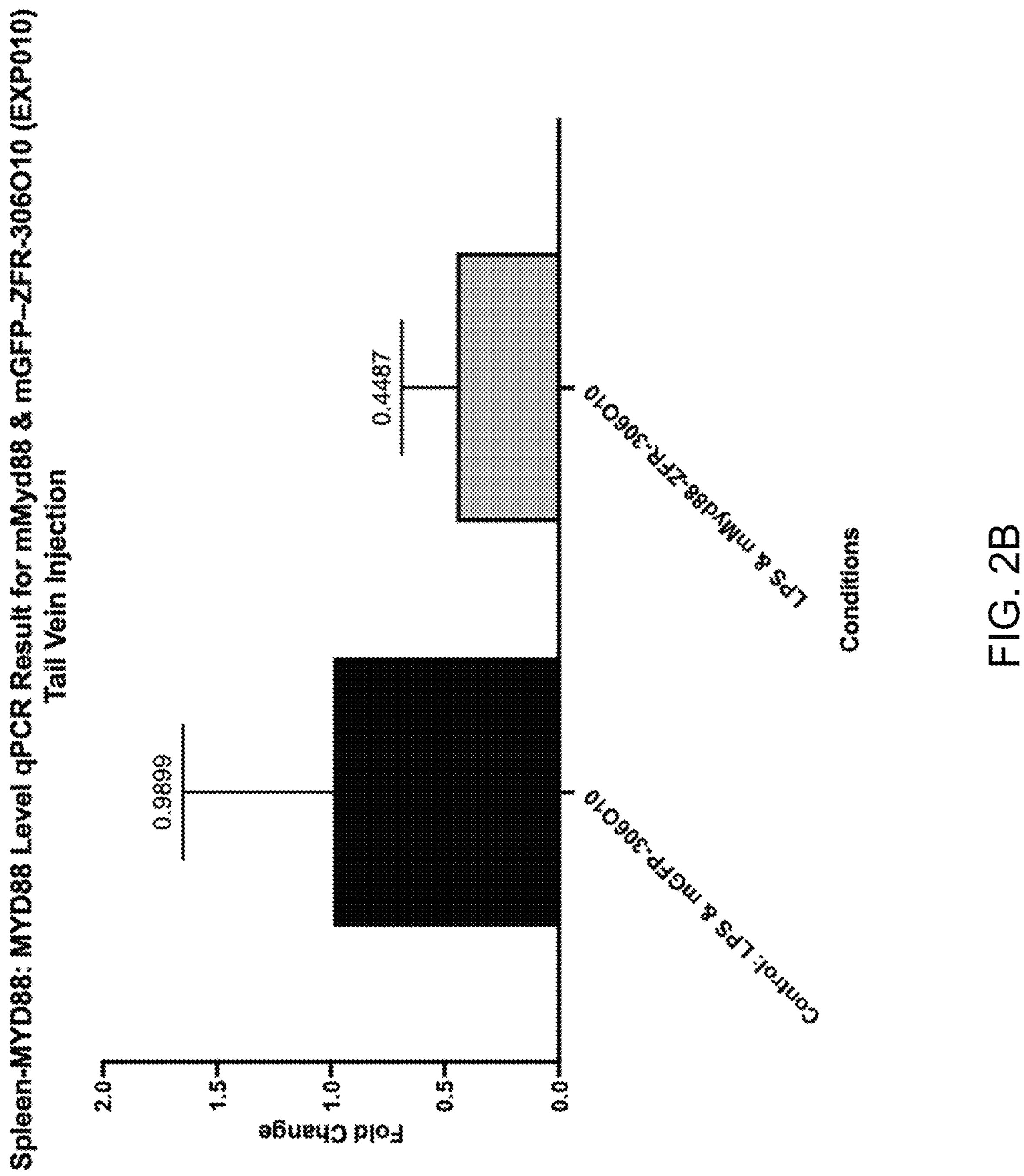
Figure 2C:
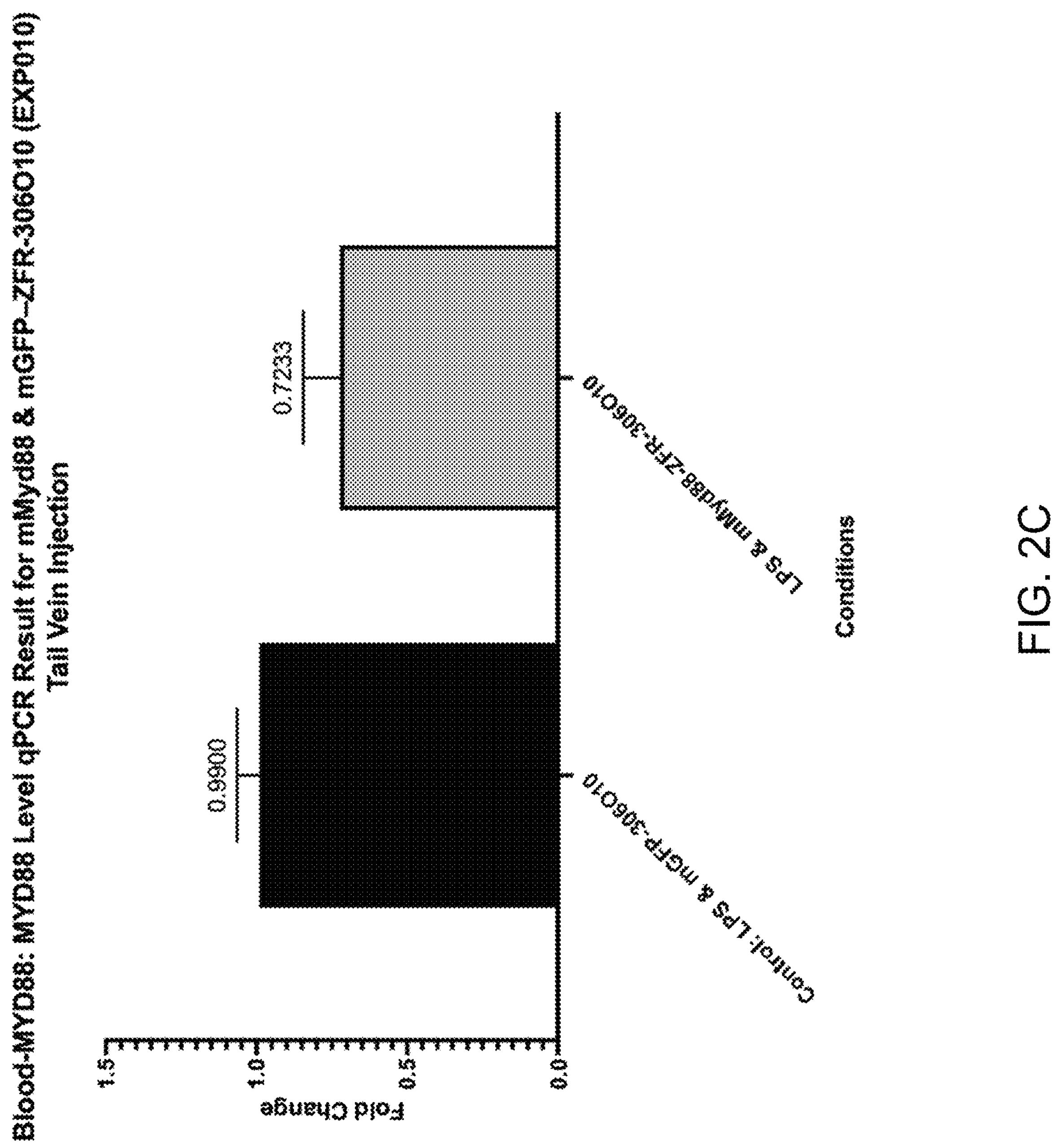
Figure 2D:
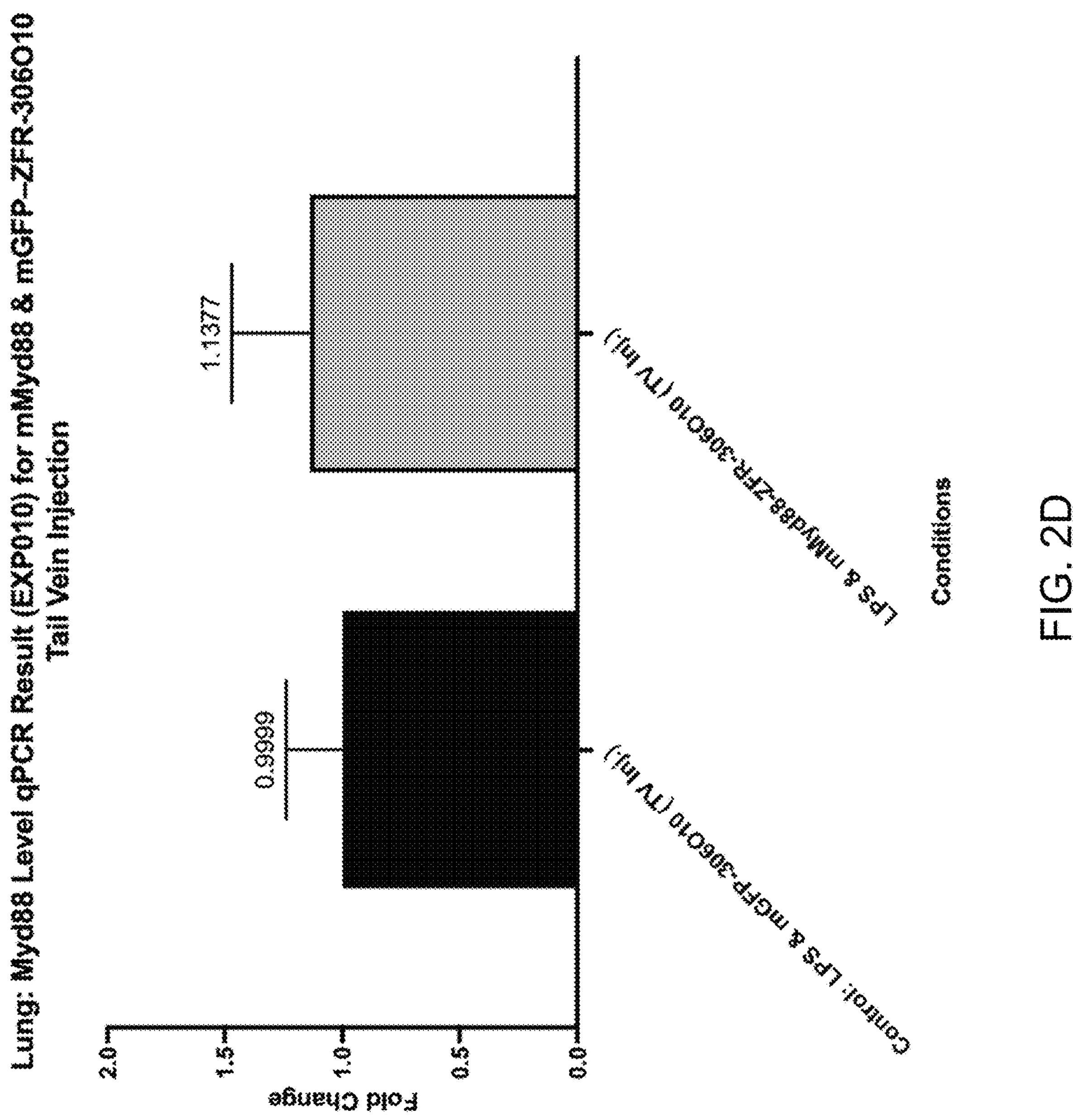
Figure 2E:
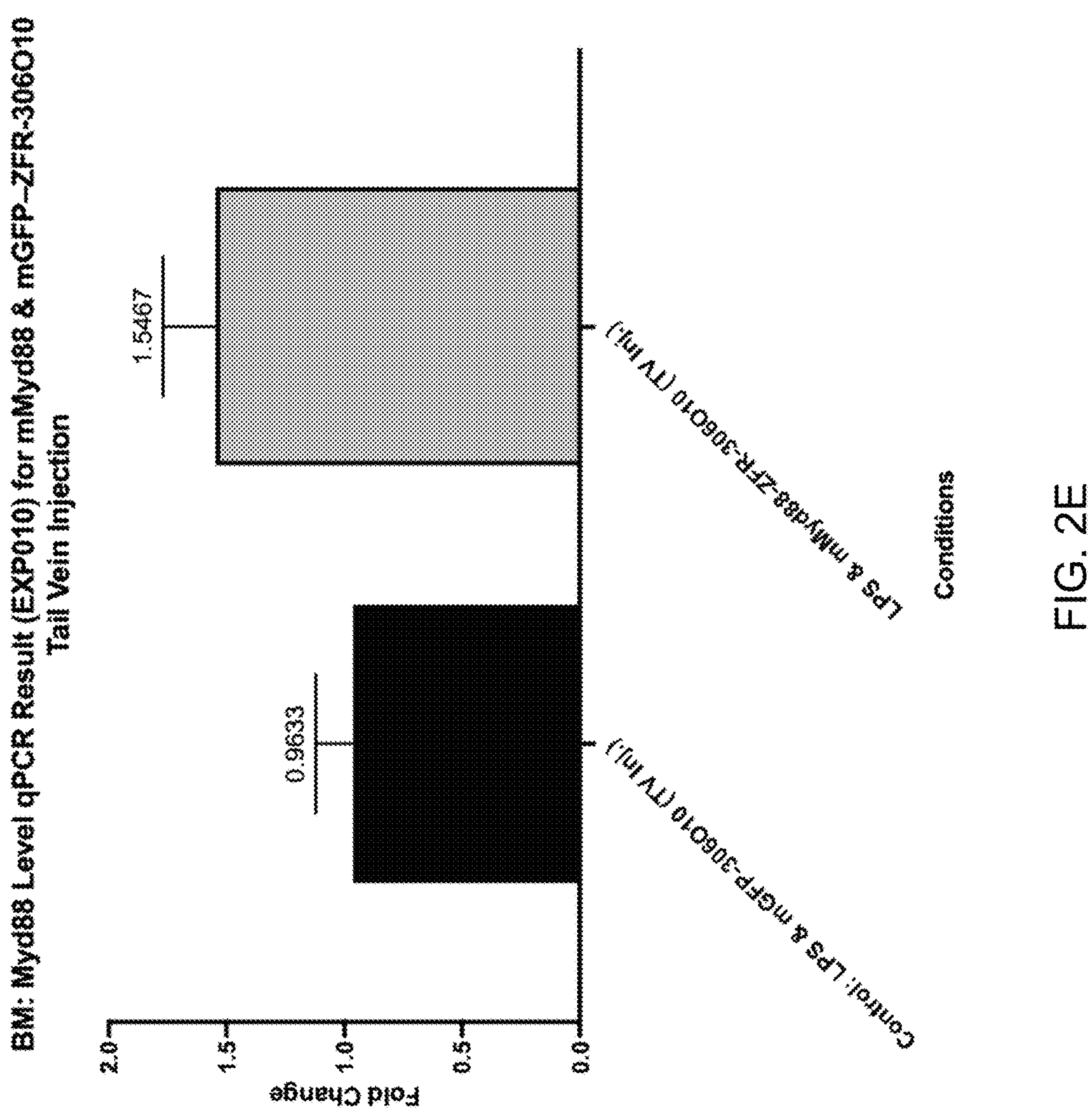
Figure 3A:
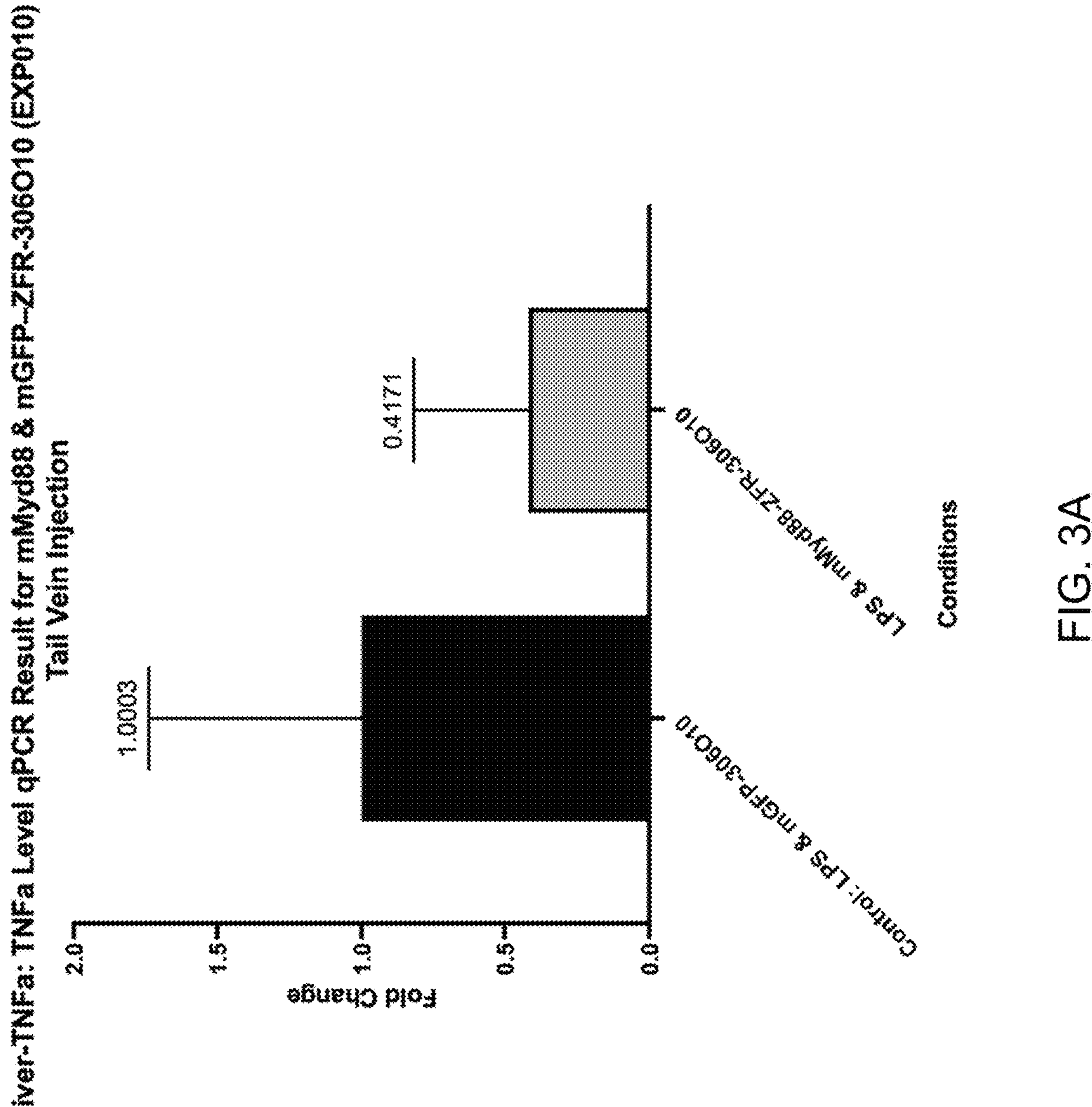
Figure 3B:
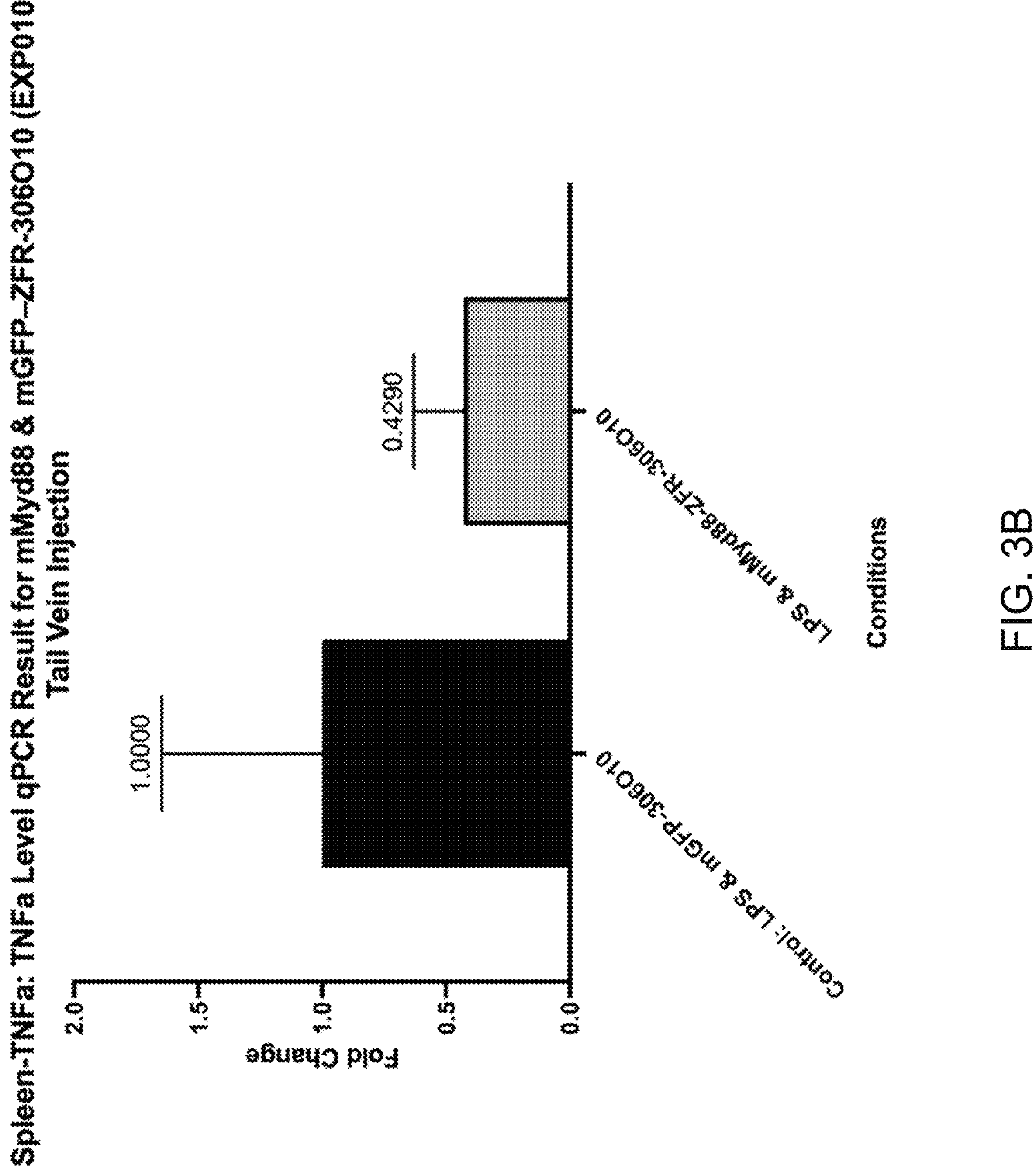
Figure 3C:
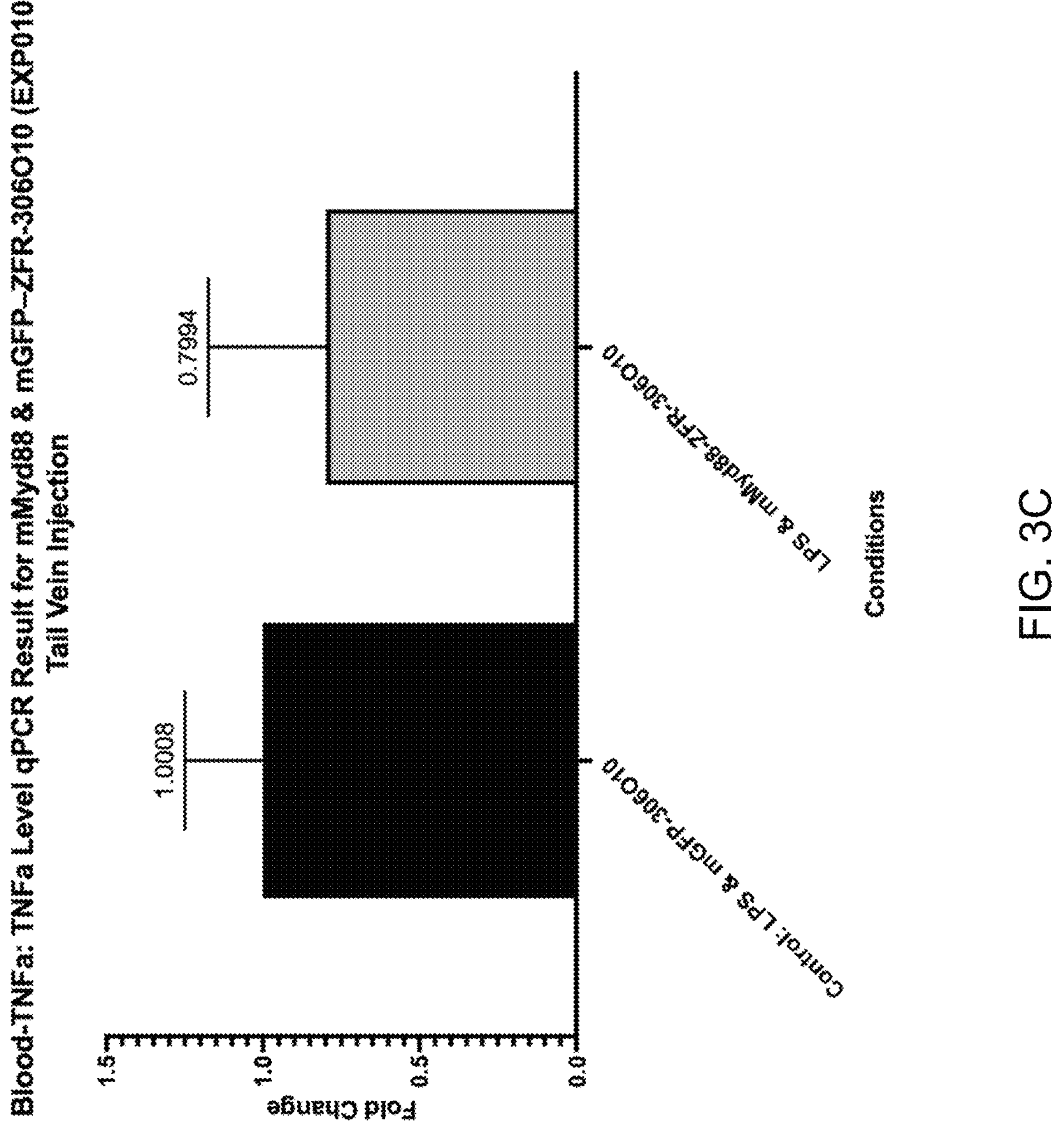
Figure 3D:
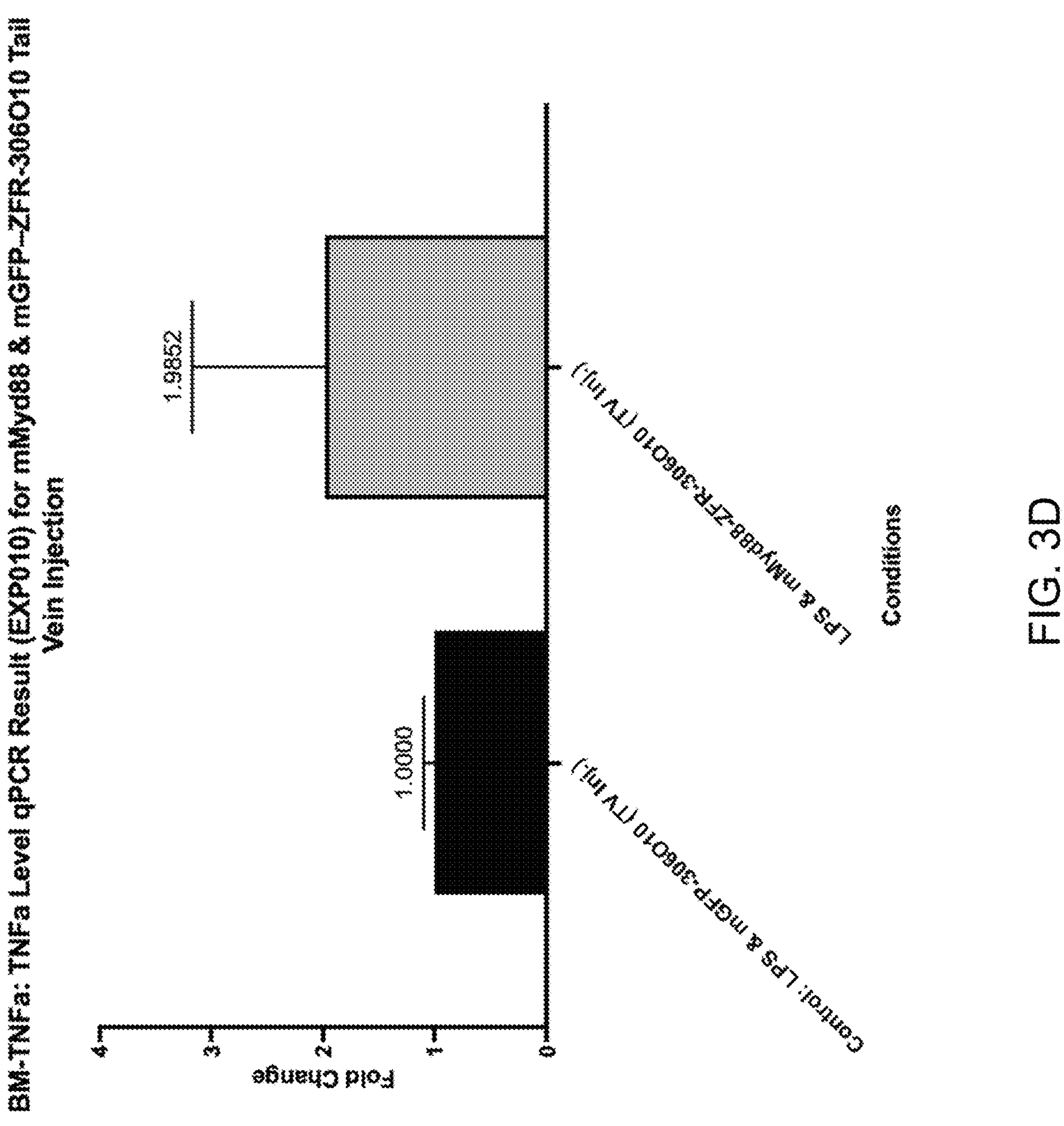
Figure 4A:
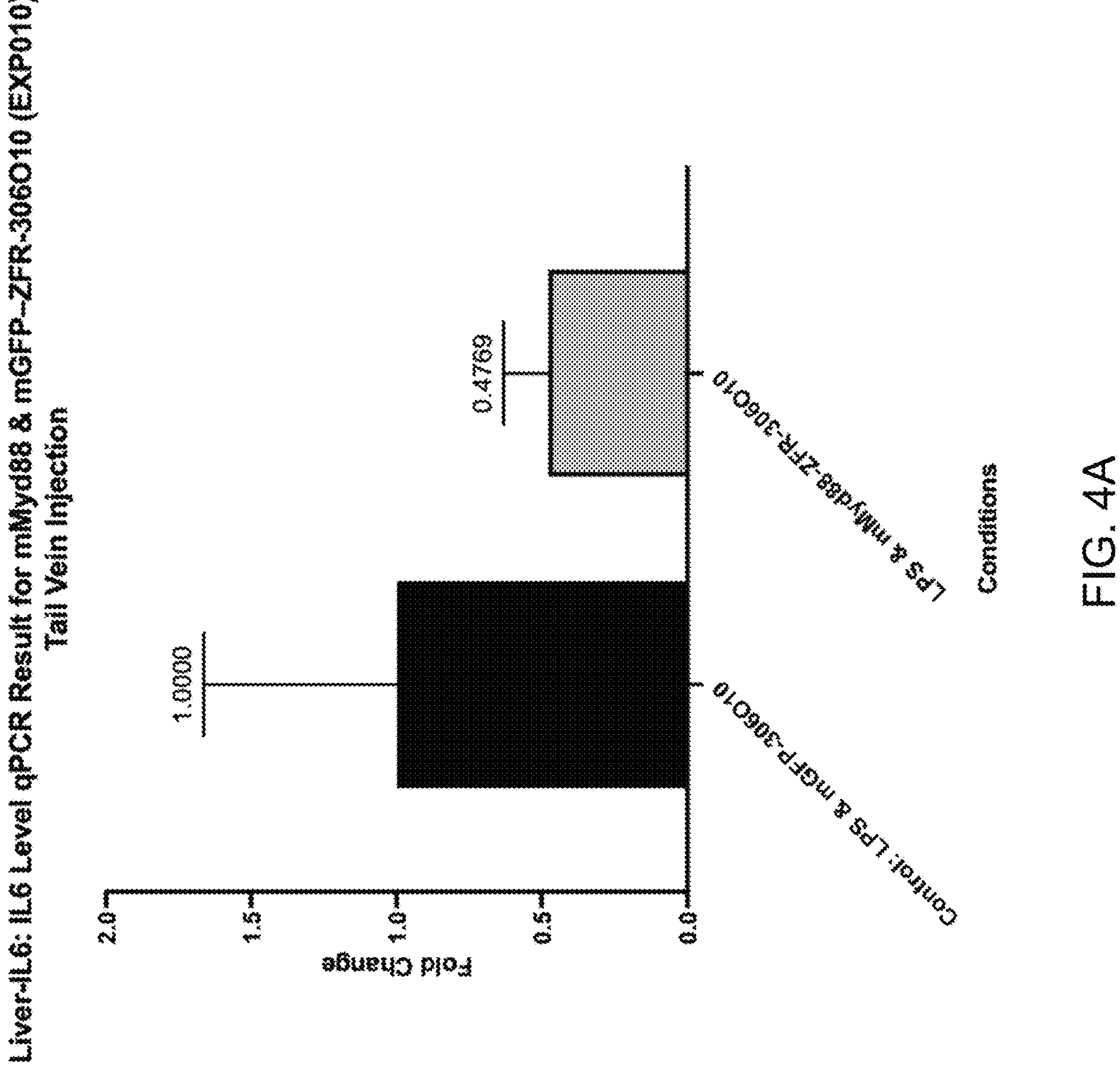
Figure 4B:
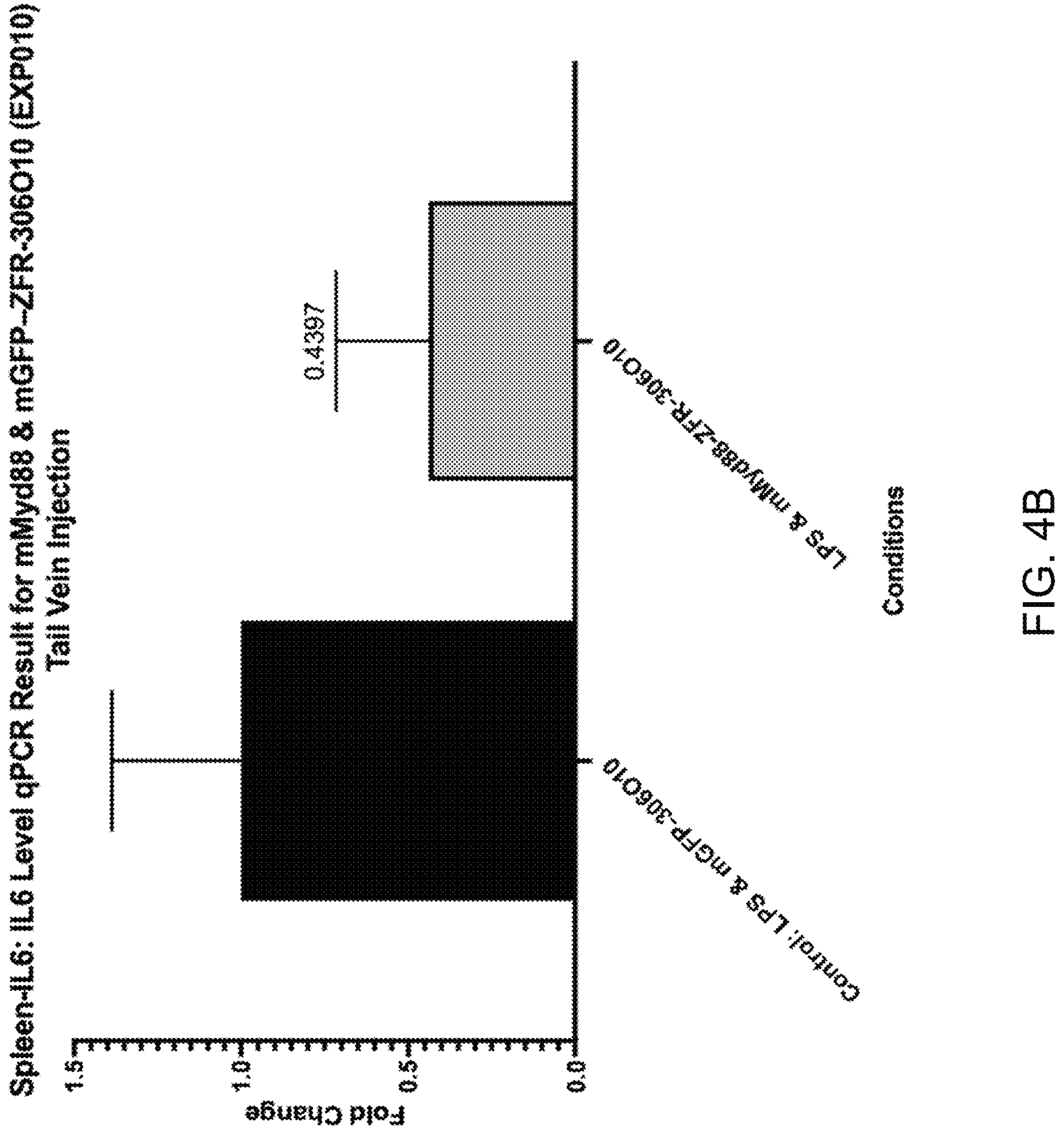
Figure 4C:
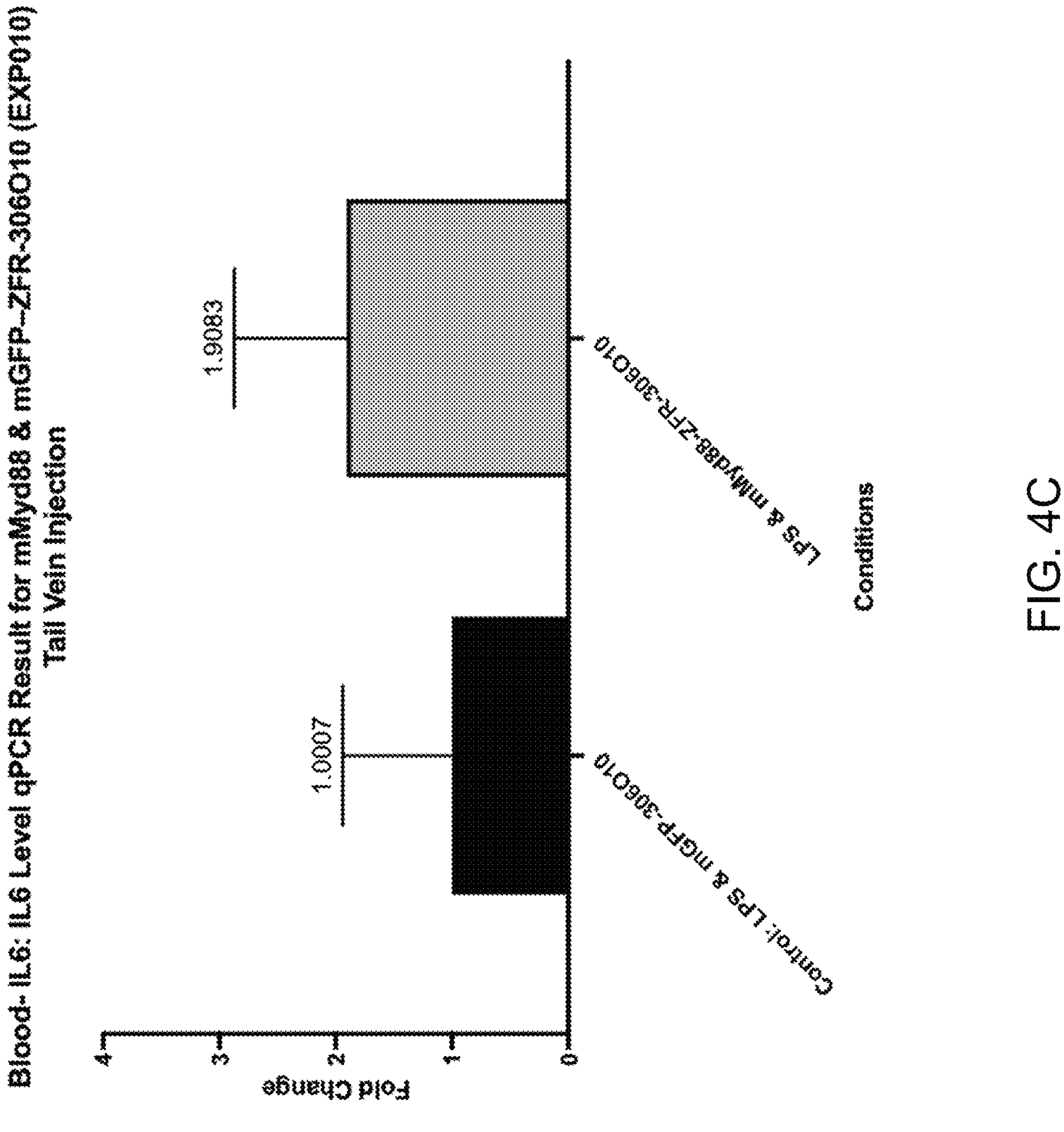
Figure 4D:
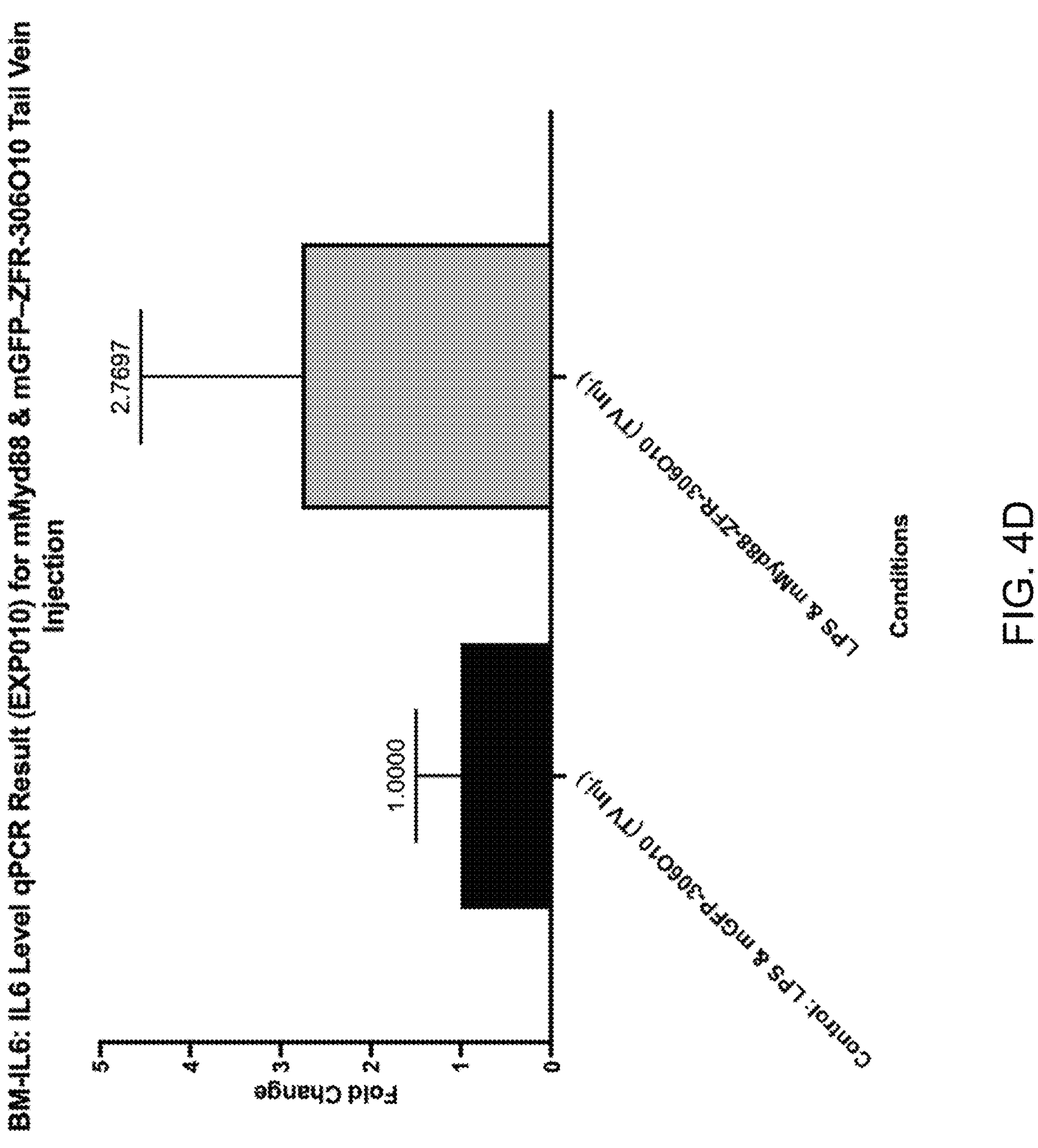

The results are set forth in FIG. 1. Based on the qPCR results in FIG. 1, ZFR11 (SEQ ID NO: 10) and ZFR3 (SEQ ID NO: 11) resulted in the best repression for Myd88 gene, which are 0.21 and 0.22, respectively. The repression result achieved with ZFRs is comparable to or even more efficient than the one with CRISPR's Cas9, which is 0.236 (Myd88-g1 14 nt condition) (see FIG. 1).

These results demonstrate that zinc finger proteins can be used to effectively target sequences (e.g., the promoter region of Myd88) in subjects.

Example 2

This example demonstrates that a zinc finger protein that specifically binds to the promoter region of the Myd88 gene reduces lipopolysaccharide (LPS)-induced inflammation in mice.

Mice (about 6 weeks of age) were injected with 2.5 mg/kg of LPS (intraperitoneal (IP) injection). Two hours later, the mice were injected with mGFP-306$O_{10}$ lipid nanoparticle (LNP) (control) or ZFR11 (SEQ ID NO: 10) of Example 1 (mMYD88-ZFR-306$O_{10}$) LNP (experimental sample) through the tail vain (dosage: 1.6 mg RNA/kg mouse). The LNPs had the structure of LNP 306$O_{10}$, as described in Hajj et al., *Small.*, 15 (6): e1805097 (2019). After 25-30 hours, cytokines and Myd88 levels were assessed. There were three mice in the control group and three mice in the experimental group.

The results are shown in FIGS. 2A-2E (MYD88 qPCR), 3A-3D (TNF alpha qPCR), 4A-4D (IL-6 qPCR), 5A-5C (NCF qPCR), 6A-6C (ILIB qPCR), and 7A-7B (ICAM1 qPCR). A significant level of MYD88 transcript repression was observed in spleen and liver in the experimental samples as compared to control. Slight MYD88 repression was observed in blood (around 30%) in the experimental samples as compared to control. No repression was observed for the MYD88 transcript level in lung and bone marrow in the experimental samples as compared to control.

Example 3

This example demonstrates that a zinc finger protein that specifically binds to the promoter region of the Myd88 gene reduces adeno-associated viral (AAV) vector-induced inflammation in mice.

For the experimental group, mice were injected with 1.5 mg/kg of LNP of an AAV1-CMV (cytomegalovirus)-Cas9 vector and LNP of ZFR11 (SEQ ID NO: 10) of Example 1 (mMYD88-ZFR-306$O_{10}$) (IP) at the time points shown in the schematic of FIG. 8. Blood was drawn at the time points shown in FIG. 8, and MYD88 transcript levels were assessed by qPCR in blood, lung, spleen, and liver.

For the control group, mice were injected with 1.5 mg/kg of LNP of an AAV1-CMV-Cas9 vector, Mock-gRNA-306$O_{10}$ LNP, and mLuciferase-306$O_{10}$ LNP (IP) at the time points shown in the schematic of FIG. 9. Blood was drawn at the time points shown in FIG. 9, and MYD88 transcript levels were assessed by qPCR in blood, lung, spleen, and liver.

The results are shown in FIGS. 10A-10D. A significant level of MYD88 transcript repression was observed in blood. Slight MYD88 repression was observed in lung. No repression was observed for the MYD88 transcript level in spleen and liver in the experimental samples as compared to control.

MYD88 transcript levels were assessed by qPCR in blood for both the control group (FIG. 26) and the experimental group (FIG. 27) at various time points before and after AAV1 vector administration. The average level of MYD88 transcript at harvest (10 days after second AAV1 administration) in experimental and control samples (both relative to the baseline level) was 0.113 and 0.409, respectively. This means that the average final level of MYD88 transcript in the experimental group compared to the control group was 0.28 (0.113/0.409), which was a 0.72 reduction in MYD88 transcript level on average.

Example 4

This example demonstrates a protocol for controlling specific adaptive immunity to gene therapy viruses or other foreign antigens.

In some instances, to control specific adaptive immunity to gene therapy viruses or other foreign antigen, a combinatorial regimen will be used. Myd88 repressing reagents, such as the zinc finger proteins described in Examples 1-3, will be delivered to mice combined with viral antigen. On some occasions, mRNA encoding for the zinc finger protein will be packaged with mRNA encoding for the viral antigen (i.e. VP1 coat protein for AAV) within lipid nanoparticles and delivered systemically or intramuscularly, intranasally, intradermally, or subcutaneously to mice. On some occasions, rapacymin, an mTOR inhibitor, will be co-packaged with mRNA/LNPs or in a separate LNP and will be co-delivered to the mice. These reagents can be used as a tolerogenic vaccine therapeutically or prophylactically.

Example 5

This example demonstrates that zinc finger proteins repress Myd88 expression in a mouse B cell lymphoma cell line.

Either mGFP-306$O_{10}$ LNP (control) or ZFR11 (SEQ ID NO: 10) of Example 1 (mMYD88-ZFR-306$O_{10}$) LNP (experimental sample) were transfected into mouse B cell lymphoma cell line (CH27 cells) in vitro (FIG. 11A). In a separate experiment, either mGFP-3060$_{i10}$ LNP (control) or ZFR11 (SEQ ID NO: 10) of Example 1 (mMYD88-ZFR-3060$_{i10}$) LNP (experimental sample) were transfected into CH27 cells in vitro (FIG. 11B). The LNPs had the structure of LNP 306$O_{10}$ or LNP 3060$_{i10}$, as described in Hajj et al., *Small.*, 15 (6): e1805097 (2019). The 306$O_{10}$ and 306$O_{i10}$ lipidoids, which have 10-carbon tails and identical molecular weights, vary only in that the 306$O_{10}$ tail is straight and the 306$O_{i10}$ tail has a one-carbon branch. Transfection was performed with Lipo LTX. RNA was extracted after the transfection and cDNA synthesized, followed by qPCR. The results showed that the zinc finger protein repressed Myd88 expression (FIGS. 11A-11B).

Example 6

This example demonstrates that a zinc finger protein that specifically binds to the promoter region of the Myd88 gene reduces Myd88 expression in mice.

Mice were injected with 2.5 mg/kg of LPS (IP injection). Two hours later, the mice were injected with mGFP-306$O_{10}$ LNP (control) or ZFR11 (SEQ ID NO: 10) of Example 1 (mMYD88-ZFR-306$O_{10}$) LNP (experimental sample) through the tail vain (dosage: 1.6 mg RNA/kg mouse). After 25-30 hours, Myd88 levels were assessed in liver (FIG. 12A) and in blood (FIG. 12B). As shown in FIGS. 12A-12B, mMYD88-ZFR-306$O_{10}$ decreased the Myd88 level in liver and blood up to 46% as compared to control.

Example 7

This example demonstrates that a zinc finger protein that specifically binds to the promoter region of the Myd88 gene reduces expression of downstream cytokines in mice.

Mice were injected with LPS and either (i) mGFP-306$O_{10}$ LNP (control) or (ii) ZFR11 (SEQ ID NO: 10) of Example 1 (mMYD88-ZFR-306$O_{10}$) LNP (experimental sample) as described in Example 6. After 25-30 hours, levels of TNF alpha and IL-6 were assessed in blood and liver. As shown in FIGS. 13A-13D, mMYD88-ZFR-306$O_{10}$ decreased the levels of TNF alpha and IL-6 in liver and blood as compared to control.

Example 8

This example demonstrates that a zinc finger protein that specifically binds to the promoter region of the Myd88 gene reduces Myd88 and cytokine transcript levels in mouse spleen.

Mice (about 7 weeks of age) were injected with 2.5 mg/kg of LPS (IP injection). Two hours later, the mice were injected with mGFP-306$O_{i10}$ LNP (control) or ZFR11 (SEQ ID NO: 10) of Example 1 (mMYD88-ZFR-3060$_{i10}$) LNP (experimental sample) through the tail vain (dosage: 1.6 mg RNA/kg mouse). There were three mice in the control group and three mice in the experimental group. After 25-30 hours, Myd88 and cytokine (TNF alpha, IL-6, NCF, ICAM1, and IL-1B) transcript levels were assessed by qPCR in spleen (FIGS. 14A-14F) and liver (FIGS. 15A-15F).

Significant repression was observed for Myd88 and cytokine transcript levels in spleen experimental samples as compared to control (FIGS. 14A-14F). No consistent repression was observed for Myd88 or cytokine transcript levels in liver experimental samples as compared to control (FIGS. 15A-15F).

Example 9

This example demonstrates expression of zinc finger proteins as measured by FACS.

Either DNA plasmid (control) or ZFR11 (SEQ ID NO: 10) of Example 1 (mMYD88-ZFR-306$O_{10}$) LNP (experimental sample) were transfected into CH27 cells in vitro, as set forth in Table 2.

TABLE 2

| | LNP volume to be added to cell culture | Sample No. |
|---|---|---|
| 10X concentration of 0.1 mg/mL (final concentration 0.01 mg/mL) mMYD88-ZFR-306$O_{10}$ LNP | 100 μL LNP in 1 mL cell culture | A1 and A2 |
| transfection with DNA plasmid | not applicable | J1 and J2 |

Cells were unstained or stained with PE-conjugated anti-FLAG antibodies. Fluorescence-activated cell sorting (FACS) was carried on unstained cells, cells that were stained but untransfected, or cells that were stained and transfected. PE indicated the presence of anti-FLAG zinc finger protein. Pacific blue dye indicated presence of live cell populations. The results are shown in FIGS. 16A-16B, 17A-17B, 18A-18B, and 19A-19B. High background was observed in the FACs results. The stained experimental sample and stained untransfected sample appeared similar in the FACs results. It is believed that these FACS results may be due to the unspecific PE anti-FLAG antibody. It is also possible that the zinc finger protein expression detected with respect to the mMYD88-ZFR-306$O_{10}$ LNP was low because it was not codon optimized.

Example 10

This example demonstrates that a zinc finger protein that specifically binds to the promoter region of the Myd88 gene reduces AAV vector-induced inflammation in mice.

For the experimental group, mice were injected with 0.75 mg/kg of LNP of an AAV1-CMV (cytomegalovirus)-Cas9 vector and LNP of ZFR11 (SEQ ID NO: 10) of Example 1 (mMYD88-ZFR-306$O_{10}$) (IP) at the time points shown in the schematic of FIG. 20. Blood was drawn at the time points shown in FIG. 20, and MYD88 transcript levels were assessed by qPCR in blood, lung, spleen, and liver.

For the control group, mice were injected with 0.75 mg/kg of LNP of an AAV1-CMV-Cas9 vector, Mock-gRNA-306$O_{10}$ LNP, and mLuciferase-306$O_{10}$ LNP (IP) at the time points shown in the schematic of FIG. 21. Blood was drawn at the time points shown in FIG. 21, and MYD88 transcript levels were assessed by qPCR in blood, lung, spleen, and liver.

The results are shown in FIGS. 22A-22B and 23A-23B. A significant level of MYD88 transcript repression was observed in blood. Slight MYD88 repression was observed in lung. No repression was observed for the MYD88 transcript level in spleen and liver in the experimental samples as compared to control.

MYD88 transcript levels were assessed by qPCR in blood for both the control group (FIG. 24) and the experimental group (FIG. 25) at various time points before and after AAV1 vector administration. The average level of MYD88 transcript at harvest (10 days after 2nd AAV vector administration) in experimental and control samples (both relative to the baseline level) were 0.23 and 0.183, respectively. This showed no decrease in the average final level of MYD88 transcription in experimental group as compared to control group.

Example 11

This example demonstrates that a zinc finger protein that specifically binds to the promoter region of the Myd88 gene reduces AAV vector-induced inflammation in mice.

For the experimental group, mice were injected with a single AAV1-Shef1a-MYD88-ZFR11 vector, wherein the MYD88-ZFR11 was ZFR11 (SEQ ID NO: 10) of Example 1 at the time point shown in the schematic of FIG. 28. Blood was drawn at the time points shown in FIG. 28, and MYD88 transcript levels were assessed by qPCR in blood, lung, spleen, and liver.

For the control group, mice were injected with a single AAV1-Mock-gRNA vector at the time point shown in the schematic of FIG. 29. Blood was drawn at the time points shown in FIG. 29, and MYD88 transcript levels were assessed by qPCR in blood, lung, spleen, and liver.

The results are shown in FIGS. 30A-30B, 31A-31B, 32A-32B, and 33A-33B. In blood, 30% MYD88 repression was observed in experimental as compared to control. In liver, 40% MYD88 repression was observed in experimental as compared to control.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

SEQUENCE LISTING

SEQ ID NO: 1 (N-terminal fixed)
LEPGEKP

SEQ ID NO: 2 (N-terminal backbone)
YKCPECGKSFS

SEQ ID NO: 3 (C-terminal backbone)
HQRTH

SEQ ID NO: 4 (ZF linker)
TGEKP

SEQ ID NO: 5 (C-terminal fixed)
TGKKTS

SEQ ID NO: 6 (Zinc Finger 3)
ATGGACTACAAAGACCATGACGGTGATTATAAAGATCATGACATCGATTACAAG
GATGACGATGACAAGATGGCCCCCAAGAAGAAGAGGAAGGTCGGCATTCATGG
GGTACCCGCCGCTATGGCTGAGAGGCCCTTCCAGTGTCGAATCTGCATGCGTAAC
TTCAGTCGCTCCGACCACCTGTCCCGCCACATCCGCACCCACACCGGCGAGAAGC
CTTTTGCCTGTGACATTTGTGGGAGGAAATTTGCCGACCGCTCCGTGCTGGCCCG
CCATACCAAGATACACACGGGCAGCCAAAAGCCCTTCCAGTGTCGAATCTGCAT
GCGTAACTTCAGTGACCGCTCCCACCTGACCCGCCACATCCGCACCCACACCGGC
GAGAAGCCTTTTGCCTGTGACATTTGTGGGAGGAAATTTGCCGACCGCTCCAACC
TGACCCGCCATACCAAGATACACACGGGATCTCAGAAGCCCTTCCAGTGTCGAAT
CTGCATGCGTAACTTCAGTCGCTCCGACGTGCTGTCCGAGCACATCCGCACCCAC
ACCGGCGAGAAGCCTTTTGCCTGTGACATTTGTGGGAGGAAATTTGCCCAGTCCG
GCTCCCTGACCCGCCATACCAAGATACACCTGCGCCAAAAAGATGCGGCCCGGG
GATCC SEQ ID NO: 7 (Zinc Finger 11)
ATGGACTACAAAGACCATGACGGTGATTATAAAGATCATGACATCGATTACAAG
GATGACGATGACAAGATGGCCCCCAAGAAGAAGAGGAAGGTCGGCATCCACGG
GGTACCCGCCGCTATGGCTGAGAGGCCCTTCCAGTGTCGAATCTGCATGCGTAAC
TTCAGTGACCGCTCCGCCCTGTCCCGCCACATCCGCACCCACACCGGCGAGAAGC
CTTTTGCCTGTGACATTTGTGGGAGGAAATTTGCCCGCTCCGACCACCTGTCCCG
CCATACCAAGATACACACGGGCAGCCAAAAGCCCTTCCAGTGTCGAATCTGCAT
GCGTAACTTCAGTCGCTCCGACGACCTGACCCGCCACATCCGCACCCACACCGGC
GAGAAGCCTTTTGCCTGTGACATTTGTGGGAGGAAATTTGCCGACCGCTCCAACC
TGAAGGCCCATACCAAGATACACACGGGATCTCAGAAGCCCTTCCAGTGTCGAA
TCTGCATGCGTAACTTCAGTGACTCCTCCGACCGCAAGAAGCACATCCGCACCCA
CACCGGCGAGAAGCCTTTTGCCTGTGACATTTGTGGGAGGAAATTTGCCCAGTC SEQ ID NO: 8 (Hp1a)
AGCCCCAAGAAAAAACGGAAAGTGGAGGCATCAATGAAGGAGGGAGAAAACAA
CAAACCCAGGGAGAAAAGTGAAGGGAATAAGAGAAAAAGCTCCTTCTCTAACA
GTGCAGACGATATCAAGTCCAAGAAAAAGCGGGAGCAGTCTAATGACATTGCTA
GGGGCTTCGAGAGAGGACTGGAGCCAGAAAAAATCATTGGGGCAACCGACAGCT
GCGGCGATCTGATGTTTCTCATGAAATGGAAGGACACAGATGAGGCCGACCTGG
TGCTCGCCAAAGAAGCTAACGTGAAGTGTCCCCAGATCGTCATTGCTTTTTACGA
GGAAAGGCTCACCTGGCACGCATATCCTGAGGATGCCGAAAACAAGGAGAAGG
AATCAGCTAAGAGC SEQ ID NO: 9 (krab)
ATGGACGCGAAATCACTTACGGCATGGTCGAGAACACTGGTTACGTTCAAGGAC
GTGTTTGTGGACTTTACACGTGAGGAGTGGAAATTGCTGGATACTGCGCAACAAA
TTGTGTATCGAAATGTCATGCTTGAGAATTACAAGAACCTCGTCAGTCTCGGATA
CCAGTTGACGAAACCGGATGTGATCCTTAGGCTCGAAAAGGGGGAAGAACCTTG
GCTGGTA SEQ ID NO: 10 (Zinc Finger 3 - *HP1α*-krab)
ATGGACTACAAAGACCATGACGGTGATTATAAAGATCATGACATCGATTACA
AGGATGACGATGACAAGATGGCCCCCAAGAAGAAGAGGAAGGTCGGCATTC
ATGGGGTACCCGCCGCTATGGCTGAGAGGCCCTTCCAGTGTCGAATCTGCA
TGCGTAACTTCAGTCGCTCCGACCACCTGTCCCGCCACATCCGCACCCACAC
CGGCGAGAAGCCTTTTGCCTGTGACATTTGTGGGAGGAAATTTGCCGACCG

SEQUENCE LISTING

CTCCGTGCTGGCCCGCCATACCAAGATACACACGGGCAGCCAAAAGCCCTT
CCAGTGTCGAATCTGCATGCGTAACTTCAGTGACCGCTCCCACCTGACCCGC
CACATCCGCACCCACACCGGCGAGAAGCCTTTTGCCTGTGACATTTGTGGG
AGGAAATTTGCCGACCGCTCCAACCTGACCCGCCATACCAAGATACACACG
GGATCTCAGAAGCCCTTCCAGTGTCGAATCTGCATGCGTAACTTCAGTCGCT
CCGACGTGCTGTCCGAGCACATCCGCACCCACACCGGCGAGAAGCCTTTTG
CCTGTGACATTTGTGGGAGGAAATTTGCCCAGTCCGGCTCCCTGACCCGCC
ATACCAAGATACACCTGCGCCAAAAAGATGCGGCCCGGGGATCCCCATGGCC
CAAGAAGAAGAGGAAGGTGAGTGGTGGAGGAAGTGGCGGGTCAGGGTCG*AGCC*
*CCAAGAAAAAACGGAAAGTGGAGGCATCAATGAAGGAGGGAGAAAACAACAAACCCAG*
*GGAGAAAAGTGAAGGGAATAAGAGAAAAAGCTCCTTCTCTAACAGTGCAGACGATATC*
*AAGTCCAAGAAAAAGCGGGAGCAGTCTAATGACATTGCTAGGGGCTTCGAGAGAGGAC*
*TGGAGCCAGAAAAAATCATTGGGGCAACCGACAGCTGCGGCGATCTGATGTTTCTCAT*
*GAAATGGAAGGACACAGATGAGGCCGACCTGGTGCTCGCCAAAGAAGCTAACGTGAA*
*GTGTCCCCAGATCGTCATTGCTTTTTACGAGGAAAGGCTCACCTGGCACGCATATCCT*
*GAGGATGCCGAAAACAAGGAGAAGGAATCAGCTAAGAGC*TCGGGAGGTGGTTCGGG
TGGCTCTGGATCAATGGACGCGAAATCACTTACGGCATGGTCGAGAACACTGGTT
ACGTTCAAGGACGTGTTTGTGGACTTTACACGTGAGGAGTGGAAATTGCTGGATA
CTGCGCAACAAATTGTGTATCGAAATGTCATGCTTGAGAATTACAAGAACCTCGT
CAGTCTCGGATACCAGTTGACGAAACCGGATGTGATCCTTAGGCTCGAAAAGGG
GGAAGAACCTTGGCTGGTATAG

SEQ ID NO: 11 (Zinc Finger 11 - *HP1α*-krab)
ATGGACTACAAAGACCATGACGGTGATTATAAAGATCATGACATCGATTACA
AGGATGACGATGACAAGATGGCCCCCAAGAAGAAGAGGAAGGTCGGCATCC
ACGGGGTACCCGCCGCTATGGCTGAGAGGCCCTTCCAGTGTCGAATCTGCA
TGCGTAACTTCAGTGACCGCTCCGCCCTGTCCCGCCACATCCGCACCCACAC
CGGCGAGAAGCCTTTTGCCTGTGACATTTGTGGGAGGAAATTTGCCCGCTC
CGACCACCTGTCCCGCCATACCAAGATACACACGGGCAGCCAAAAGCCCTT
CCAGTGTCGAATCTGCATGCGTAACTTCAGTCGCTCCGACGACCTGACCCGC
CACATCCGCACCCACACCGGCGAGAAGCCTTTTGCCTGTGACATTTGTGGG
AGGAAATTTGCCGACCGCTCCAACCTGAAGGCCCATACCAAGATACACACG
GGATCTCAGAAGCCCTTCCAGTGTCGAATCTGCATGCGTAACTTCAGTGACT
CCTCCGACCGCAAGAAGCACATCCGCACCCACACCGGCGAGAAGCCTTTTG
CCTGTGACATTTGTGGGAGGAAATTTGCCCAGTCCGGCCACCTGTCCCGCC
ATACCAAGATACACCTGCGCCAAAAAGATGCGGCCCGGGGATCCCCATGGCC
CAAGAAGAAGAGGAAGGTGAGTGGTGGAGGAAGTGGCGGGTCAGGGTCG*AGCC*
*CCAAGAAAAAACGGAAAGTGGAGGCATCAATGAAGGAGGGAGAAAACAACAAACCCAG*
*GGAGAAAAGTGAAGGGAATAAGAGAAAAAGCTCCTTCTCTAACAGTGCAGACGATATC*
*AAGTCCAAGAAAAAGCGGGAGCAGTCTAATGACATTGCTAGGGGCTTCGAGAGAGGAC*
*TGGAGCCAGAAAAAATCATTGGGGCAACCGACAGCTGCGGCGATCTGATGTTTCTCAT*
*GAAATGGAAGGACACAGATGAGGCCGACCTGGTGCTCGCCAAAGAAGCTAACGTGAA*
*GTGTCCCCAGATCGTCATTGCTTTTTACGAGGAAAGGCTCACCTGGCACGCATATCCT*
*GAGGATGCCGAAAACAAGGAGAAGGAATCAGCTAAGAGC*TCGGGAGGTGGTTCGGG
TGGCTCTGGATCAATGGACGCGAAATCACTTACGGCATGGTCGAGAACACTGGTT
ACGTTCAAGGACGTGTTTGTGGACTTTACACGTGAGGAGTGGAAATTGCTGGATA
CTGCGCAACAAATTGTGTATCGAAATGTCATGCTTGAGAATTACAAGAACCTCGT
CAGTCTCGGATACCAGTTGACGAAACCGGATGTGATCCTTAGGCTCGAAAAGGG
GGAAGAACCTTGGCTGGTATAG SEQ ID NO: 12 (Myd88 promoter target site)
GGA GGG GGA GGA AGG GGG SEQ ID NO: 13 (*HP1α*-krab effector)
*AGCCCCAAGAAAAAACGGAAAGTGGAGGCATCAATGAAGGAGGGAGAAAACAACAAAC*
*CCAGGGAGAAAAGTGAAGGGAATAAGAGAAAAAGCTCCTTCTCTAACAGTGCAGACGA*
*TATCAAGTCCAAGAAAAAGCGGGAGCAGTCTAATGACATTGCTAGGGGCTTCGAGAGA*
*GGACTGGAGCCAGAAAAAATCATTGGGGCAACCGACAGCTGCGGCGATCTGATGTTTC*
*TCATGAAATGGAAGGACACAGATGAGGCCGACCTGGTGCTCGCCAAAGAAGCTAACGT*
*GAAGTGTCCCCAGATCGTCATTGCTTTTTACGAGGAAAGGCTCACCTGGCACGCATAT*
*CCTGAGGATGCCGAAAACAAGGAGAAGGAATCAGCTAAGAGC*TCGGGAGGTGGTTCG
GGTGGCTCTGGATCAATGGACGCGAAATCACTTACGGCATGGTCGAGAACACTG
GTTACGTTCAAGGACGTGTTTGTGGACTTTACACGTGAGGAGTGGAAATTGCTGG
ATACTGCGCAACAAATTGTGTATCGAAATGTCATGCTTGAGAATTACAAGAACCT
CGTCAGTCTCGGATACCAGTTGACGAAACCGGATGTGATCCTTAGGCTCGAAAA
GGGGGAAGAACCTTGGCTGGTATAG

The invention claimed is:

1. A non-naturally occurring zinc finger protein, wherein the zinc finger protein specifically binds to the promoter region of the Myd88 gene.

2. The zinc finger protein of claim 1, wherein the zinc finger comprises one or more of the following:

(i) a N-terminal fixed domain, (ii) a N-terminal backbone domain, (iii) a variable recognition helix, (iv) a C-terminal backbone domain, (v) a zinc finger linker, and (vi) a C-terminal domain.

3. The zinc finger protein of claim 1, further comprising one or more repressors.

4. The zinc finger protein of claim 3, wherein the one or more repressors are selected from the group consisting of Hp1a, Krab, MeCP2, and combinations thereof.

5. The zinc finger protein of claim 3, wherein the one or more repressors are Hp1a and Krab.

6. The zinc finger protein of claim 3, wherein the one or more repressors comprise the amino acid sequence encoded by the nucleotide sequence of SEQ ID NO: 8 (Hp1a), the amino acid sequence encoded by the nucleotide sequence of SEQ ID NO: 9 (Krab), or a combination thereof.

7. A cell comprising one or more zinc finger proteins of claim 1.

8. A polynucleotide encoding one or more zinc finger proteins of claim 1.

9. The polynucleotide of claim 8, wherein the polynucleotide is a mRNA.

10. A vector comprising the polynucleotide of claim 8.

11. The vector of claim 10, wherein the vector is an adeno-associated virus (AAV) vector, adenovirus vector, poxvirus vector, retrovirus vector, herpes virus vector, polio virus vector, or alphavirus vector.

12. A pharmaceutical composition comprising (i) one or more zinc finger proteins of claim 1, (ii) one or more cells comprising the one or more zinc finger proteins, (iii) one or more polynucleotides encoding the one or more zinc finger proteins, or (iv) one or more vectors comprising the one or more polynucleotides and a pharmaceutically acceptable carrier.

13. A pharmaceutical composition comprising a pharmaceutically acceptable carrier and:

(A) (i) one or more zinc finger proteins of claim 1, (ii) one or more cells comprising the one or more zinc finger proteins, (iii) one or more polynucleotides encoding the one or more zinc finger proteins, or (iv) one or more vectors comprising the one or more polynucleotides;

(B) a target antigen or a polynucleotide encoding the target antigen; and (C) a gene therapy.

14. A set of compositions comprising:

(A) (i) one or more zinc finger proteins of claim 1, (ii) one or more cells comprising the one or more zinc finger proteins, (iii) one or more polynucleotides encoding the one or more zinc finger proteins, or (iv) one or more vectors comprising the one or more polynucleotides;

(B) a target antigen or a polynucleotide encoding the target antigen; and (C) a gene therapy.

15. A pharmaceutical composition comprising a pharmaceutically acceptable carrier and:

(A) (i) one or more RNA interference (RNAi) agents targeting the Myd88 gene, (ii) one or more cells comprising the one or more RNAi agents, (iii) one or more polynucleotides encoding the one or more RNAi agents, or (iv) one or more vectors comprising the one or more polynucleotides;

(B) a target antigen or a polynucleotide encoding the target antigen; and (C) a gene therapy.

16. A set of compositions comprising:

(A) (i) one or more RNA interference (RNAi) agents targeting the Myd88 gene, (ii) one or more cells comprising the one or more RNAi agents, (iii) one or more polynucleotides encoding the one or more RNAi agents, or (iv) one or more vectors comprising the one or more polynucleotides;

(B) a target antigen or a polynucleotide encoding the target antigen; and (C) a gene therapy.

17. A method for ameliorating inflammation and/or immune response in a subject, the method comprising administering to the subject a therapeutically effective amount of (i) one or more zinc finger proteins of claim 1, (ii) one or more cells comprising the one or more zinc finger proteins, (iii) one or more polynucleotides encoding the one or more zinc finger proteins, (iv) one or more vectors comprising the one or more polynucleotides, or (v) a pharmaceutical composition comprising any one of (i)-(iv), thereby ameliorating inflammation and/or immune response in the subject.

18. A method for inducing immune tolerance in a subject, the method comprising administering to the subject a therapeutically or prophylactically effective amount of (i) one or more zinc finger proteins of claim 1, (ii) a target antigen or a polynucleotide encoding the target antigen, (iii) one or more cells comprising (i) and (ii), (iv) one or more polynucleotides encoding (i), (v) one or more vectors comprising the one or more polynucleotides, or (vi) a pharmaceutical composition comprising any one of (i)-(v), thereby inducing immunogenic tolerance against the target antigen.

19. A method for inducing immune tolerance in a subject, the method comprising administering to the subject a therapeutically or prophylactically effective amount of:

(A) (i) one or more RNA interference (RNAi) agents targeting the Myd88 gene, (ii) one or more cells comprising the one or more RNAi agents, (iii) one or more polynucleotides encoding the one or more RNAi agents, or (iv) one or more vectors comprising the one or more polynucleotides;

(B) a target antigen or a polynucleotide encoding a target antigen; and (C) a gene therapy, thereby inducing immunogenic tolerance against the target antigen.

20. The composition of claim 15, wherein the pharmaceutically acceptable carrier is lipid nanoparticles.

* * * * *

SEQUENCE LISTING

```
Sequence total quantity: 13
SEQ ID NO: 1            moltype = AA  length = 7
FEATURE                 Location/Qualifiers
source                  1..7
```

-continued mol_type = protein
organism = synthetic construct
SEQUENCE: 1
LEPGEKP 7

SEQ ID NO: 2 moltype = AA length = 11
FEATURE Location/Qualifiers
source 1..11
mol_type = protein
organism = synthetic construct
SEQUENCE: 2
YKCPECGKSF S 11

SEQ ID NO: 3 moltype = AA length = 5
FEATURE Location/Qualifiers
source 1..5
mol_type = protein
organism = synthetic construct
SEQUENCE: 3
HQRTH 5

SEQ ID NO: 4 moltype = AA length = 5
FEATURE Location/Qualifiers
source 1..5
mol_type = protein
organism = synthetic construct
SEQUENCE: 4
TGEKP 5

SEQ ID NO: 5 moltype = AA length = 6
FEATURE Location/Qualifiers
source 1..6
mol_type = protein
organism = synthetic construct
SEQUENCE: 5
TGKKTS 6

SEQ ID NO: 6 moltype = DNA length = 660
FEATURE Location/Qualifiers
source 1..660
mol_type = other DNA
organism = synthetic construct
SEQUENCE: 6
atggactaca aagaccatga cggtgattat aaagatcatg acatcgatta caaggatgac 60
gatgacaaga tggcccccaa gaagaagagg aaggtcggca ttcatggggt acccgccgct 120
atggctgaga ggcccttcca gtgtcgaatc tgcatgcgta acttcagtcg ctccgaccac 180
ctgtcccgcc acatccgcac ccacaccggc gagaagcctt ttgcctgtga catttgtggg 240
aggaaatttg ccgaccgctc cgtgctggcc cgccatacca agatacacac gggcagccaa 300
aagcccttcc agtgtcgaat ctgcatgcgt aacttcagtg accgctccca cctgacccgc 360
cacatccgca cccacaccgg cgagaagcct tttgcctgtg acatttgtgg gaggaaattt 420
gccgaccgct ccaacctgac ccgccatacc aagatacaca cgggatctca gaagcccttc 480
cagtgtcgaa tctgcatgcg taacttcagt cgctccgacg tgctgtccga gcacatccgc 540
acccacaccg gcgagaagcc ttttgcctgt gacatttgtg ggaggaaatt tgcccagtcc 600
ggctccctga cccgccatac caagatacac ctgcgccaaa aagatgcggc ccggggatcc 660

SEQ ID NO: 7 moltype = DNA length = 599
FEATURE Location/Qualifiers
source 1..599
mol_type = other DNA
organism = synthetic construct
SEQUENCE: 7
atggactaca aagaccatga cggtgattat aaagatcatg acatcgatta caaggatgac 60
gatgacaaga tggcccccaa gaagaagagg aaggtcggca tccacggggt acccgccgct 120
atggctgaga ggcccttcca gtgtcgaatc tgcatgcgta acttcagtga ccgctccgcc 180
ctgtcccgcc acatccgcac ccacaccggc gagaagcctt ttgcctgtga catttgtggg 240
aggaaatttg cccgctccga ccacctgtcc cgccatacca agatacacac gggcagccaa 300
aagcccttcc agtgtcgaat ctgcatgcgt aacttcagtc gctccgacga cctgacccgc 360
cacatccgca cccacaccgg cgagaagcct tttgcctgtg acatttgtgg gaggaaattt 420
gccgaccgct ccaacctgaa ggcccatacc aagatacaca cgggatctca gaagcccttc 480
cagtgtcgaa tctgcatgcg taacttcagt gactcctccg accgcaagaa gcacatccgc 540
acccacaccg gcgagaagcc ttttgcctgt gacatttgtg ggaggaaatt tgcccagtc 599

SEQ ID NO: 8 moltype = DNA length = 390
FEATURE Location/Qualifiers
source 1..390
mol_type = other DNA
organism = synthetic construct
SEQUENCE: 8
agccccaaga aaaaacggaa agtggaggca tcaatgaagg agggagaaaa caacaaaccc 60

```
agggagaaaa gtgaagggaa taagagaaaa agctccttct ctaacagtgc agacgatatc  120
aagtccaaga aaaagcggga gcagtctaat gacattgcta ggggcttcga gagaggactg  180
gagccagaaa aaatcattgg ggcaaccgac agctgcggcg atctgatgtt tctcatgaaa  240
tggaaggaca cagatgaggc cgacctggtg ctcgccaaag aagctaacgt gaagtgtccc  300
cagatcgtca ttgcttttta cgaggaaagg ctcacctggc acgcatatcc tgaggatgcc  360
gaaaacaagg agaaggaatc agctaagagc                                   390

SEQ ID NO: 9            moltype = DNA  length = 225
FEATURE                 Location/Qualifiers
source                  1..225
                        mol_type = other DNA
                        organism = synthetic construct
SEQUENCE: 9
atggacgcga aatcacttac ggcatggtcg agaacactgg ttacgttcaa ggacgtgttt  60
gtggacttta cacgtgagga gtggaaattg ctggatactg cgcaacaaat tgtgtatcga  120
aatgtcatgc ttgagaatta caagaacctc gtcagtctcg gataccagtt gacgaaaccg  180
gatgtgatcc ttaggctcga aaagggggaa gaaccttggc tggta                  225

SEQ ID NO: 10           moltype = DNA  length = 1365
FEATURE                 Location/Qualifiers
source                  1..1365
                        mol_type = other DNA
                        organism = synthetic construct
SEQUENCE: 10
atggactaca aagaccatga cggtgattat aaagatcatg acatcgatta caaggatgac  60
gatgacaaga tggcccccaa gaagaagagg aaggtcggca ttcatggggt acccgccgct  120
atggctgaga ggcccttcca gtgtcgaatc tgcatgcgta acttcagtcg ctccgaccac  180
ctgtcccgcc acatccgcac ccacaccggc gagaagcctt ttgcctgtga catttgtggg  240
aggaaatttg ccgaccgctc cgtgctggcc cgccatacca agatacacac gggcagccaa  300
aagcccttcc agtgtcgaat ctgcatgcgt aacttcagtg accgctccca cctgacccgc  360
cacatccgca cccacaccgg cgagaagcct tttgcctgtg acatttgtgg gaggaaattt  420
gccgaccgct ccaacctgac ccgccatacc aagatacaca cgggatctca gaagcccttc  480
cagtgtcgaa tctgcatgcg taacttcagt cgctccgacg tgctgtccga gcacatccgc  540
acccacaccg gcgagaagcc ttttgcctgt gacatttgtg ggaggaaatt tgcccagtcc  600
ggctccctga cccgccatac caagatacac ctgcgccaaa aagatgcggc ccggggatcc  660
ccatggccca agaagaagag gaaggtgagt ggtggaggaa gtggcgggtc agggtcgagc  720
cccaagaaaa aacggaaagt ggaggcatca atgaaggagg gagaaaacaa caaacccagg  780
gagaaaagtg aagggaataa gagaaaaagc tccttctcta acagtgcaga cgatatcaag  840
tccaagaaaa agcgggagca gtctaatgac attgctaggg gcttcgagag aggactggag  900
ccagaaaaaa tcattggggc aaccgacagc tgcggcgatc tgatgtttct catgaaatgg  960
aaggacacag atgaggccga cctggtgctc gccaaagaag ctaacgtgaa gtgtccccag  1020
atcgtcattg ctttttacga ggaaaggctc acctggcacg catatcctga ggatgccgaa  1080
aacaaggaga aggaatcagc taagagctcg ggaggtggtt cgggtggctc tggatcaatg  1140
gacgcgaaat cacttacggc atggtcgaga acactggtta cgttcaagga cgtgtttgtg  1200
gactttacac gtgaggagtg gaaattgctg gatactgcgc aacaaattgt gtatcgaaat  1260
gtcatgcttg agaattacaa gaacctcgtc agtctcggat accagttgac gaaaccggat  1320
gtgatcctta ggctcgaaaa gggggaagaa ccttggctgg tatag                  1365

SEQ ID NO: 11           moltype = DNA  length = 1365
FEATURE                 Location/Qualifiers
source                  1..1365
                        mol_type = other DNA
                        organism = synthetic construct
SEQUENCE: 11
atggactaca aagaccatga cggtgattat aaagatcatg acatcgatta caaggatgac  60
gatgacaaga tggcccccaa gaagaagagg aaggtcggca tccacggggt acccgccgct  120
atggctgaga ggcccttcca gtgtcgaatc tgcatgcgta acttcagtga ccgctccgcc  180
ctgtcccgcc acatccgcac ccacaccggc gagaagcctt ttgcctgtga catttgtggg  240
aggaaatttg cccgctccga ccacctgtcc cgccatacca agatacacac gggcagccaa  300
aagcccttcc agtgtcgaat ctgcatgcgt aacttcagtc gctccgacga cctgacccgc  360
cacatccgca cccacaccgg cgagaagcct tttgcctgtg acatttgtgg gaggaaattt  420
gccgaccgct ccaacctgaa ggcccatacc aagatacaca cgggatctca gaagcccttc  480
cagtgtcgaa tctgcatgcg taacttcagt gactcctccg accgcaagaa gcacatccgc  540
acccacaccg gcgagaagcc ttttgcctgt gacatttgtg ggaggaaatt tgcccagtcc  600
ggccacctgt cccgccatac caagatacac ctgcgccaaa aagatgcggc ccggggatcc  660
ccatggccca agaagaagag gaaggtgagt ggtggaggaa gtggcgggtc agggtcgagc  720
cccaagaaaa aacggaaagt ggaggcatca atgaaggagg gagaaaacaa caaacccagg  780
gagaaaagtg aagggaataa gagaaaaagc tccttctcta acagtgcaga cgatatcaag  840
tccaagaaaa agcgggagca gtctaatgac attgctaggg gcttcgagag aggactggag  900
ccagaaaaaa tcattggggc aaccgacagc tgcggcgatc tgatgtttct catgaaatgg  960
aaggacacag atgaggccga cctggtgctc gccaaagaag ctaacgtgaa gtgtccccag  1020
atcgtcattg ctttttacga ggaaaggctc acctggcacg catatcctga ggatgccgaa  1080
aacaaggaga aggaatcagc taagagctcg ggaggtggtt cgggtggctc tggatcaatg  1140
gacgcgaaat cacttacggc atggtcgaga acactggtta cgttcaagga cgtgtttgtg  1200
gactttacac gtgaggagtg gaaattgctg gatactgcgc aacaaattgt gtatcgaaat  1260
gtcatgcttg agaattacaa gaacctcgtc agtctcggat accagttgac gaaaccggat  1320
gtgatcctta ggctcgaaaa gggggaagaa ccttggctgg tatag                  1365

SEQ ID NO: 12           moltype = DNA  length = 18
```

-continued

```
FEATURE                Location/Qualifiers
source                 1..18
                       mol_type = genomic DNA
                       organism = Mus musculus
SEQUENCE: 12
ggagggggag gaaggggg                                                18

SEQ ID NO: 13          moltype = DNA  length = 648
FEATURE                Location/Qualifiers
source                 1..648
                       mol_type = other DNA
                       organism = synthetic construct
SEQUENCE: 13
agccccaaga aaaaacggaa agtggaggca tcaatgaagg agggagaaaa caacaaaccc  60
agggagaaaa gtgaagggaa taagagaaaa agctccttct ctaacagtgc agacgatatc  120
aagtccaaga aaaagcggga gcagtctaat gacattgcta ggggcttcga gagaggactg  180
gagccagaaa aaatcattgg ggcaaccgac agctgcggcg atctgatgtt tctcatgaaa  240
tggaaggaca cagatgaggc cgacctggtg ctcgccaaag aagctaacgt gaagtgtccc  300
cagatcgtca ttgcttttta cgaggaaagg ctcacctggc acgcatatcc tgaggatgcc  360
gaaaacaagg agaaggaatc agctaagagc tcgggaggtg gttcgggtgg ctctggatca  420
atggacgcga aatcacttac ggcatggtcg agaacactgg ttacgttcaa ggacgtgttt  480
gtggacttta cacgtgagga gtggaaattg ctggatactg cgcaacaaat tgtgtatcga  540
aatgtcatgc ttgagaatta caagaacctc gtcagtctcg gataccagtt gacgaaaccg  600
gatgtgatcc ttaggctcga aaagggggaa gaaccttggc tggtatag               648
```